(12) United States Patent
Sun et al.

(10) Patent No.: US 9,395,354 B2
(45) Date of Patent: Jul. 19, 2016

(54) CARDIOMYOCYTES FROM INDUCED PLURIPOTENT STEM CELLS FROM PATIENTS AND METHODS OF USE THEREOF

(75) Inventors: Ning Sun, Stanford, CA (US); Michael T. Longaker, Stanford, CA (US); Robert C. Robbins, Stanford, CA (US); Joseph Wu, Stanford, CA (US); Feng Lan, Menlo Park, CA (US); Andrew Stephen Lee, Palo Alto, CA (US); Paul W. Burridge, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 13/554,946

(22) Filed: Jul. 20, 2012

(65) Prior Publication Data

US 2013/0029866 A1   Jan. 31, 2013

Related U.S. Application Data

(60) Provisional application No. 61/510,422, filed on Jul. 21, 2011.

(51) Int. Cl.
| | |
|---|---|
| *C12Q 1/02* | (2006.01) |
| *G01N 27/49* | (2006.01) |
| *G01N 33/50* | (2006.01) |
| *C12N 5/077* | (2010.01) |
| *C12N 5/074* | (2010.01) |

(52) U.S. Cl.
CPC .......... *G01N 33/5073* (2013.01); *C12N 5/0657* (2013.01); *C12N 5/0696* (2013.01); *G01N 33/5061* (2013.01); *C12N 2501/602* (2013.01); *C12N 2501/603* (2013.01); *C12N 2501/604* (2013.01); *C12N 2501/606* (2013.01); *C12N 2506/1307* (2013.01); *C12N 2506/45* (2013.01); *C12N 2510/00* (2013.01); *G01N 2800/324* (2013.01); *G01N 2800/325* (2013.01)

(58) Field of Classification Search
CPC ..................... C12N 2510/00; C12N 2501/604; C12N 2506/45; C12N 2501/602; C12N 2501/606
USPC .......................................................... 506/9
See application file for complete search history.

(56) References Cited

U.S. PATENT DOCUMENTS

| | | | |
|---|---|---|---|
| 4,568,649 A | 2/1986 | Bertoglio-matte | |
| 5,989,833 A | 11/1999 | Charon et al. | |
| 6,099,832 A | 8/2000 | Mickle et al. | |
| 7,452,718 B2 | 11/2008 | Gold et al. | |
| 7,851,167 B2 | 12/2010 | Xu | |
| 8,058,065 B2 | 11/2011 | Yamanaka et al. | |
| 8,071,369 B2 | 12/2011 | Jaenisch et al. | |
| 8,257,941 B2 | 9/2012 | Sakurada et al. | |
| 8,293,529 B2 | 10/2012 | Koshimizu et al. | |
| 8,318,488 B1 | 11/2012 | Bohlen et al. | |
| 8,415,155 B2 | 4/2013 | Stankewicz et al. | |
| 8,669,048 B2 | 3/2014 | Reijo Pera et al. | |
| 8,932,856 B2 | 1/2015 | Jaenisch et al. | |
| 2009/0227469 A1 | 9/2009 | Conklin et al. | |
| 2010/0144031 A1 | 6/2010 | Jaenisch et al. | |
| 2010/0166713 A1 | 7/2010 | Dalton et al. | |
| 2010/0166714 A1* | 7/2010 | Chien et al. | 424/93.7 |
| 2011/0028331 A1 | 2/2011 | Milewicz et al. | |
| 2012/0137394 A1* | 5/2012 | Butte et al. | 850/1 |
| 2013/0109089 A1 | 5/2013 | Jaenisch et al. | |
| 2013/0109090 A1 | 5/2013 | Jaenisch et al. | |
| 2013/0189785 A1 | 7/2013 | Palecek et al. | |

FOREIGN PATENT DOCUMENTS

| | | |
|---|---|---|
| EP | 1745144 | 1/2010 |
| WO | 03006950 | 1/2003 |
| WO | 2004011603 | 2/2004 |
| WO | 2007002136 | 1/2007 |
| WO | 2007030870 | 3/2007 |
| WO | WO 2008/094597 A2 | 8/2008 |
| WO | 2009017460 | 2/2009 |
| WO | WO 2009/114133 A1 | 9/2009 |
| WO | 2011044253 | 4/2011 |
| WO | WO 2013/056072 A1 | 4/2013 |

OTHER PUBLICATIONS

Ho et al., Aging, Apr. 1, 2011, vol. 3, No. 1, pp. 380-390.*
Mogensen et al., Journal of the American College of Cardiology, 2004, vol. 44, No. 10, pp. 2033-2040.*
Freund et al., Journal of Cellular Biochemistry, 2009, 107(4), pp. 592-599.*
Matsa et al., European Heart Journal, 2011, 32, pp. 952-962.*
Hein et al., Current Opinion Cardiology, May 1996, 11(3), pp. 293-301.*
Koike et al., Cytotechnology, 2005, 47, pp. 3-10.*
Ghosh; et al. "Recent progress in the genetics of cardiomyopathy and its role in the clinical evaluation of patients with cardiomyopathy", Curr Opin Cardiol (Mar. 2011), 26(2):155-164.
Millat; et al. "Development of a high resolution melting method for the detection of genetic variations in hypertrophic cardiomyopathy", Clin Chim Acta (Dec. 2010), 411(23-24):1983-1991.

(Continued)

*Primary Examiner* — Larry Riggs
*Assistant Examiner* — Karla Dines
(74) *Attorney, Agent, or Firm* — Pamela J. Sherwood; Bozicevic, Field & Francis LLP

(57) ABSTRACT

Human somatic cells obtained from individuals with a genetic heart condition are reprogrammed to become induced pluripotent stem cells (iPS cells), and differentiated into cardiomyocytes for use in analysis, screening programs, and the like.

54 Claims, 34 Drawing Sheets
(29 of 34 Drawing Sheet(s) Filed in Color)

(56) References Cited

OTHER PUBLICATIONS

Syrris; et al; "Clinical expression of plakophilin-2 mutations in familial arrhythmogenic right ventricular cardiomyopathy", Circulation (Jan. 2006), 113(3):356-364.

Zhang; et al. "Functional cardiomyocytes derived from human induced pluripotent stem cells", Circ Res (Feb. 2009), 104(4):e30-41.

Zwi; et al. "Cardiomyocyte differentiation of human induced pluripotent stem cells", Circulation (Oct. 2009), 120(15):1513-1523.

Carvajal-Vergara; et al., "Patient-specific induced pluripotent stem-cell-derived models of LEOPARD syndrome", Nature (Jun. 2010), 465(7299):808-12.

Itzhaki; et al., "Modelling the long QT syndrome with induced pluripotent stem cells", Nature (Mar. 2011), 471 (7337):225-9.

Moretti; et al., "Patient-Specific Induced Pluripotent Stem-Cell Models for Long-QT Syndrome", The New England Journal of Medicine (Oct. 2010), 363(15):1397-1409.

Ausubel, et al. Current Protocols in Molecular Biology, eds, John Wiley & Sons, New York, NY, 2000.

Ausubel, et al. Short Protocols in Molecular Biology, 4th Ed. eds., John Wiley & Sons 1999.

Chen, et al. Endothelial cells regulate cardiomyocyte development from embryonic stem cells. J Cell Biochem. Sep. 1, 2010;111(1):29-39. doi: 10.1002/jcb.22680.

Chen, et al. Profiling expression patterns and isolating differentially expressed genes by cDNA microarray system with colorimetry detection. Genomics. Aug 1, 1998;51(3):313-24.

Chiu, et al. Cellular cardiomyoplasty: myocardial regeneration with satellite cell implantation. Ann Thorac Surg. Jul. 1995;60(1):12-8.

Dambrot, et al. Cardiomyocyte differentiation of pluripotent stem cells and their use as cardiac disease models. Biochem J. Feb. 15, 2011;434(1):25-35. doi: 10.1042/BJ20101707.

Foldes, et al. Modulation of human embryonic stem cell-derived cardiomyocyte growth: a testbed for studying human cardiac hypertrophy? J Mol Cell Cardiol. Feb. 2011;50(2):367-76. doi: 10.1016/j.yjmcc.2010.10.029. Epub Nov. 1, 2010.

Freeman, et al. Quantitative RT-PCR: pitfalls and potential. Biotechniques. Jan. 1999;26(1):112-22, 124-5.

Fujiwara, et al. Induction and enhancement of cardiac cell differentiation from mouse and human induced pluripotent stem cells with cyclosporin-A. PLoS One. Feb. 22, 2011;6(2):e16734. doi: 10.1371/journal.pone.0016734.

Huangfu, et al. Induction of pluripotent stem cells from primary human fibroblasts with only Oct4 and Sox2. Nat Biotechnol. Nov. 2008;26(11):1269-75. doi: 10.1038/nbt.1502. Epub Oct. 12, 2008.

Jones, et al. Glowing jellyfish, luminescence and a molecule called coelenterazine. Trends Biotechnol. Dec. 1999;17(12):477-81.

Kaji, et al. Virus-free induction of pluripotency and subsequent excision of reprogramming factors. Nature. Apr. 9, 2009;458(7239):771-5. doi: 10.1038/nature07864. Epub Mar. 1, 2009.

Kawamoto, et al. Expression profiling by iAFLP: A PCR-based method for genome-wide gene expression profiling. Genome Res. Dec. 1999;9(12):1305-12.

Kim, et al. Generation of human induced pluripotent stem cells by direct delivery of reprogramming proteins. Cell Stem Cell. Jun. 5, 2009;4(6):472-6. doi: 10.1016/j.stem.2009.05.005. Epub May 28, 2009.

Lan, et al. Abnormal calcium handling properties underlie familial hypertrophic cardiomyopathy pathology in patient-specific induced pluripotent stem cells. Cell Stem Cell. Jan. 3, 2013;12(1):101-13. doi: 10.1016/j.stem.2012.10.010.

Lan, et al. Abnormal calcium handling properties underlie familial hypertrophic cardiomyopathy pathology in patient-specific induced pluripotent stem cells. Cell Stem Cell. Jan. 3, 2013;12(1):101-13. doi: 10.1016/j.stem.2012.10.010. Supplemental Material.

Li, et al. Generation of rat and human induced pluripotent stem cells by combining genetic reprogramming and chemical inhibitors. Cell Stem Cell. Jan. 9, 2009;4(1):16-9. doi: 10.1016/j.stem.2008.11.014. Epub Dec. 18, 2008.

Li, et al. Overexpression of insulin-like growth factor-1 in mice protects from myocyte death after infarction, attenuating ventricular dilation, wall stress, and cardiac hypertrophy. J Clin Invest. Oct. 15, 1997;100(8):1991-9.

Mignone, et al. Cardiogenesis from human embryonic stem cells. Circ J. Nov. 2010;74(12):2517-26. Epub Nov. 12, 2010.

Murry, et al. Muscle differentiation during repair of myocardial necrosis in rats via gene transfer with MyoD. J Clin Invest. Nov. 15, 1996;98(10):2209-17.

Niwa, et al. Quantitative expression of Oct-3/4 defines differentiation, dedifferentiation or self-renewal of ES cells. Nat Genet. Apr. 2000;24(4):372-6.

Okita, et al. Generation of mouse induced pluripotent stem cells without viral vectors. Science. Nov. 7, 2008;322(5903):949-53. doi: 10.1126/science.1164270. Epub Oct. 9, 2008.

Park, et al. Reprogramming of human somatic cells to pluripotency with defined factors. Nature. Jan. 10, 2008;451(7175):141-6. Epub Dec. 23, 2007.

Rathjen, et al. Properties and uses of embryonic stem cells: prospects for application to human biology and gene therapy. Reprod Fertil Dev. 1998;10(1):31-47.

Reinecke, et al. Survival, integration, and differentiation of cardiomyocyte grafts: a study in normal and injured rat hearts. Circulation. Jul. 13, 1999;100(2):193-202.

Robertson, et al. Concise Review: Maturation Phases of Human Pluripotent Stem Cell-Derived Cardiomyocytes. Stem Cells 2013: 31: 829-837.

Sambrook, et al. Molecular Cloning: A Laboratory Manual, 3rd Ed. Harbor Laboratory Press 2001.

Soldner, et al. Parkinson's disease patient-derived induced pluripotent stem cells free of viral reprogramming factors. Cell. Mar. 6, 2009;136(5):964-77. doi: 10.1016/j.cell.2009.02.013.

Stadtfeld, et al. Induced pluripotent stem cells generated without viral integration. Science. Nov. 7, 2008;322(5903):945-9. doi: 10.1126/science.1162494. Epub Sep. 25, 2008.

Sun, et al. Patient-specific induced pluripotent stem cells as a model for familial dilated cardiomyopathy. Sci Transl Med. Apr. 18, 2012;4(130):130ra47. doi: 10.1126/scitranslmed.3003552.

Takahashi, et al. Induction of pluripotent stem cells from adult human fibroblasts by defined factors. Cell. Nov. 30, 2007;131(5):861-72.

Takei, et al. Bone morphogenetic protein-4 promotes induction of cardiomyocytes from human embryonic stem cells in serum-based embryoid body development. Am J Physiol Heart Circ Physiol. Jun. 2009;296(6):H1793-803. doi: 10.1152/ajpheart.01288.2008. Epub Apr. 10, 2009.

Tran, et al. Wnt3a-induced mesoderm formation and cardiomyogenesis in human embryonic stem cells. Stem Cells. Apr. 23, 2009; 27(8):1869-1878.

Wang, et al. Enhancement of cardiomyocyte differentiation from human embryonic stem cells. Sci China Life Sci. May 2010;53(5):581-9. doi: 10.1007/s11427-010-01117. Epub May 23, 2010.

Wiles, MV. Embryonic stem cell differentiation in vitro. Methods Enzymol. 1993;225:900-18.

Woltjen, et al. piggyBac transposition reprograms fibroblasts to induced pluripotent stem cells. Nature. Apr. 9, 2009;458(7239):766-70. doi: 10.1038/nature07863. Epub Mar. 1, 2009.

Xu, et al. Efficient generation and cryopreservation of cardiomyocytes derived from human embryonic stem cells. Regen Med. Jan. 2011;6(1):53-66. doi: 10.2217/rme.10.91.

Yang, et al. Engineering Adolescence: Maturation of Human Pluripotent Stem Cell-Derived Cardiomyocytes. Circ Res. 2014; 114: 511-523.

Yu, et al. Induced pluripotent stem cell lines derived from human somatic cells. Science. Dec. 21, 2007;318(5858):1917-20. Epub Nov. 20, 2007.

Yuasa, et al. Transient inhibition of BMP signaling by Noggin induces cardiomyocyte differentiation of mouse embryonic stem cells. Nat Biotechnol. May 2005;23(5):607-11. Epub May 1, 2005.

Isolated Adult Cardiomyocytes (vols. I & II, Piper & Isenberg eds, CRC Press 1989).

(56) References Cited

OTHER PUBLICATIONS

Matsa, et al. Human stem cells for modeling heart disease and for drug discovery. Sci Transl Med. Jun. 4, 2014;6(239):239ps6. doi: 10.1126/scitranslmed.3008921.

The Heart Cell in Culture (A. Pinson ed., CRC Press 1987).

Millat et al. "Development of a high resolution melting method for the detection of genetic variations in hypertrophic cardiomyopathy" Clinica Chimica Acta 411 pp. 1983-1991(2010) Philadelphia, PA.

Landstrom et al. "Mutation Type Is Not Clinically Useful in Predicting Prognosis in Hypertrophic Cardiomyopathy" Circulation, 122: Dec. 7, 2010, pp. 2441-2450; Circulation American Heart Association, Dallas, TX.

Choi et al. "A comparison of genetically matched cell lines reveals the equivalence of human iPSCSCs and ESCs", Nature Biotechnology, published online Oct. 26, 2015, pp. 1-11, Nature America, Inc., New York, NY.

Inoue et al.,"The Use of Induced Pluripotent Stem Cells in Drug Development", Clinical Pharmacology & Therapeutics, May 2011, vol. 89, No. 5, p. 655-661, Nature Publishing Group, New York, NY.

Hershberger et al., "Clinical and Functional Characterization of TNNT2 Mutations Identified in Patients with Dilated Cardiomyopathy", Circ Cardiovas Genet, Apr. 20, 2009, vol. 2, p. 306-313, Circulation Genetics American Heart Association, Dallas, TX.

Ahmad et al., "The Role of Cardiac Troponin T Quantity and Function in Cardiac Development and Dilated Cardiomyopathy", PLoS One, Jul. 9, 2008, vol. 3, No. 7, e2642, pp. 2-11, PLoS One, San Francisco, CA.

den Hann et al., Comprehensive Desmosome Mutation Analysis in North Americans with Arrhythmogenic Right Ventricular Dysplasia/ Cardiomyopathy, Circ Cardiovas Genet, May 27, 2009, vol. 2, p. 428-435, Circulation Genetics American Heart Association, Dallas, TX.

* cited by examiner

CARDIOMYOCYTES FROM INDUCED PLURIPOTENT STEM CELLS FROM PATIENTS AND METHODS OF USE THEREOF

FEDERALLY SPONSORED RESEARCH AND DEVELOPMENT

This invention was made with Government support under contract HL099776 awarded by the National Institutes of Health. The Government has certain rights in this invention.

BACKGROUND OF THE INVENTION

A variety of cardiac disorders have an underlying genetic cause. For example, dilated cardiomyopathy (DCM) is a cardiac disease characterized by ventricular dilatation and systolic dysfunction. DCM is the most common cause of heart failure after coronary artery disease and hypertension, as well as the leading indication for heart transplantations. The cost for management of DCM in the US alone has been estimated at between $4 and $10 billion. Another important condition for therapy is hypertrophic cardiomyopathy (HCM), in which the sarcomeres replicate, causing cardiomyocytes to increase in size. In addition, the normal alignment of cardiomyocytes is disrupted, a phenomenon known as myocardial disarray. HCM is most commonly due to a mutation in one of nine sarcomeric genes.

Mutations in genes encoding sarcomeric, cytoskeletal, mitochondrial, and nuclear membrane proteins, as well as proteins involved in calcium metabolism, are associated with approximately a third to half the cases of DCM. Cardiac troponin T (cTnT) is one of the 3 subunits of the troponin complex (Troponin T, C, and I) that regulate the sarcomeric thin filament activity and muscle contraction in cardiomyocytes (CMs). cTnT is essential for sarcomere assembly, contraction, and force production. Mutations in the cardiac troponin T gene (TNNT2) often lead to DCM and are frequently expressed as a malignant phenotype with sudden cardiac death and heart failure at an early age. In vitro biochemical studies have found that decreased $Ca^{2+}$ sensitivity and/or ATPase activity, which lead to impaired force production, may be the underlying mechanisms for certain TNNT2-mutation induced DCM.

Mouse models of TNNT2 mutations recapitulate the human DCM phenotype and have provided extensive insight into the possible mechanisms of the disease. However, several differences exist between the mouse and human models. For example, mouse resting heart rate is approximately 10-fold faster than human. The electrical properties, ion channel contributions, and cardiac development of mouse CMs are also different from those of human. The lack of complex intracellular interactions within cardiomyocytes for in vitro biochemical assays and species differences for mouse models undercut the value of these methodologies for understanding the cellular and physiological processes of DCM as well as for drug screening.

In addition, cardiac tissues from DCM patients are difficult to obtain and do not survive in long-term culture. Effective cellular models for dilated cardiomyopathy and other genetic cardiac conditions are of great interest for screening and development of effective therapies.

Pharmaceutical drug discovery, a multi-billion dollar industry, involves the identification and validation of therapeutic targets, as well as the identification and optimization of lead compounds. The explosion in numbers of potential new targets and chemical entities resulting from genomics and combinatorial chemistry approaches over the past few years has placed enormous pressure on screening programs. The rewards for identification of a useful drug are enormous, but the percentages of hits from any screening program are generally very low. Desirable compound screening methods solve this problem by both allowing for a high throughput so that many individual compounds can be tested; and by providing biologically relevant information so that there is a good correlation between the information generated by the screening assay and the pharmaceutical effectiveness of the compound.

Some of the more important features for pharmaceutical effectiveness are specificity for the targeted cell or disease, a lack of toxicity at relevant dosages, and specific activity of the compound against its molecular target. The present invention addresses this issue.

Publications.

Methods to reprogram primate differentiated somatic cells to a pluripotent state include differentiated somatic cell nuclear transfer, differentiated somatic cell fusion with pluripotent stem cells and direct reprogramming to produce induced pluripotent stem cells (iPS cells) (Takahashi K, et al. (2007) Cell 131:861-872; Park I H, et al. (2008) Nature 451: 141-146; Yu J, et al. (2007) Science 318:1917-1920; Kim D, et al. (2009) Cell Stem Cell 4:472-476; Soldner F, et al. (2009) Cell. 136:964-977; Huangfu D, et al. (2008) Nature Biotechnology 26:1269-1275; Li W, et al. (2009) Cell Stem Cell 4:16-19).

Additional publications of interest include Stadtfeld et al. Science 322, 945-949 (2008); Okita et al. Science 322, 949-953 (2008); Kaji et al. Nature 458, 771-775 (2009); Soldner et al. Cell 136, 964-977 (2009); Woltjen et al. Nature 458, 766-770 (2009); Yu et al. Science (2009).

SUMMARY OF THE INVENTION

Compositions and methods are provided for disease-relevant screening of cardiomyocytes for therapeutic drugs and treatment regimens, where the methods utilize in vitro cell cultures or animal models derived therefrom. Diseases of particular interest include dilated cardiomyopathy (DCM); hypertrophic cardiomyopathy (HCM); anthracycline-induced cardiotoxicity; arrhythmogenic right ventricular dysplasia (ARVD); left ventricular non-compaction (LVNC); double inlet left ventricle (DILV); and long QT (Type-1) syndrome (LQT-1), in which there is a genetic basis for the disease. The methods utilize induced human pluripotent stem cells (iPS cells), which may be obtained from patient or carrier cell samples, e.g. adipocytes, fibroblasts, and the like.

In some embodiments of the invention, in vitro cell cultures of disease-relevant cardiomyocytes are provided, where the cardiomyocytes are differentiated from induced human pluripotent stem cells (iPS cells) comprising at least one allele encoding a mutation associated with a cardiac disease. Mutations of interest include mutations in the genes: cardiac troponin T (TNNT2); myosin heavy chain (MYH7); tropomyosin 1 (TPM1); myosin binding protein C (MYBPC3); 5'-AMP-activated protein kinase subunit gamma-2 (PRKAG2); troponin I type 3 (TNNI3); titin (TTN); myosin, light chain 2 (MYL2); actin, alpha cardiac muscle 1 (ACTC1); potassium voltage-gated channel, KQT-like subfamily, member 1 (KCNQ1); plakophilin 2 (PKP2); and cardiac LIM protein (CSRP3). Specific mutations of interest include, without limitation, MYH7 R663H mutation; TNNT2 R173W; PKP2 2013delC mutation; PKP2 Q617X mutation; and KCNQ1 G269S missense mutation.

In some embodiments a panel of such cardiomyocytes are provided, where the panel includes two or more different disease-relevant cardiomyocytes. In some embodiments a panel of such cardiomyocytes are provided, where the cardiomyocytes are subjected to a plurality of candidate agents, or a plurality of doses of a candidate agent. Candidate agents include small molecules, i.e. drugs, genetic constructs that increase or decrease expression of an RNA of interest, electrical changes, and the like. In some embodiments the disease-relevant cardiomyocytes are introduced or induced to differentiate from iPS cells in an in vivo environment, for example as an explant in an animal model. In some embodiments a panel refers to a system or method utilizing patient-specific cardiomyocytes from two or more distinct cardiac conditions, and may be three or more, four or more, five or more, six or more, seven or more distinct conditions, where the conditions are selected from: dilated cardiomyopathy (DCM); hypertrophic cardiomyopathy (HCM); anthracycline-induced cardiotoxicity; arrhythmogenic right ventricular dysplasia (ARVD); left ventricular non-compaction (LVNC); double inlet left ventricle (DILV); and long QT (Type-1) syndrome (LOT-1).

In some embodiments of the invention, methods are provided for determining the activity of a candidate agent on a disease-relevant cardiomyocyte, the method comprising contacting the candidate agent with one or a panel of cardiomyocytes differentiated from induced human pluripotent stem cells (iPS cells) comprising at least one allele encoding a mutation associated with a cardiac disease; and determining the effect of the agent on morphologic, genetic or functional parameters, including without limitation calcium transient amplitude, intracellular $Ca^{2+}$ level, cell size contractile force production, beating rates, sarcomeric α-actinin distribution, and gene expression profiling. Methods of analysis at the single cell level are of particular interest, e.g. atomic force microscopy, microelectrode array recordings, patch clamping, single cell PCR, calcium imaging, and the like.

Where the disease is DCM, the cardiomyocytes may be stimulated with positive inotropic stress, such as a β-adrenergic agonist before, during or after contacting with the candidate agent. In some embodiments the β-adrenergic agonist is norepinephrine. It is shown herein that DMC cardiomyocytes have an initially positive chronotropic effect in response to positive inotropic stress, that later becomes negative with characteristics of failure such as reduced beating rates, compromised contraction, and significantly more cells with abnormal sarcomeric α-actinin distribution. β-adrenergic blocker treatment and over-expression of sarcoplasmic reticulum $Ca^{2+}$ ATPase (Serca2a) improve the function. DCM cardiomyocytes may also be tested with genetic agents in the pathways including factors promoting cardiogenesis, integrin and cytoskeletal signaling, and ubiquitination pathway, for example as shown in Table 8. Compared to the control healthy individuals in the same family cohort, DCM cardiomyocytes exhibit decreased calcium transient amplitude, decreased contractility, and abnormal sarcomeric α-actinin distribution.

Where the disease is HCM the cardiomyocytes may be stimulated with positive inotropic stress, such as a β-adrenergic agonist before, during or after contacting with the candidate agent. Under such conditions, HCM cardiomyocytes display higher hypertrophic responses, which can be reversed by a β-adrenergic blocker. Compared to healthy individuals, HCM cardiomyocytes exhibit increased cell size and up-regulation of HCM related genes, and more irregularity in contractions characterized by immature beats, including a higher frequency of abnormal $Ca^{2+}$ transients, characterized by secondary immature transients. These cardiomyocytes have increased intracullar $Ca^{2+}$ levels, and in some embodiments candidate agents that target calcineurin or other targets associated with calcium affinity.

Also provided are pluripotent stem cell populations comprising at least one allele encoding a mutation associated with a cardiac disease. Mutations of interest include mutations in the genes: cardiac troponin T (TNNT2); myosin heavy chain (MYH7); tropomyosin 1 (TPM1); myosin binding protein C (MYBPC3); 5'-AMP-activated protein kinase subunit gamma-2 (PRKAG2); troponin I type 3 (TNNI3); titin (TTN); myosin, light chain 2 (MYL2); actin, alpha cardiac muscle 1 (ACTC1); potassium voltage-gated channel, KQT-like subfamily, member 1 (KCNQ1); plakophilin 2 (PKP2); and cardiac LIM protein (CSRP3). Specific mutations of interest include, without limitation, MYH7 R663H mutation; TNNT2 R173W; PKP2 2013delC mutation; PKP2 Q617X mutation; and KCNQ1 G269S missense mutation. The pluripotent stem cell populations may be provided as a cell culture, optionally a feeder-layer free cell culture. Various somatic cells find use as a source of iPS cells; of particular interest are adipose-derived stem cells, fibroblasts, and the like. The pluripotent cells and cardiomyocytes derived therefrom may be used for transplantation, for experimental evaluation, as a source of lineage and cell specific products, and the like. These and other objects, advantages, and features of the invention will become apparent to those persons skilled in the art upon reading the details of the subject methods and compositions as more fully described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
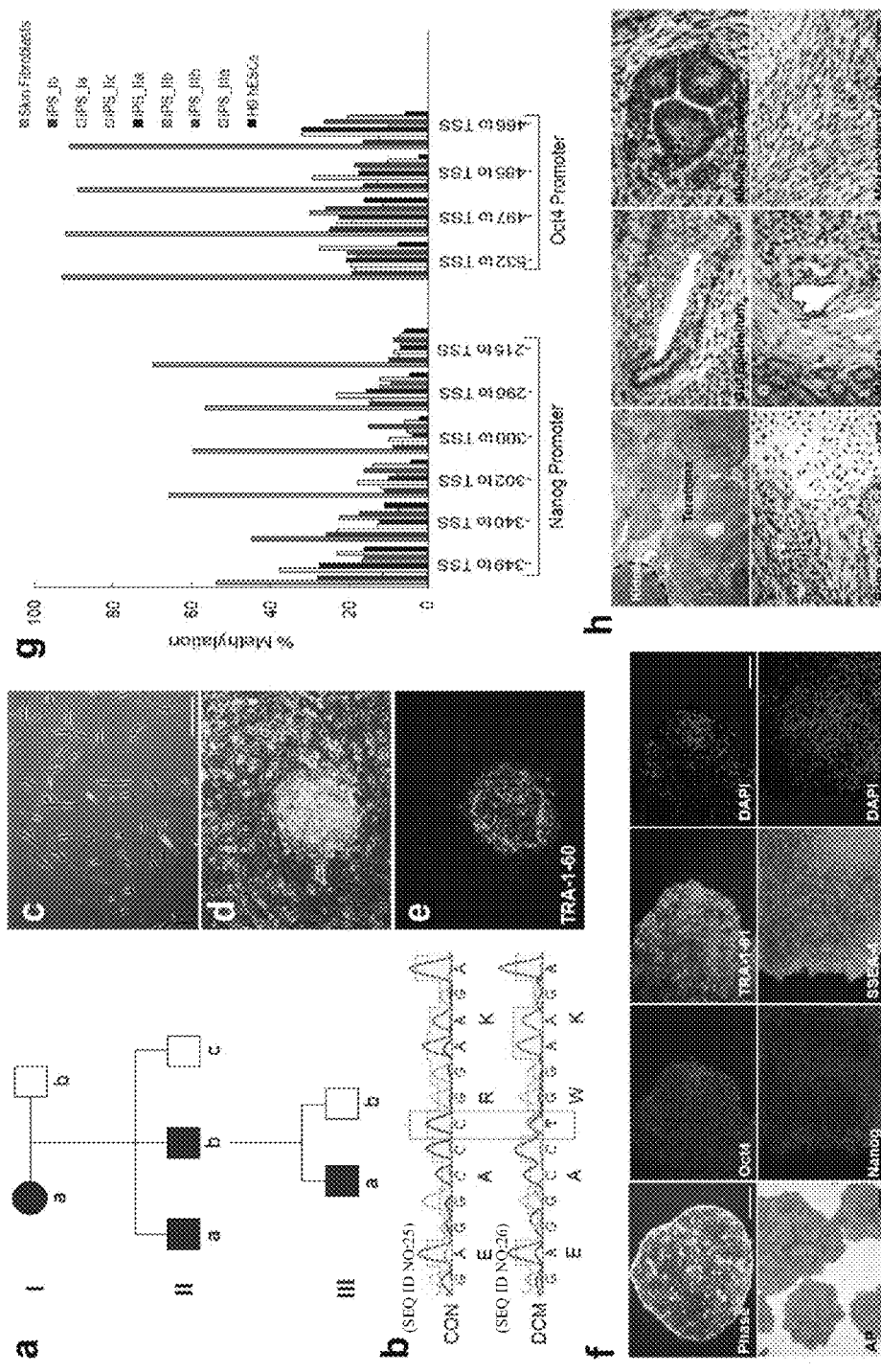
FIG. 1. Generation of patient-specific DCM iPSCs. (a) Schematic pedigree of the seven member DCM family recruited in this study. Filled squares (male) and circles (female) represent individuals carrying the specific TNNT2 R173W mutation on chromosome 1 in one of the two alleles. (b) The R173W point mutation was confirmed to be present on exon 12 of the TNNT2 gene in the DCM patients by PCR and DNA sequencing. CON, control. (c) A representative image of the patient-derived skin fibroblasts expanded from the skin biopsies. Representative images of an (d) ESC-like and (e) TRA-1-60 positive colony derived from reprogramming the patient-derived skin fibroblasts with Yamanaka factors. (f) Immunofluorescence and alkaline phosphatase staining of the patient skin fibroblasts-derived iPSCs. (g) Quantitative bisulphite pyrosequencing analysis of the methylation status at the promoter regions of Oct4 and Nanog in the patient-specific iPSCs. Both the Nanog and Oct4 promoter regions were highly demethylated in the patient-specific iPSCs. (h) Teratomas derived from the patient-specific iPSCs injected into the kidney capsule of immunodeficient mice showing tissues of all three embryonic germ layers. Bars, 200 µm.

The invention is best understood from the following detailed description when read in conjunction with the accompanying drawings.

DETAILED DESCRIPTION OF THE INVENTION

Before the present compositions and methods are described, it is to be understood that this invention is not limited to particular compositions and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a reprogramming factor polypeptide" includes a plurality of such polypeptides, and reference to "the induced pluripotent stem cells" includes reference to one or more induced pluripotent stem cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

Dilated cardiomyopathy (DCM) is one of the cardiomyopathies, a group of diseases that primarily affect the myocardium. In DCM a portion of the myocardium is dilated, often without any obvious cause. Left or right ventricular systolic pump function of the heart is impaired, leading to progressive cardiac enlargement and hypertrophy, a process called remodeling. Although in many cases no etiology is apparent, dilated cardiomyopathy can result from a variety of toxic, metabolic, or infectious agents. About 25-35% of patients have familial forms of the disease, with most mutations affecting genes encoding cytoskeletal proteins, while some affect other proteins involved in contraction. The disease is genetically heterogeneous, but the most common form of its transmission is an autosomal dominant pattern. Cytoskeletal proteins involved in DCM include cardiac troponin T (TNNT2), α-cardiac actin, desmin, and the nuclear lamins A and C, and various other contractile proteins.

Hypertrophic cardiomyopathy (HCM), is a condition in which sarcomeres replicate causing heart muscle cells to increase in size, which results in the thickening of the heart muscle. In addition, the normal alignment of muscle cells is disrupted, a phenomenon known as myocardial disarray. HCM also causes disruptions of the electrical functions of the heart. HCM is most commonly due to a mutation in one of 9 sarcomeric genes that results in a mutated protein in the sarcomere. Myosin heavy chain mutations are associated with development of familial hypertrophic cardiomyopathy. Hypertrophic cardiomyopathy is usually inherited as an autosomal dominant trait, which mutations reported in cardiac troponin T (TNNT2); myosin heavy chain (MYH7); tropomyosin 1 (TPM1); myosin binding protein C (MYBPC3); 5'-AMP-activated protein kinase subunit gamma-2 (PRKAG2); troponin I type 3 (TNNI3); titin (UN); myosin, light chain 2 (MYL2); actin, alpha cardiac muscle 1 (ACTC1); and cardiac LIM protein (CSRP3). An insertion/deletion polymorphism in the gene encoding for angiotensin converting enzyme (ACE) alters the clinical phenotype of the disease. The D/D (deletion/deletion) genotype of ACE is associated with more marked hypertrophy of the left ventricle and may be associated with higher risk of adverse outcomes.

Anthracycline-induced cardiotoxicity (and resistance to anthracycline-induced toxicity). Anthracyclines such as doxorubicin are frontline chemotherapeutic agents that are used to treat leukemias, Hodgkin's lymphoma, and solid tumors of the breast, bladder, stomach, lung, ovaries, thyroid, and muscle, among other organs. The primary side effect of anthracyclines is cardiotoxicity, which results in severe heart failure for many of the recipients receiving regimens utilizing this chemotherapeutic agent.

Arrhythmogenic right ventricular dysplasia (ARVD). ARVD is an autosomal dominant disease of cardiac desmosomes that results in arrhythmia of the right ventricle and sudden cardiac death. It is second only to hypertrophic cardiomyopathy as a leading cause for sudden cardiac death in the young.

Left Ventricular Non-Compaction (LVNC, aka non-compaction cardiomyopathy). LVNC is a hereditary cardiac disease which results from impaired development of the myocardium (heart muscle) during embryogenesis. Patients with mutations causing LVNC develop heart failure and abnormal cardiac electrophysiology early in life.

Double Inlet Left Ventricle (DILV). DILV is a congenital heart defect in which both the left and right atria feed into the left ventricle. As a result, children born with this defect only have one functional ventricular chamber, and trouble pumping oxygenated blood into the general circulation.

Long QT (Type-1) Syndrome (LOT-1, KCNQ1 mutation). Long QT syndrome (LOT) is a hereditary arrhythmic disease in which the QT phase of the electrocardiogram is prolonged, resulting in increased susceptibility for arrhythmia and sudden cardiac death. There are 13 known genes associated with LQT.

By "pluripotency" and pluripotent stem cells it is meant that such cells have the ability to differentiate into all types of cells in an organism. The term "induced pluripotent stem cell" encompasses pluripotent cells, that, like embryonic stem (ES) cells, can be cultured over a long period of time while maintaining the ability to differentiate into all types of cells in an organism, but that, unlike ES cells (which are derived from the inner cell mass of blastocysts), are derived from differentiated somatic cells, that is, cells that had a narrower, more defined potential and that in the absence of experimental manipulation could not give rise to all types of cells in the organism. iPS cells have an hESC-like morphology, growing as flat colonies with large nucleo-cytoplasmic ratios, defined borders and prominent nuclei. In addition, iPS cells express one or more key pluripotency markers known by one of ordinary skill in the art, including but not limited to alkaline phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the iPS cells are capable of forming teratomas. In addition, they are capable of forming or contributing to ectoderm, mesoderm, or endoderm tissues in a living organism.

As used herein, "reprogramming factors" refers to one or more, i.e. a cocktail, of biologically active factors that act on a cell to alter transcription, thereby reprogramming a cell to multipotency or to pluripotency. Reprogramming factors may be provided to the cells, e.g. cells from an individual with a family history or genetic make-up of interest for heart disease such as fibroblasts, adipocytes, etc.; individually or as a single composition, that is, as a premixed composition, of reprogramming factors. The factors may be provided at the same molar ratio or at different molar ratios. The factors may be provided once or multiple times in the course of culturing the cells of the subject invention. In some embodiments the reprogramming factor is a transcription factor, including without limitation, Oct3/4; Sox2; Klf4; c-Myc; Nanog; and Lin-28.

Somatic cells are contacted with reprogramming factors, as defined above, in a combination and quantity sufficient to reprogram the cell to pluripotency. Reprogramming factors may be provided to the somatic cells individually or as a single composition, that is, as a premixed composition, of reprogramming factors. In some embodiments the reprogramming factors are provided as a plurality of coding sequences on a vector.

Genes may be introduced into the somatic cells or the iPS cells derived therefrom for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

The iPS cells may also be differentiated into cardiac muscle cells. Inhibition of bone morphogenetic protein (BMP) signaling may result in the generation of cardiac muscle cells (or cardiomyocytes), see, e.g., Yuasa et al., (2005), Nat. Biotechnol., 23(5):607-11. Thus, in an exemplary embodiment, the induced cells are cultured in the presence of noggin for from about two to about six days, e.g., about 2, about 3, about 4, about 5, or about 6 days, prior to allowing formation of an embryoid body, and culturing the embryoid body for from about 1 week to about 4 weeks, e.g., about 1, about 2, about 3, or about 4 weeks.

Cardiomyocyte differentiation may be promoted by including cardiotropic agents in the culture, such as activin A and/or bone morphogenetic protein-4 (see the Examples herein, Xu et al. Regen Med. 2011 January; 6(1):53-66; Mignone et al. Circ J. 2010 74(12):2517-26; Takei et al. Am J Physiol Heart Circ Physiol. 2009 296(6):H1793-803, each herein specifically incorporated by reference). Examples of such protocols also include, for example, addition of a Wnt agonist, such as Wnt 3A, optionally in the presence of cytokines such as BMP4, VEGF and Activin A; followed by culture in the presence of a Wnt antagonist, such a soluble frizzled protein. However, any suitable method of inducing cardiomyocyte differentiation may be used, for example, Cyclosporin A described by Fujiwara et al. PLoS One. 2011 6(2):e16734; Dambrot et al. Biochem J. 2011 434(1):25-35; equiaxial cyclic stretch, angiotensin II, and phenylephrine (PE) described by Foldes et al. J Mol Cell Cardiol. 2011 50(2):367-76; ascorbic acid, dimethylsulfoxide and 5-aza-2'-deoxycytidine described by Wang et al. Sci China Life Sci. 2010 53(5):581-9, endothelial cells described by Chen et al. J Cell Biochem. 2010 111 (1):29-39, and the like, which are herein specifically incorporated by reference.

The cells are harvested at an appropriate stage of development, which may be determined based on the expression of markers and phenotypic characteristics of the desired cell type e.g. at from about 1 to 4 weeks. Cultures may be empirically tested by staining for the presence of the markers of interest, by morphological determination, etc. The cells are optionally enriched before or after the positive selection step by drug selection, panning, density gradient centrifugation, etc. In another embodiment, a negative selection is performed, where the selection is based on expression of one or more of markers found on ES cells, fibroblasts, epithelial cells, and the like. Selection may utilize panning methods, magnetic particle selection, particle sorter selection, and the like.

Cardiomyocytes.

Phenotypes of cardiomyocytes that arise during development of the mammalian heart can be distinguished: primary cardiomyocytes; nodal cardiomyocytes; conducting cardiomyocytes and working cardiomyocytes. All cardiomyocytes have sarcomeres and a sarcoplasmic reticulum (SR), are coupled by gap junctions, and display automaticity. Cells of the primary heart tube are characterized by high automaticity, low conduction velocity, low contractility, and low SR activity. This phenotype largely persists in nodal cells. In contrast, atrial and ventricular working myocardial cells display virtually no automaticity, are well coupled intercellularly, have well developed sarcomeres, and have a high SR activity. Conducting cells from the atrioventricular bundle, bundle branches and peripheral ventricular conduction system have poorly developed sarcomeres, low SR activity, but are well coupled and display high automaticity.

For α-Mhc, β-Mhc and cardiac Troponin I and slow skeletal Troponin I, developmental transitions have been observed in differentiated ES cell cultures. Expression of Mlc2v and Anf is often used to demarcate ventricular-like and atrial-like cells in ES cell cultures, respectively, although in ESDCs, Anf expression does not exclusively identify atrial cardiomyocytes and may be a general marker of the working myocardial cells.

A "cardiomyocyte precursor" is defined as a cell that is capable of giving rise to progeny that include cardiomyocytes.

In addition to various uses as an in vitro cultured cells, the cardiomyocytes may be tested in a suitable animal model. At one level, cells are assessed for their ability to survive and maintain their phenotype in vivo. Cell compositions are administered to immunodeficient animals (such as nude mice, or animals rendered immunodeficient chemically or by irradiation). Tissues are harvested after a period of regrowth, and assessed as to whether the administered cells or progeny thereof are still present, and may be phenotyped for response to a treatment of interest. Suitability can also be determined in an animal model by assessing the degree of cardiac recuperation that ensues from treatment with the differentiating cells of the invention. A number of animal models are available for such testing. For example, hearts can be cryoinjured by placing a precooled aluminum rod in contact with the surface of the anterior left ventricle wall (Murry et al., J. Clin. Invest. 98:2209, 1996; Reinecke et al., Circulation 100:193, 1999; U.S. Pat. No. 6,099,832). In larger animals, cryoinjury can be inflicted by placing a 30-50 mm copper disk probe cooled in liquid $N_2$ on the anterior wall of the left ventricle for approximately 20 min (Chiu et al., Ann. Thorac. Surg. 60:12, 1995). Infarction can be induced by ligating the left main coronary artery (Li et al., J. Clin. Invest. 100:1991, 1997). Injured sites are treated with cell preparations of this invention, and the heart tissue is examined by histology for the presence of the cells in the damaged area. Cardiac function can be monitored by determining such parameters as left ventricular end-diastolic pressure, developed pressure, rate of pressure rise, rate of pressure decay, etc.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," are used interchangeably herein and refer to any mammalian subject for whom diagnosis, treatment, or therapy is desired, particularly humans.

METHODS OF THE INVENTION

Methods are provided for the obtention and use of in vitro cell cultures of disease-relevant cardiomyocytes, where the cardiomyocytes are differentiated from induced human pluripotent stem cells (iPS cells) comprising at least one allele encoding a mutation associated with a cardiac disease, as described above. Specific mutations of interest include, without limitation, MYH7 R663H mutation, TNNT2 R173W; PKP2 2013delC mutation; PKP2 Q617X mutation; and KCNQ1 G269S missense mutation. In some embodiments a panel of such cardiomyocytes are provided, where the panel includes two or more different disease-relevant cardiomyocytes. In some embodiments a panel of such cardiomyocytes are provided, where the cardiomyocytes are subjected to a plurality of candidate agents, or a plurality of doses of a candidate agent. Candidate agents include small molecules, i.e. drugs, genetic constructs that increase or decrease expression of an RNA of interest, electrical changes, and the like.

Methods are provided for determining the activity of a candidate agent on a disease-relevant cardiomyocyte, the method comprising contacting the candidate agent with one or a panel of cardiomyocytes differentiated from induced human pluripotent stem cells (iPS cells) comprising at least one allele encoding a mutation associated with a cardiac disease; and determining the effect of the agent on morphologic, genetic or functional parameters, including without limitation calcium transient amplitude, intracellular $Ca^{2+}$ level, cell size contractile force production, beating rates, sarcomeric α-actinin distribution, and gene expression profiling.

Where the disease is DCM, the cardiomyocytes may be stimulated with positive inotropic stress, such as a β-adrenergic agonist before, during or after contacting with the candidate agent. In some embodiments the β-adrenergic agonist is norepinephrine. It is shown herein that DMC cardiomyocytes have an initially positive chronotropic effect in response to positive inotropic stress, that later becomes negative with characteristics of failure such as reduced beating rates, compromised contraction, and significantly more cells with abnormal sarcomeric α-actinin distribution. β-adrenergic blocker treatment and over-expression of sarcoplasmic reticulum $Ca^{2+}$ ATPase (Serca2a) improve the function. DCM cardiomyocytes may also be tested with genetic agents in the pathways including factors promoting cardiogenesis, integrin and cytoskeletal signaling, and ubiquitination pathway, for example as shown in Table 8. Compared to the control healthy individuals in the same family cohort, DCM cardiomyocytes exhibit decreased calcium transient amplitude, decreased contractility, and abnormal sarcomeric α-actinin distribution.

Where the disease is HCM the cardiomyocytes may be stimulated with positive inotropic stress, such as a β-adrenergic agonist before, during or after contacting with the candidate agent. Under such conditions, HCM cardiomyocytes display higher hypertrophic responses, which can be reversed by a β-adrenergic blocker. Compared to healthy individuals, HCM cardiomyocytes exhibit increased cell size and up-regulation of HCM related genes, and more irregularity in contractions characterized by immature beats, including a higher frequency of abnormal $Ca^{2+}$ transients, characterized by secondary immature transients. These cardiomyocytes have increased intracullar $Ca^{2+}$ levels, and in some embodiments candidate agents that target calcineurin or other targets associated with calcium affinity.

In screening assays for the small molecules, the effect of adding a candidate agent to cells in culture is tested with a panel of cells and cellular environments, where the cellular environment includes one or more of: electrical stimulation including alterations in ionicity, drug stimulation, and the like, and where panels of cells may vary in genotype, in prior exposure to an environment of interest, in the dose of agent that is provided, etc., where usually at least one control is included, for example a negative control and a positive control. Culture of cells is typically performed in a sterile environment, for example at 37° C. in an incubator containing a humidified 92-95% air/5-8% $CO_2$ atmosphere. Cell culture may be carried out in nutrient mixtures containing undefined biological fluids such as fetal calf serum, or media which is fully defined and serum free. The effect of the altering of the environment is assessed by monitoring multiple output parameters, including morphological, functional and genetic changes.

In the screening assays for genetic agents, polynucleotides are added to one or more of the cells in a panel in order to alter the genetic composition of the cell. The output parameters are monitored to determine whether there is a change in phenotype. In this way, genetic sequences are identified that encode or affect expression of proteins in pathways of interest. The results can be entered into a data processor to provide a screening results dataset. Algorithms are used for the comparison and analysis of screening results obtained under different conditions.

Methods for analysis include calcium imaging, where cells are loaded with an appropriate dye and exposed to calcium in a condition of interest, and imaged, for example with a confocal microscope. $Ca^{2+}$ responses may be quantified, and the time-dependent $Ca^{2+}$ response was then analyzed for irregularities in timing of successive $Ca^{2+}$ transients and for the total $Ca^{2+}$ influx per transient. The total $Ca^{2+}$ released during each transient was determined by integrating the area underneath each wave with respect to the baseline.

Atomic force microscopy (AFM) can be used to measure contractile forces. Beating cells are interrogated by AFM using a cantilever. To measure forces, cells are gently contacted by the cantilever tip, then the cantilever tip remains in the position for intervals while deflection data are collected. Statistics can be calculated for the forces, intervals between beats, and duration of each contraction for each cell.

Cells can also analyzed by microelectrode array (MEA), where beating cardiomyocytes are plated on MEA probes, and the field potential duration (FPD) measured and determined to provide electrophysiological parameters.

Methods of analysis at the single cell level are of particular interest, e.g. as described) above: atomic force microscopy, microelectrode array recordings, patch clamping, single cell PCR, calcium imaging, flow cytometry and the like.

Parameters are quantifiable components of cells, particularly components that can be accurately measured, desirably in a high throughput system. A parameter can also be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Variability is expected and a range of values for each of the set of test parameters will be obtained using standard statistical methods with a common statistical method used to provide single values.

Parameters of interest include detection of cytoplasmic, cell surface or secreted biomolecules, frequently biopolymers, e.g. polypeptides, polysaccharides, polynucleotides, lipids, etc. Cell surface and secreted molecules are a preferred parameter type as these mediate cell communication and cell effector responses and can be more readily assayed. In one embodiment, parameters include specific epitopes. Epitopes are frequently identified using specific monoclonal antibodies or receptor probes. In some cases the molecular entities comprising the epitope are from two or more substances and comprise a defined structure; examples include combinatorially determined epitopes associated with heterodimeric integrins. A parameter may be detection of a specifically modified protein or oligosaccharide. A parameter may be defined by a specific monoclonal antibody or a ligand or receptor binding determinant.

Candidate agents of interest are biologically active agents that encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Cardiovascular Drugs; Vitamins, Dermatology; and Toxicology, all incorporated herein by reference.

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As used herein, the term "genetic agent" refers to polynucleotides and analogs thereof, which agents are tested in the screening assays of the invention by addition of the genetic agent to a cell. The introduction of the genetic agent results in an alteration of the total genetic composition of the cell. Genetic agents such as DNA can result in an experimentally introduced change in the genome of a cell, generally through the integration of the sequence into a chromosome. Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of mRNA. The effect of a genetic agent is to increase or decrease expression of one or more gene products in the cell.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; RNAi, encode a dominant negative mutation, or dominant or constitutively active mutations of native sequences; altered regulatory sequences, etc.

Antisense and RNAi oligonucleotides can be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity, e.g. morpholino oligonucleotide analogs. The □-anomer of deoxyribose may be used, where the base is inverted with respect to the natural □-anomer. The 2'-OH of the ribose sugar may be altered to form 2'-O-methyl or 2'-O-allyl sugars, which provides resistance to degradation without comprising affinity.

Agents are screened for biological activity by adding the agent to at least one and usually a plurality of cells, in one or in a plurality of environmental conditions, e.g. following stimulation with a β-adrenergic agonist, following electric or mechanical stimulation, etc. The change in parameter readout in response to the agent is measured, desirably normalized, and the resulting screening results may then be evaluated by comparison to reference screening results, e.g. with cells having other mutations of interest, normal cardiomyocytes, cardiomyocytes derived from other family members, and the like. The reference screening results may include readouts in the presence and absence of different environmental changes, screening results obtained with other agents, which may or may not include known drugs, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of selected parameters, in addition to the functional parameters described above. For measuring the amount of a molecule that is present, a convenient method is to label a molecule with a detectable moiety, which may be fluorescent, luminescent, radioactive, enzymatically active, etc., particularly a molecule specific for binding to the parameter with high affinity Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting. These techniques are particularly useful for protein or modified protein parameters or epitopes, or carbohydrate determinants. Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected cell surface molecules or cytokines, or the average fluorescence intensity, the median fluorescence intensity, the variance in fluorescence intensity, or some relationship among these.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112-225; Kawamoto et al. (1999) Genome Res 9(12):1305-12; and Chen et al. (1998) Genomics 51(3):313-24, for examples.

The comparison of a screening results obtained from a test compound, and a reference screening results(s) is accomplished by the use of suitable deduction protocols, AI systems, statistical comparisons, etc. Preferably, the screening results is compared with a database of reference screening results. A database of reference screening results can be compiled. These databases may include reference results from panels that include known agents or combinations of agents, as well as references from the analysis of cells treated under environmental conditions in which single or multiple environmental conditions or parameters are removed or specifically altered. Reference results may also be generated from panels containing cells with genetic constructs that selectively target or modulate specific cellular pathways.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

For convenience, the systems of the subject invention may be provided in kits. The kits could include the cells to be used, which may be frozen, refrigerated or treated in some other manner to maintain viability, reagents for measuring the parameters, and software for preparing the screening results. The software will receive the results and perform analysis and can include reference data. The software can also normalize the results with the results from a control culture. The composition may optionally be packaged in a suitable container with written instructions for a desired purpose, such as screening methods, and the like.

For further elaboration of general techniques useful in the practice of this invention, the practitioner can refer to standard textbooks and reviews in cell biology, tissue culture, embryology, and cardiophysiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998). With respect to the culture of heart cells, standard references include The Heart Cell in Culture (A. Pinson ed., CRC Press 1987), Isolated Adult Cardiomyocytes (Vols. I & II, Piper & Isenberg eds, CRC Press 1989), Heart Development (Harvey & Rosenthal, Academic Press 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Example 1

Dilated cardiomyopathy (DCM) is the most common cardiomyopathy, characterized by ventricular dilatation, systolic dysfunction, and progressive heart failure. DCM is the most common diagnosis leading to heart transplantation and places a considerable burden on healthcare worldwide. Here we generated cardiomyocytes (CMs) from iPSCs derived from patients of a DCM family carrying a point mutation (R173W) in the gene that encodes sarcomeric protein cardiac troponin T. Compared to the control healthy individuals in the same family cohort, DCM iPSC-CMs exhibited decreased calcium transient amplitude, decreased contractility, and abnormal sarcomeric α-actinin distribution. When stimulated with β-adrenergic agonist, DCM iPSC-CMs showed characteristics of failure such as reduced beating rates, compromised contraction, and significantly more cells with abnormal sarcomeric α-actinin distribution. β-adrenergic blocker treatment and over-expression of sarcoplasmic reticulum $Ca^{2+}$ ATPase (Serca2a) improved the function of DCM iPSC-CMs. Our study demonstrated that human DCM iPSC-CMs recapitulated the disease phenotypes morphologically and functionally, and thus can serve as a useful platform for exploring molecular and cellular mechanisms and optimizing treatment of this particular disease.

We recruited a cohort of seven individuals from a DCM proband carrying an autosomal dominant point mutation on exon 12 of the gene TNNT2, which causes an Arginine (R) to Tryptophan (W) mutation at amino acid position 173 in the protein cTnT. The causal effect for DCM of this particular point mutation was confirmed by genetic screening of a panel of 17 primary DCM associated genes (Table 1) and genetic co-segregation studies (Table 2). This mutation was also reported in a completely independent Belgian family. The seven recruited individuals covered 3 generations (I, II, and III) (FIG. 1a). Four patients (Ia, IIa, IIb, and IIIa) were confirmed to carry the TNNT2 R173W mutation in one of the two alleles by PCR amplifying the genomic locus of TNNT2 and DNA sequencing, while the other 3 individuals (Ib, IIc, and IIIb) were confirmed normal and served as controls in the subsequent studies (FIG. 1b). All four patients who carry the specific R173W mutation manifested clinical DCM symptoms with dilated left ventricle and decreased ejection fraction, and were treated medically (Table 2). A 14-year-old diseased patient (IIIa) had an orthotopic heart transplant due to severe clinical symptoms. Further genetic screening by exome sequencing of this particular patient IIIa with a panel of 32 most updated DCM-associated genes did not find any other additional variants that associate with the disease (Table 3).

Figure 5:
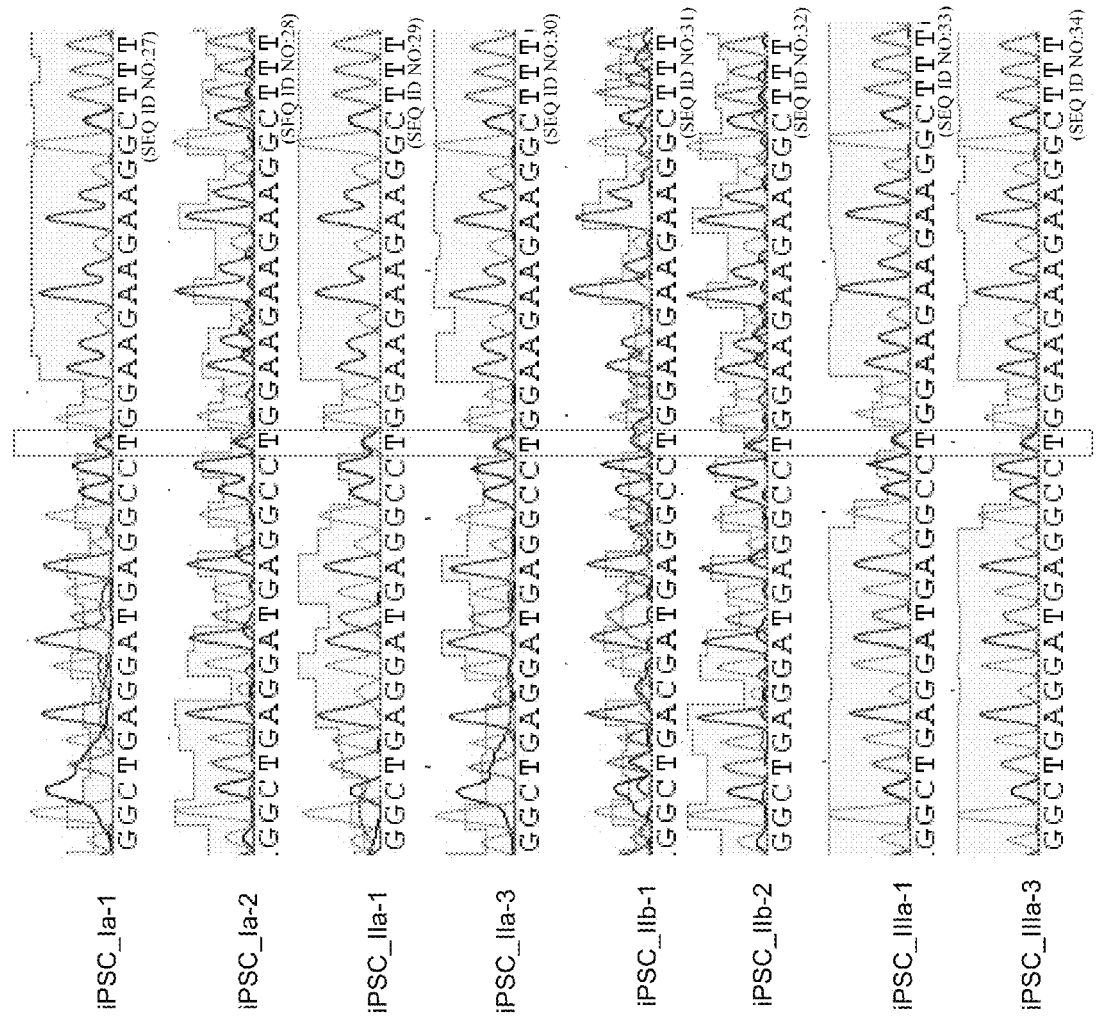
FIG. 5. R173W mutation in the iPSCs derived from DCM patients in the family. Genomic PCR of the locus of TNNT2 and DNA sequencing indicate that iPSCs from all DCM patients carried the R173W (C to T) mutation.
Figure 6:
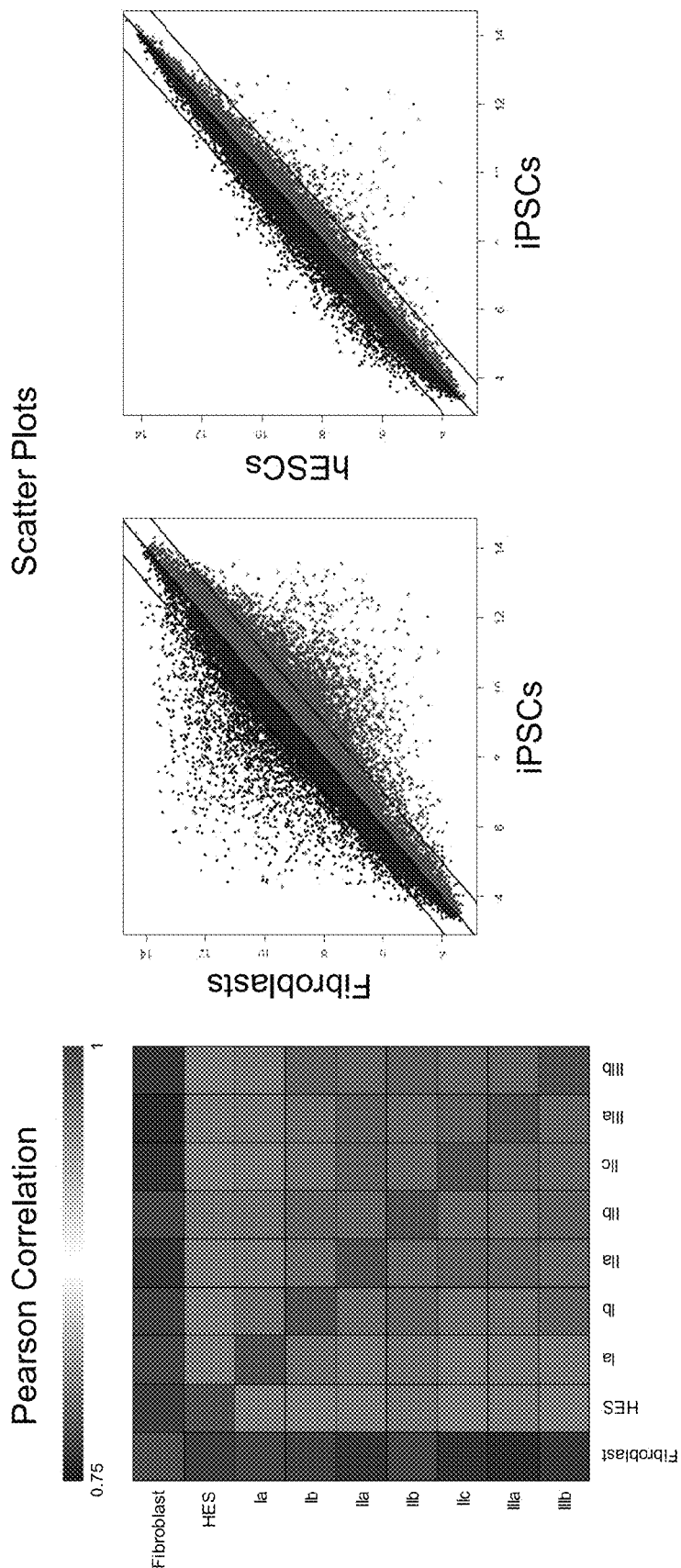
FIG. 6. Comparison of the global mRNA expression patterns of human ESCs (H7), skin fibroblasts, and patient-specific iPSCs by microarray. Both Pearson correlation and scatter plots indicate that the global gene expression pattern of patient-specific iPSCs was highly similar to that of human ESCs.
Figure 7:
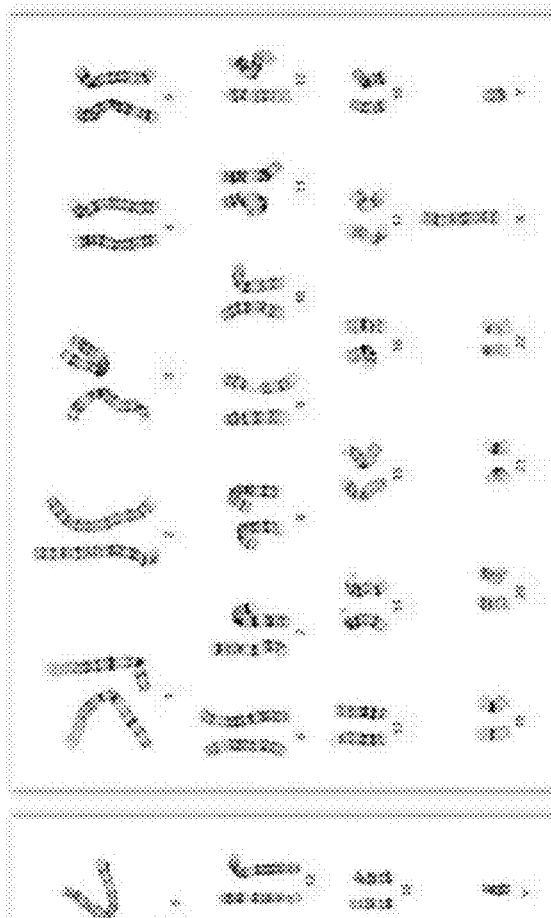
FIG. 7. Patient-specific iPSCs maintained normal karyotype after extended culture. Representative images from two DCM iPSC lines were shown after culturing for 20 passages.
Figure 7:
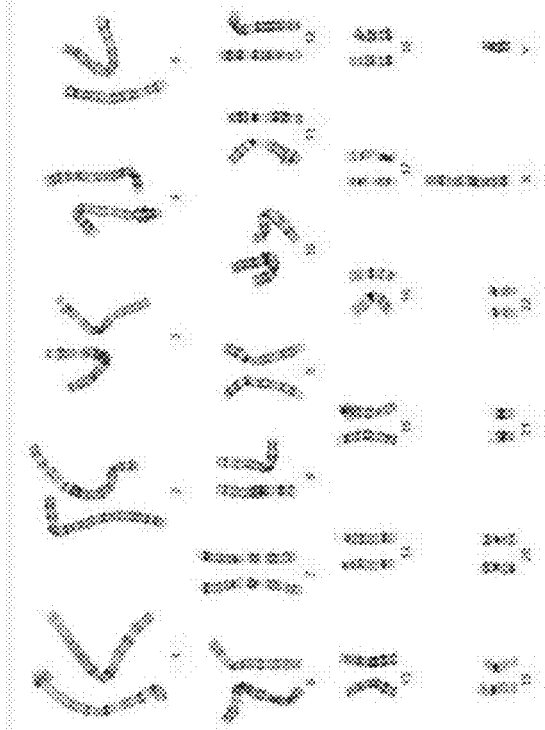
Figure 8:
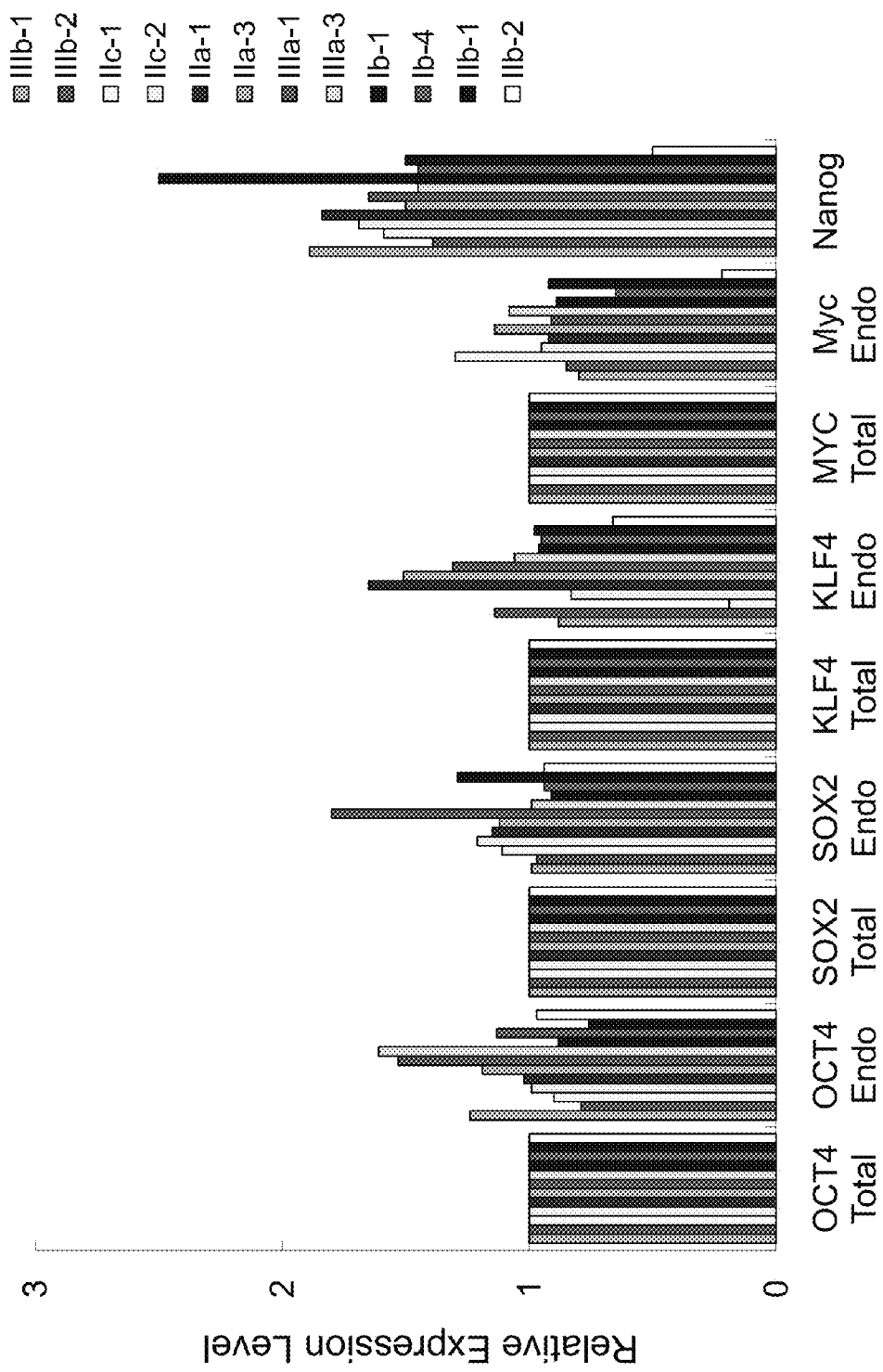
FIG. 8. Quantitative-PCR of relative expression levels of total versus endogenous Yamanaka reprogramming factors. By comparing the total and endogenous gene expression level of each reprogramming factor, exogenous transgenes Oct4, Sox2, Klf 4, and c-MYC were silenced in most of the established patient-specific iPSCs. Endogenous Nanog expression was up-regulated in all the patient-specific iPSCs, indicating a pluripotency state of each cell line. Note that the Nanog expression levels were normalized to that of the H7 human ESCs (not shown). Primer information used for quantitative PCR are listed in Supplementary Table 6.
Figure 9:
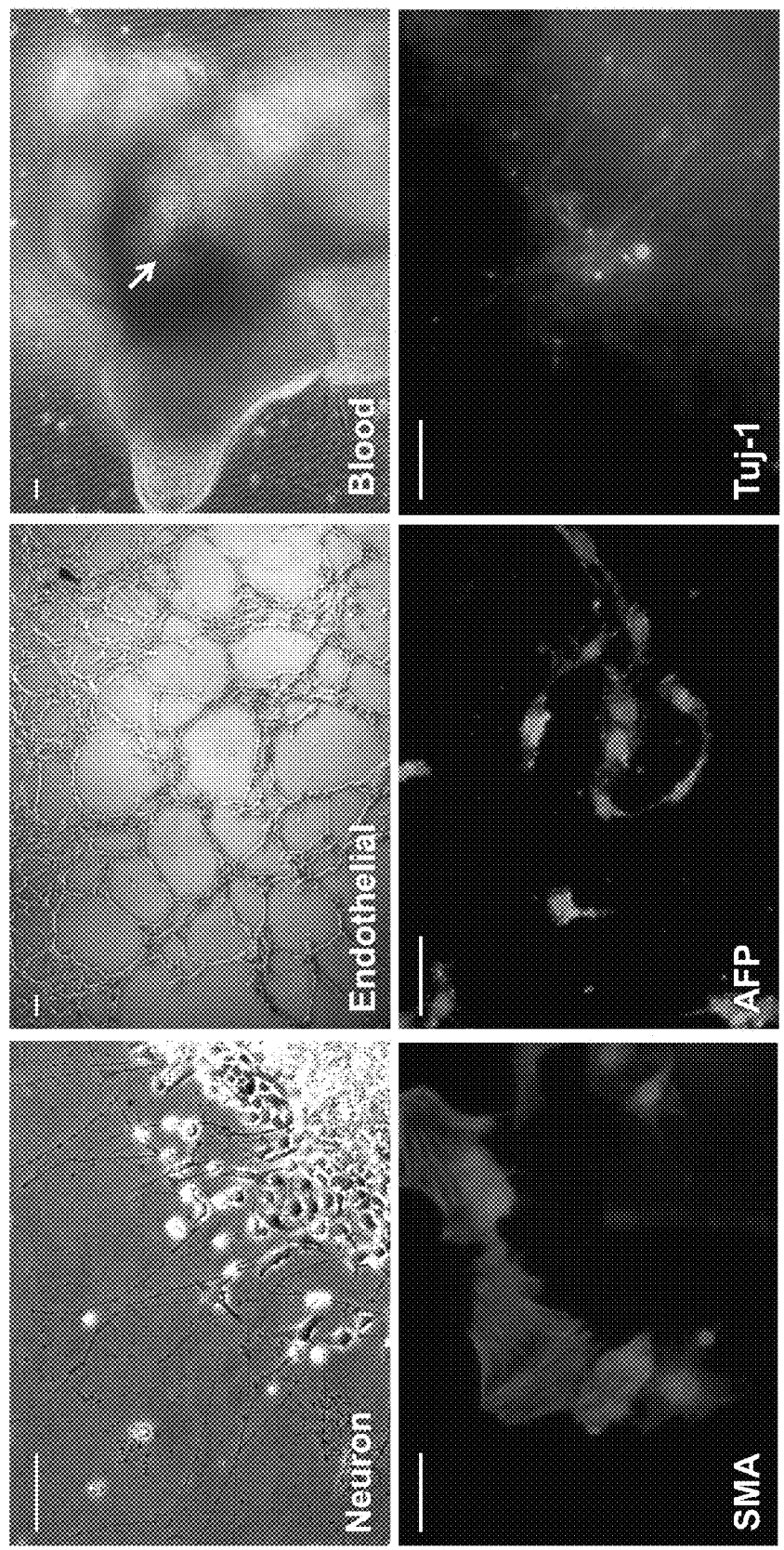
FIG. 9. Patient-specific iPSCs can differentiate into cells from the 3 germ layers in vitro. Different cell types, such as neurons, endothelial cells, red blood cells, as well as cells expressing mesoderm marker smooth muscle actin (SMA), endoderm marker α-fetoprotein (AFP), and ectoderm marker (Tuj-1) were detected from spontaneous differentiation of all the patient-specific iPSCs. Bars, 100 μm.

To generate patient-specific iPSCs for the seven individuals, skin fibroblasts were expanded from skin biopsies taken from each individual (FIG. 1c) and reprogrammed with lentiviral Yamanaka 4 factors (Oct4, Sox2, Klf4, and c-MYC) under feeder-free condition. Colonies with TRA-1-60+ staining and human embryonic stem cell (hESC)-like morphology (FIGS. 1d and 1e) were picked, expanded, and established as individual iPSC lines. For each individual, 3-4 iPSC lines were established for subsequent analyses. All of the DCM iPSC lines were confirmed to contain the specific R173W mutation by genomic PCR and DNA sequencing (FIG. 5). All established iPSC lines expressed the pluripotency markers Oct4, Nanog, TRA-1-81, and SSEA-4, and were positive for alkaline phosphatase (FIG. 1f). Microarray analyses indicated these iPSC lines were distinct from the parental skin fibroblasts, expressing a global gene pattern more similar to hESCs (FIG. 6). Quantitative bisulphite sequencing showed that the promoter regions of Oct4 and Nanog were hypomethylated in all the tested iPSC lines, indicating active transcription of the pluripotency genes (FIG. 1g). The established iPSC lines maintained a normal karyotype after extended passage (FIG. 7) and the majority of them exhibited silencing of exogenous transgenes and re-expression of endogenous Nanog (FIG. 8). iPSC lines with incomplete transgene silencing were removed from the subsequent studies. These patient-specific iPSCs were able to differentiate in vitro into cells of all three germ layers (FIG. 9) and form teratomas following injection into the kidney capsules of immunodeficient mice (FIG. 1h).

Figure 10:
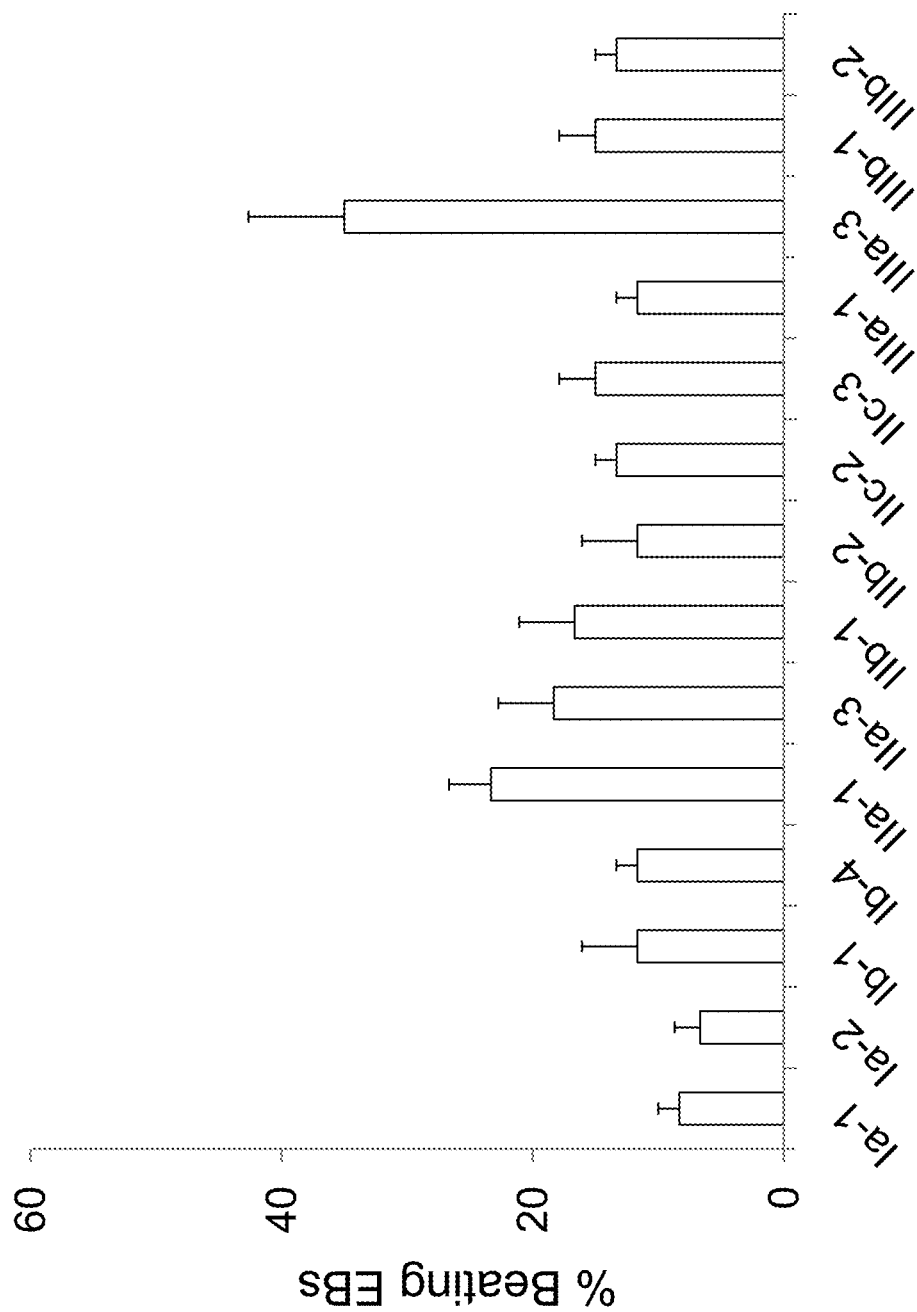
FIG. 10. Relative cardiac differentiation efficiency of the patient-specific iPSCs. The cardiac differentiation efficiency is represented as percentage of beating EBs (n=3 for each line, data are presented as mean±s.e.m).
Figure 11:
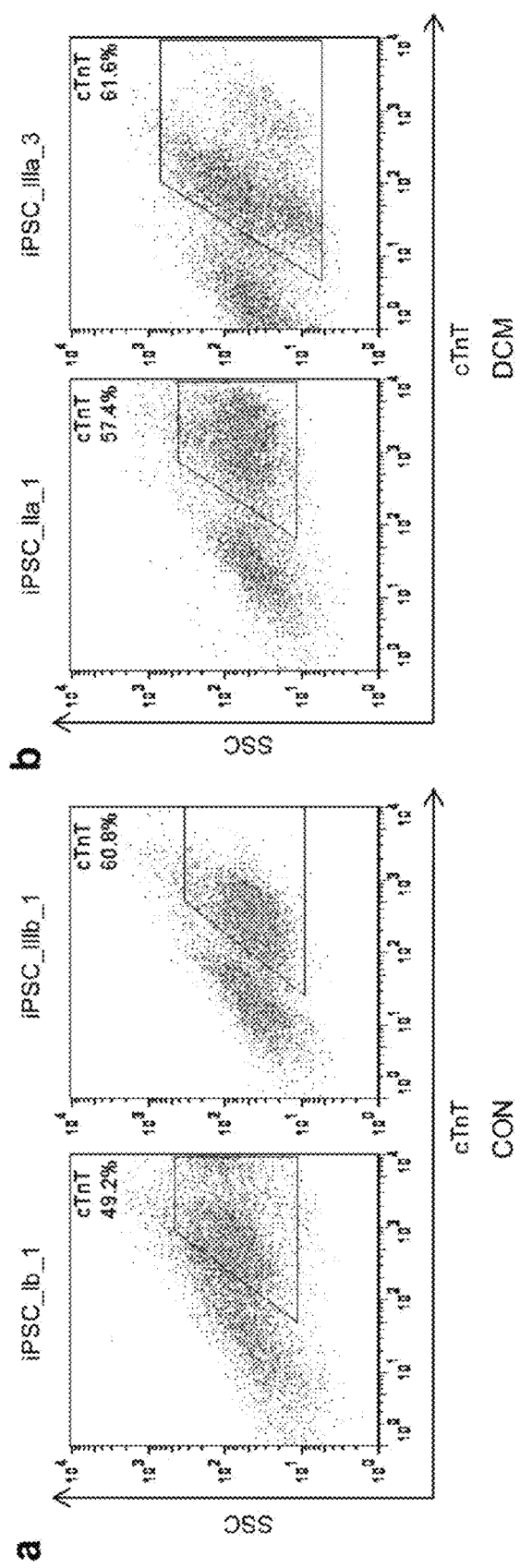
FIG. 11. FACS analysis of percentage of cTnT positive CMs within beating EBs derived from control and DCM iPSCs. ~50-60% cells in beating EBs were cTnT positive cardiomyocytes.
Figure 12:
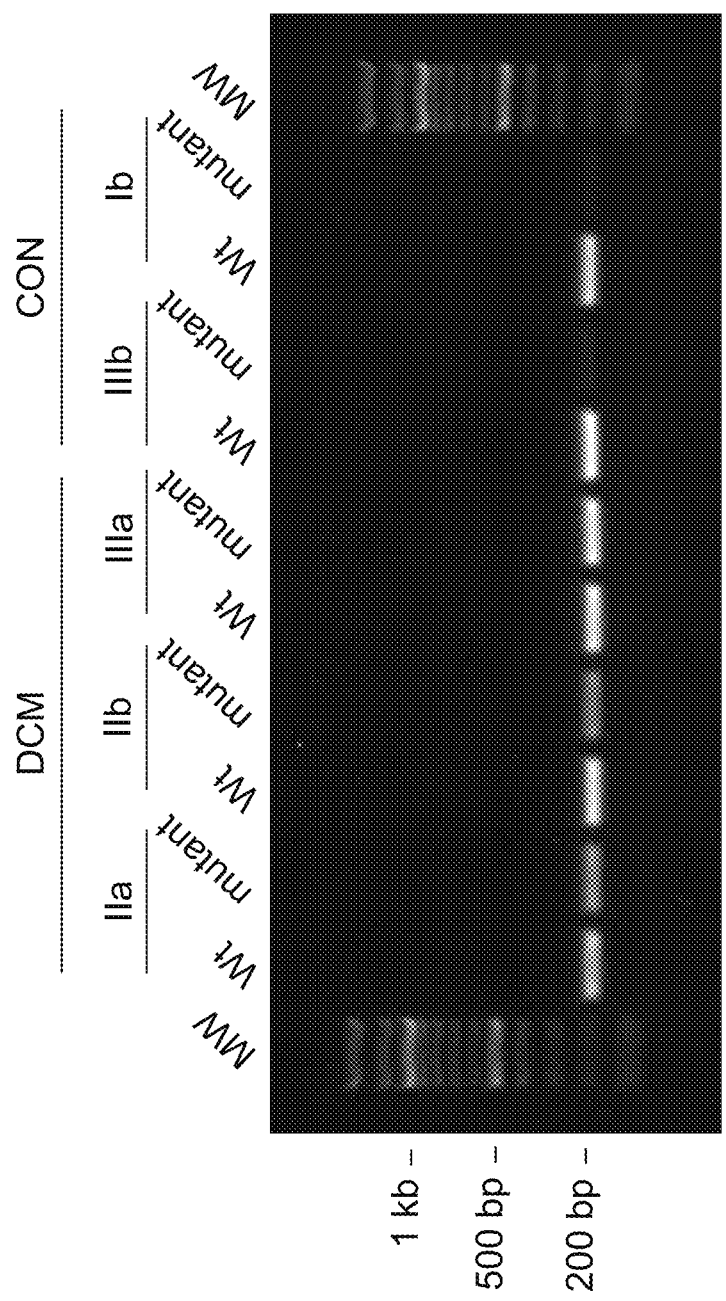
FIG. 12. Allele-specific PCR of wild type (Wt) and mutant (R173W) TNNT2 expression in DCM and control iPSC-CMs. Patient IIa, IIb, and IIIa were confirmed to express the mutant TNNT2 in their respective iPSC-derived CMs. The primers used for allelic PCR are listed in Supplementary Table 6.
Figure 13:
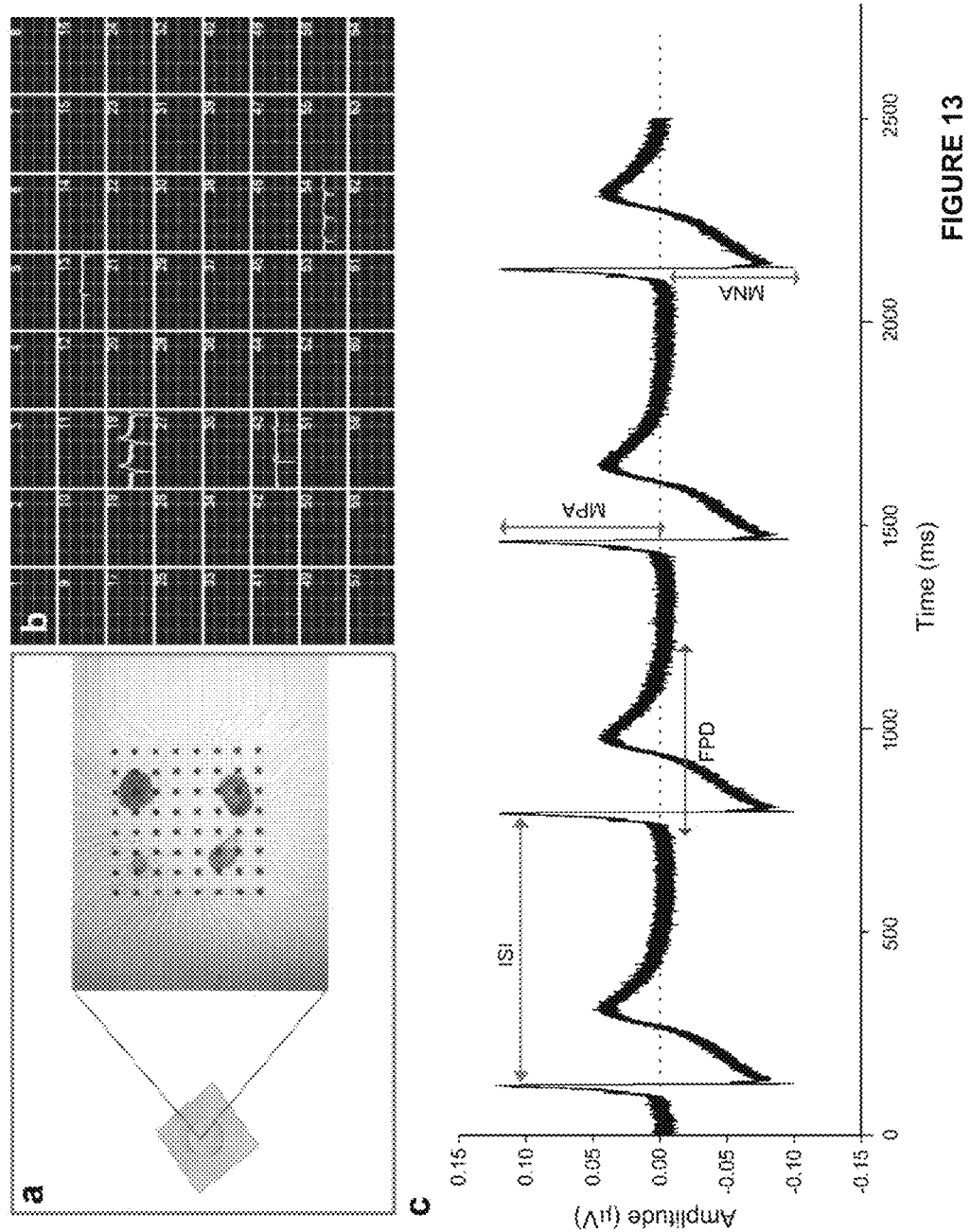
FIG. 13. Multi-electrode arrays (MEA) examining electrophysiologic properties of iPSC-derived beating EBs. (a) The MEA probe and a representative image of 4 beating EBs seeded. (b) The electrical signals recorded by MEA reflecting field potentials of the 4 beating EBs shown in (a). (c) Extracted MEA field potential graphs showing field potential duration (FPD), maximum positive amplitude (MPA), maximum negative amplitude (MNA), and interspike interval (ISI).

We next differentiated the DCM iPSCs into the cardiovascular lineage using a well-established 3D differentiation protocol developed by Yang, L., et al. Human cardiovascular progenitor cells develop from a KDR+ embryonic-stem-cell-derived population. *Nature* 453, 524-528 (2008). Two iPSC lines from each individual were selected to be differentiated into spontaneous beating embryoid bodies (EBs). Spontaneous beating was observed as early as day 8 post differentiation. The efficiency of differentiation to cardiac lineage varied among different lines (FIG. 10). Beating EBs derived from control and patient iPSCs contained approximately 50-60% cTnT positive CMs (FIG. 11). Allele-specific PCR of beating EBs derived from three iPSC clones of 3 DCM patients indicated bi-allelic expression of the wild type and mutant (R173W) TNNT2 gene (FIG. 12). The beating EBs from the control iPSCs and DCM iPSCs were seeded on multi-electrode array (MEA) probe (FIG. 13a) and their electrophysiological properties recorded (FIG. 13b). Both control (n=45) and DCM (n=57) iPSC-derived beating EBs exhibited comparable beat frequencies, field potentials, interspike intervals, and field potential durations (FPD) at baseline (Table 4 and FIG. 13c).

Figure 2:
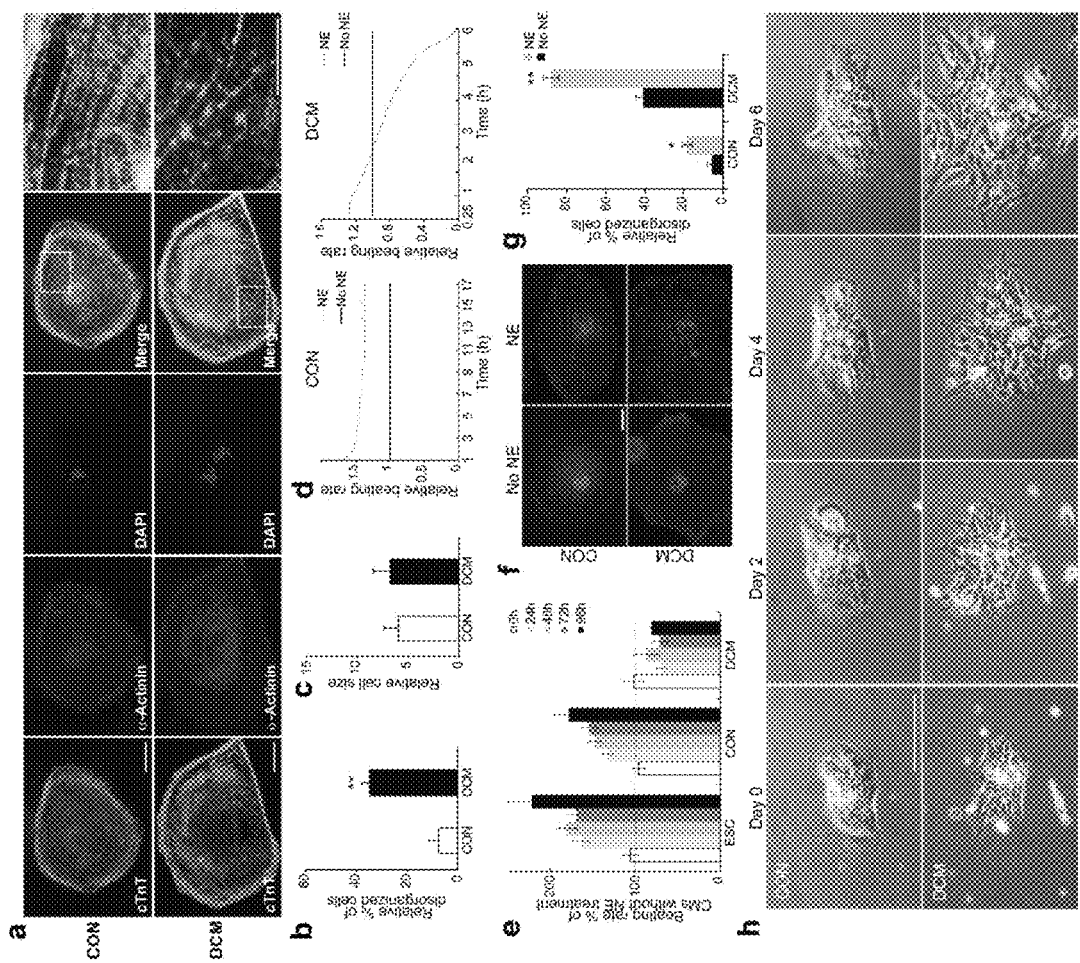
FIG. 2. DCM iPSC-CMs exhibited a significant higher number of cells with abnormal sarcomeric α-actinin distribution and early failure after NE treatment. (a) Immunostaining of sarcomeric α-actinin and cTnT at day 30 post differentiation. Single DCM iPSC-CMs exhibited punctate sarcomeric α-actinin distribution pattern suggesting a disorganized myofilament structure. Enlarged views of the boxed areas of the merged micrographs showing detailed α-actinin and cTnT staining pattern in the cells. Bars, 20 µm. (b) Compared to control iPSC-CMs (n=368), a significant higher percentage of DCM iPSC-CMs (n=391) showed punctate sarcomeric α-actinin staining pattern in greater than one fourth of the total cellular area (p=0.008). (c) No significant difference was observed in cell size between control (n=36) and DCM iPSC-CMs (n=39). (d) A representative MEA assay tracking contraction properties of both control (n=14) and DCM (n=14) beating EBs overtime with or without NE treatment. EBs were seeded in a dual chamber MEA probe with one side treated with NE and the other without. Electrical signals were recorded simultaneously during the experiments. Beating frequencies were normalized to those of EBs without NE treatment. (e) Normalized beating frequencies of CM clusters (n=10) over time after NE treatment by video imaging. (f) Representative images of sarcomeric α-actinin immunostaining on single control and DCM iPSC-CMs after 7 days of NE treatment. Compared to the controls, long term NE treatment significantly aggravated sarcomeric organization of DCM cells. Bar, 20 μm. (g) Percentage of CMs with disorganized sarcomeric staining pattern with (control, n=210; DCM, n=255) or without (control, n=261; DCM, n=277) NE treatment. NE treatment markedly increased the number of disorganized CMs in DCM group (p<0.001), and had a less significant effect on control iPSC-CMs (*p=0.05). (h) Tracking morphological and contractility changes of iPSC-CMs overtime after NE treatment. Bar, 200 μm. Data are presented as mean±s.e.m.
Figure 3:
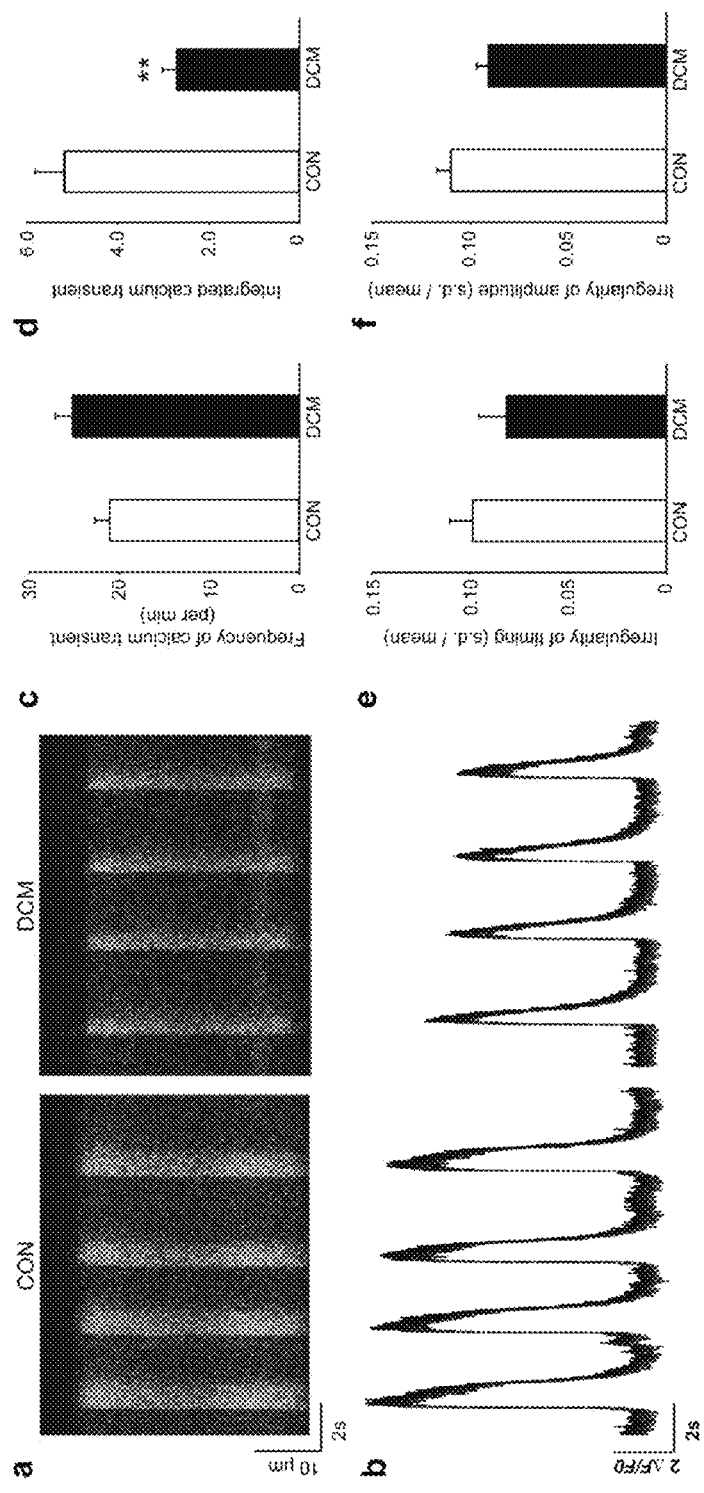
FIG. 3. DCM iPSC-CMs exhibited smaller $[Ca^{2+}]_i$ transients. (a) Representative line-scan images and (b) spontaneous calcium transients in CON (left) and DCM iPSC-CMs (right). (c) Frequency of spontaneous calcium transients in control and DCM iPSC-CMs. (d) Integration of $[Ca^{2+}]_i$ transients in control and DCM iPSC-CMs showed less $Ca^{2+}$ released in each transient in DCM relative to control cells (control, n=87 cells; DCM, n=40, **P=0.002). There were no significant differences in the (e) irregularity of timing (standard deviation/mean) or (f) amplitude of the spontaneous calcium transients between CON and DCM cells.
Figure 14:
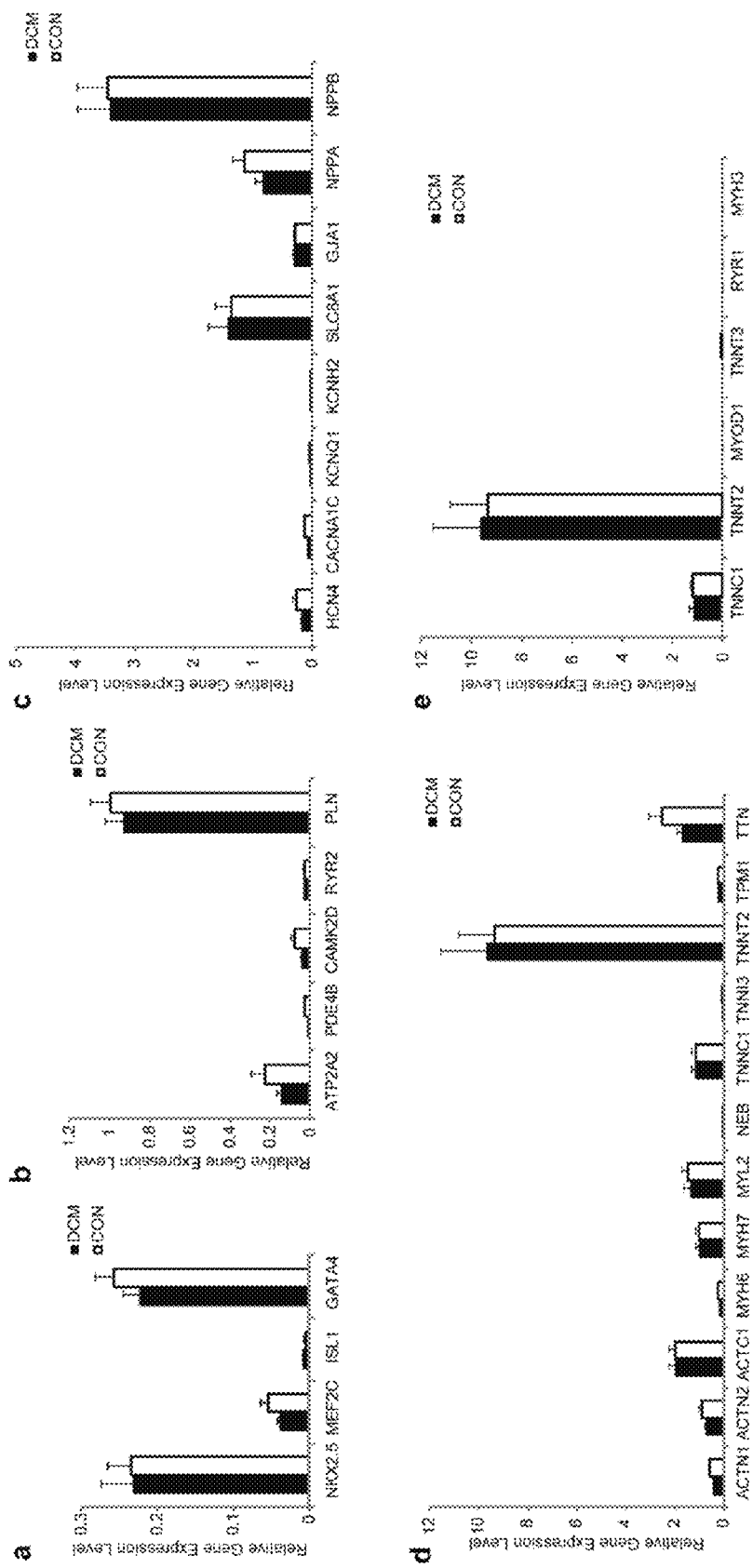
FIG. 14. Single cell PCR analyzing gene expression levels in 24 control and 24 DCM iPSC-CMs at day 30 post differentiation. Gene expression of (a) cardiac specific transcription factors, (b) calcium handling related proteins, (c) ion channels, (d) sarcomeric proteins, and (e) skeletal muscle specific proteins relative to gene expression level of α-tubulin were analyzed. No significant differences were observed between control and DCM CMs. Data are presented as mean±s.e.m. Statistical difference was tested using two tailed Student's T-test.
Figure 15:
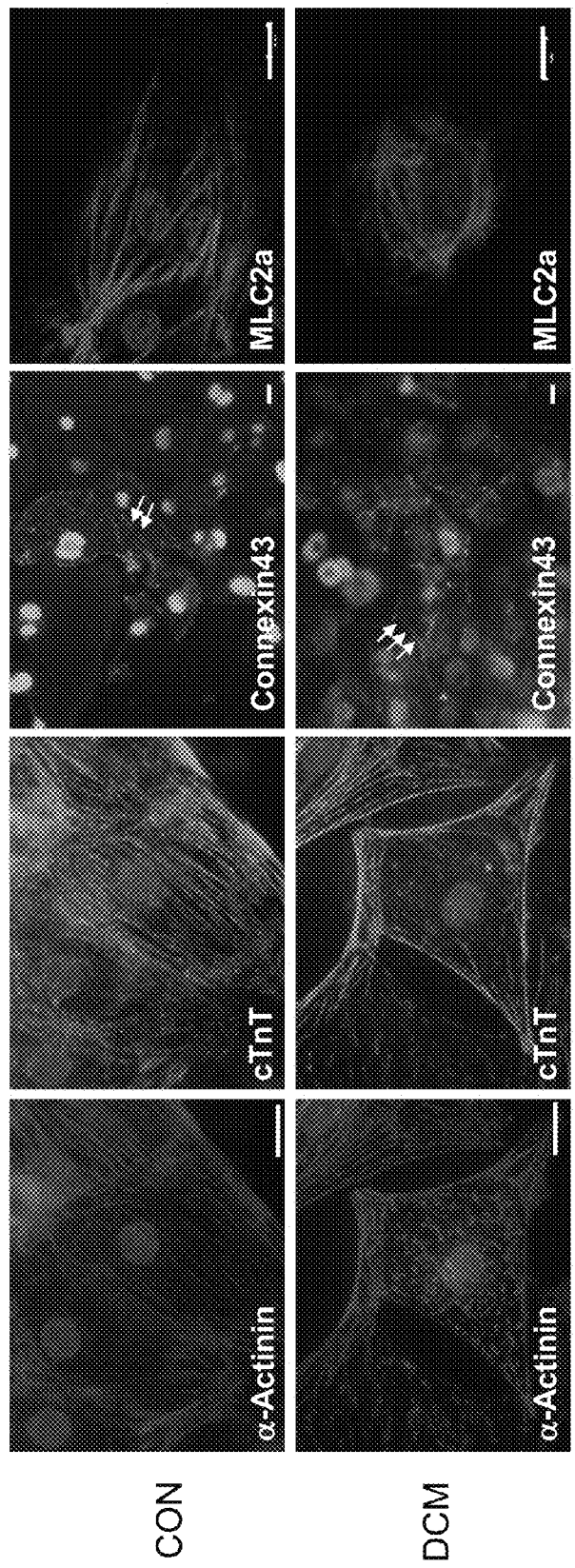
FIG. 15. iPSC-CMs expressed cardiac-specific proteins. Both control and DCM iPSC-CMs expressed cardiac specific proteins sarcomeric α-actinin, cTnT, connexin43, and MLC2a. Arrows indicate positive connexin43 staining at the cell-cell contact. Bars, 20 μm.
Figure 16:
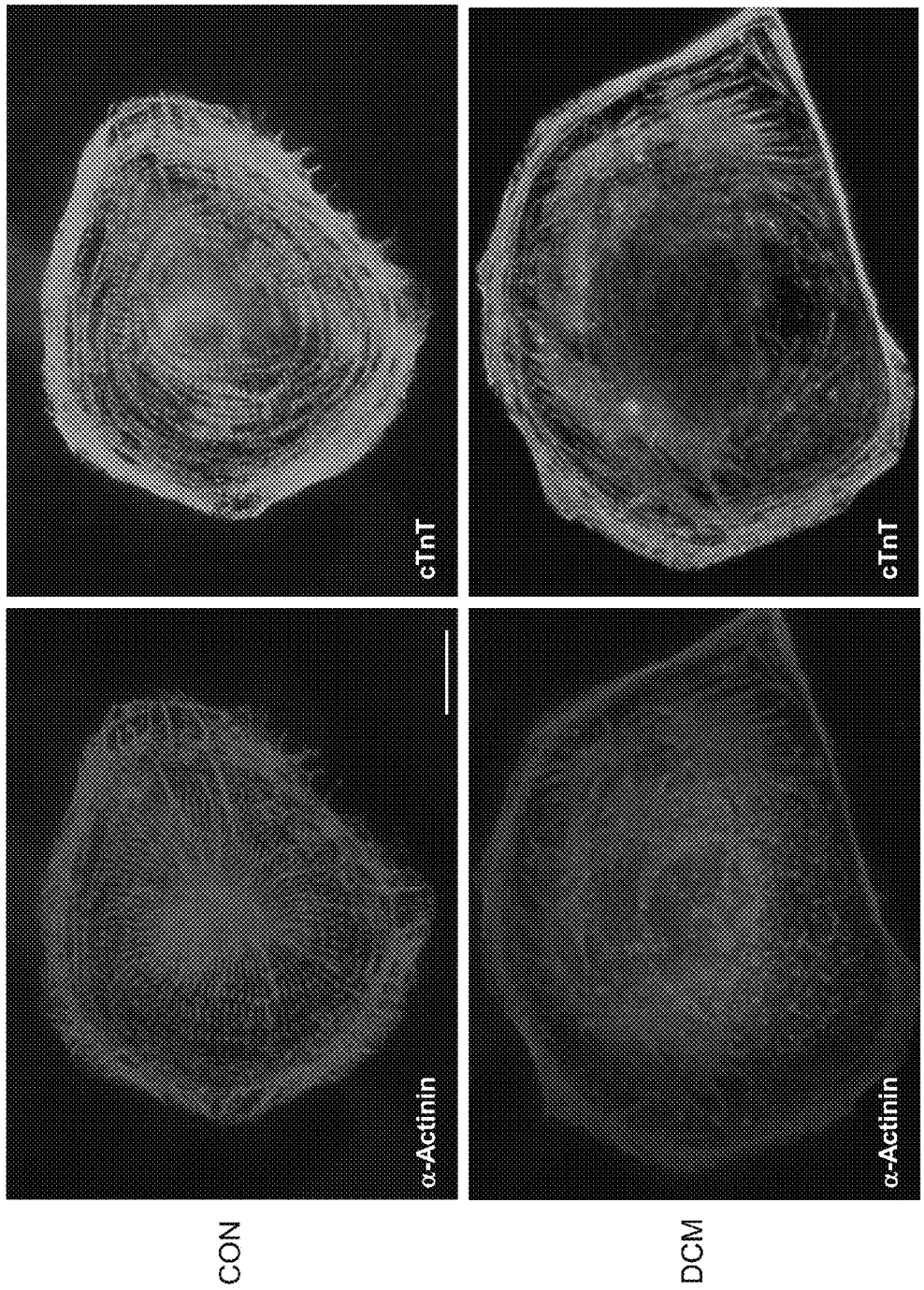
FIG. 16. Enlarged view of immunostaining of sarcomeric α-actinin and cTnT in the single CMs shown in FIG. 2a. Bar, 20 μm.
Figure 17:
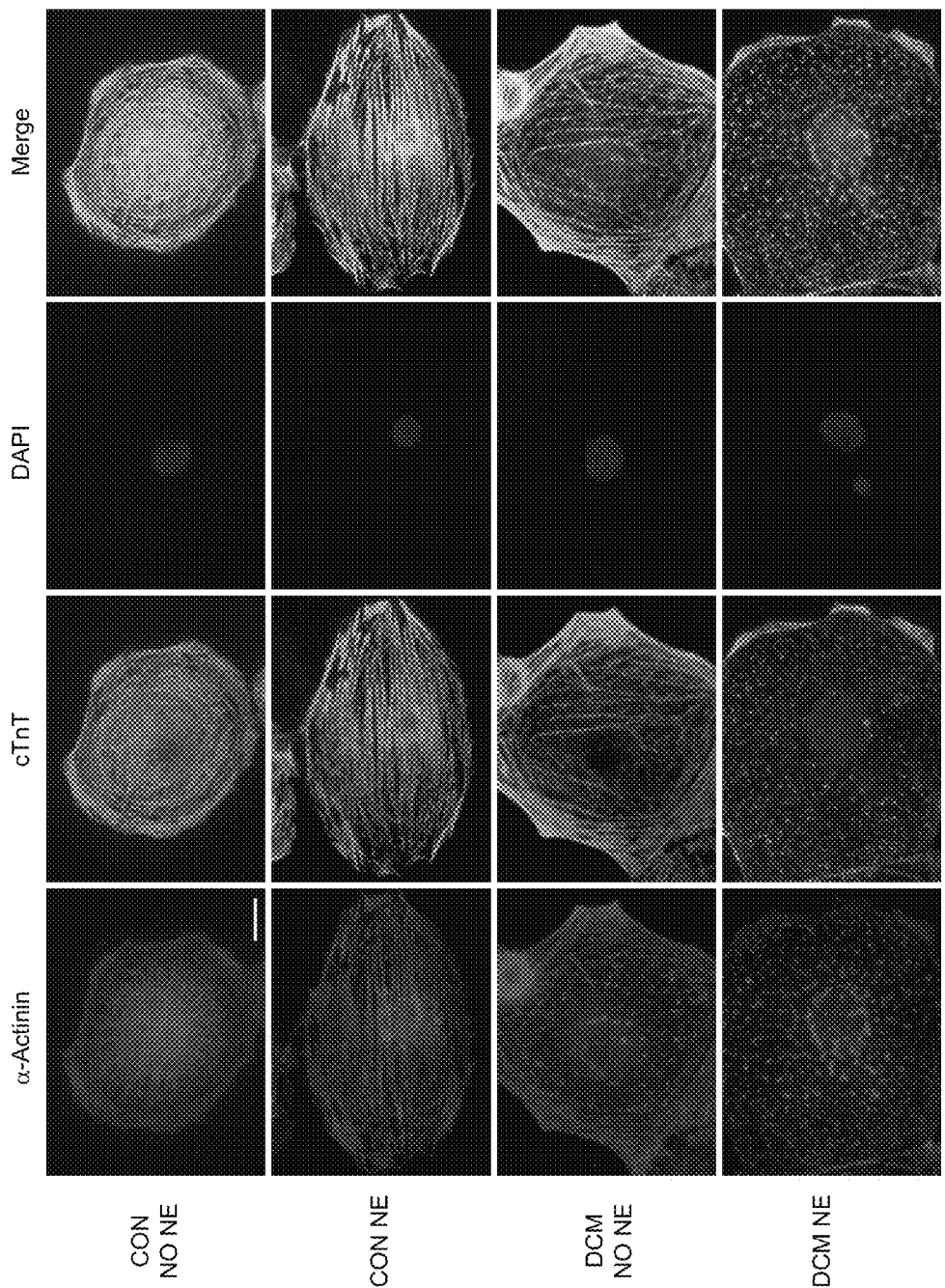
FIG. 17. Double immunostaining of sarcomeric α-actinin and cTnT in the single CMs shown in FIG. 2f. Bar, 20 μm.
Figure 18:
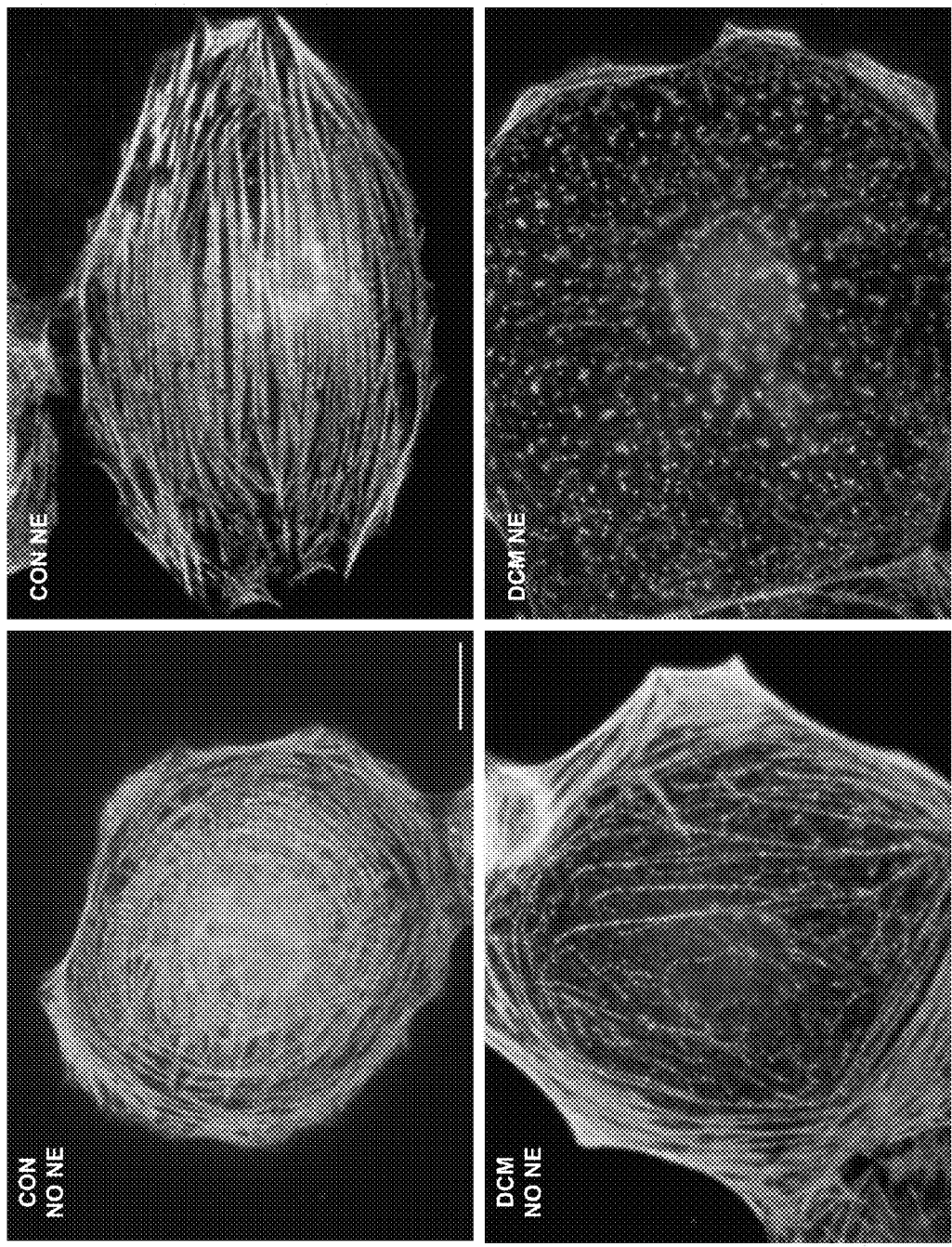
FIG. 18. Enlarged view of merged graph of each cell shown in FIG. 2f. Note that after NE treatment, some single DCM iPSC CMs showed complete degeneration of myofilaments, which was not observed in control CMs. Bar, 20 μm.

We next dissociated the beating EBs into small beating clusters and single beating CMs for further analyses. Single cell PCR analysis using microfluidics technology on control (n=24) and DCM (n=24) iPSC-CMs indicated that there are no significant differences in the gene expression of the selected cardiac-related transcription factors, sarcomeric proteins, and ion channels (FIG. 14). We next assessed the organization of myofibrils in the iPSC-CMs by immunocytochemistry. Both control and DCM iPSC-CMs expressed sarcomeric proteins cTnT, sarcomeric α-actinin, and myosin light chain 2a (MLC2a), as well as the cardiac marker gap junction protein connexin 43 (FIG. 15). However, compared to control iPSC-CMs (n=368) at day 30 post differentiation, a significant higher percentage of DCM iPSC-CMs (n=391) showed a punctate distribution of sarcomeric α-actinin over one fourth of the total cellular area (p=0.008) (FIG. 2a, 2b and FIG. 16). There were no significant differences in cell size between control and DCM iPSC-CMs (FIG. 2c) at this stage. This phenotype was consistently observed in two different DCM iPSC lines each from the 4 DCM patients, suggesting a homogeneous correlation to the disease-causing R173W mutation. Notably, the majority of CMs with punctate sarcomeric α-actinin distribution were single cells or cells at the periphery of a beating cluster. Sarcomeric α-actinin is an excellent marker for sarcomeric integrity and degeneration. These results also suggest a higher tendency for individual DCM iPSC-CMs to malfunction in maintaining sarcomere integrity.

Figure 19:
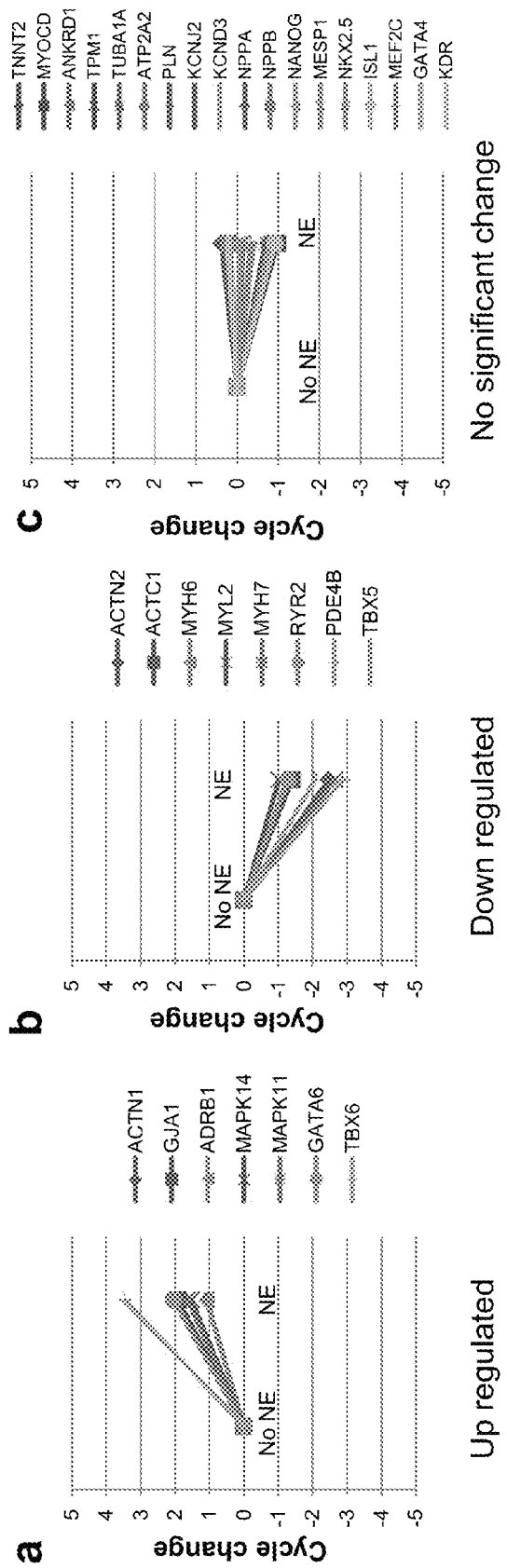
FIG. 19A-C. Real time PCR on single DCM iPSC-CMs versus control iPSC-CMs showed gene expression changes after one week of NE treatment. Control and DCM iPSC-CMs were seeded on culture dishes at day 19 post differentiation and were treated with or without 10 μM NE 48 h later for 7 days. Single CMs from control (treated with NE, n=8; without NE, n=8) and DCM (treated with NE, n=8; without NE, n=8) iPSCs were picked and PCR were performed as described in the Method section. Net threshold cycle (CT) values between cells treated with NE and without NE were first calculated. Data were then presented as the net CT values of the DCM group relative to the net ct values of control group. Genes were grouped as upregulated (>1 cycle difference in CT), downregulated (>1 cycle difference in CT), and no expression changes (<1 cycle difference in CT) after NE treatment.

Positive inotropic stress can induce DCM phenotype in transgenic mouse models of DCM and aggravate the disease in clinical patients. We next examined whether treatment with positive inotropic reagent, such as β-adrenergic agonists, can expedite the phenotypic response of DCM iPSC-CMs. Indeed, 10 µM norepinephrine (NE) treatment induced an initial positive chronotropic effect that later became negative, eventually leading to the failure of spontaneous contraction in DCM iPSC-derived beating EBs (n=14) as reflected by MEA recording. By contrast, the control iPSC-derived beating EBs (n=14) exhibited prolonged positive chronotropic activities (FIG. 2d). One week of NE treatment markedly increased the number of CMs with punctate sarcomeric α-actinin distribution from DCM iPSC clones, with almost 90% of the DCM iPSC-CMs found to have the disorganized sarcomeric pattern (FIG. 2f, 2g, FIGS. 17 and 18). A few single DCM iPSC-CMs showed complete degeneration of myofilaments after prolonged NE treatment, which was not observed in control cells. Tracking with video imaging of individual beating clusters of both control and DCM iPSC-CMs treated with NE over time showed distinct outcomes. Decreased inotropic and chronotropic activities were observed in the DCM iPSC-CMs, but not in the control iPSC-CMs (FIG. 2e, 2h). Single cell PCR analysis also revealed distinct gene expression changes in DCM (n=16) versus control iPSC-CMs (n=16) after NE treatment (FIG. 19). These results indicated that β-adrenergic stimulation aggravated the phenotype of DCM iPSC-CMs.

Figure 20:
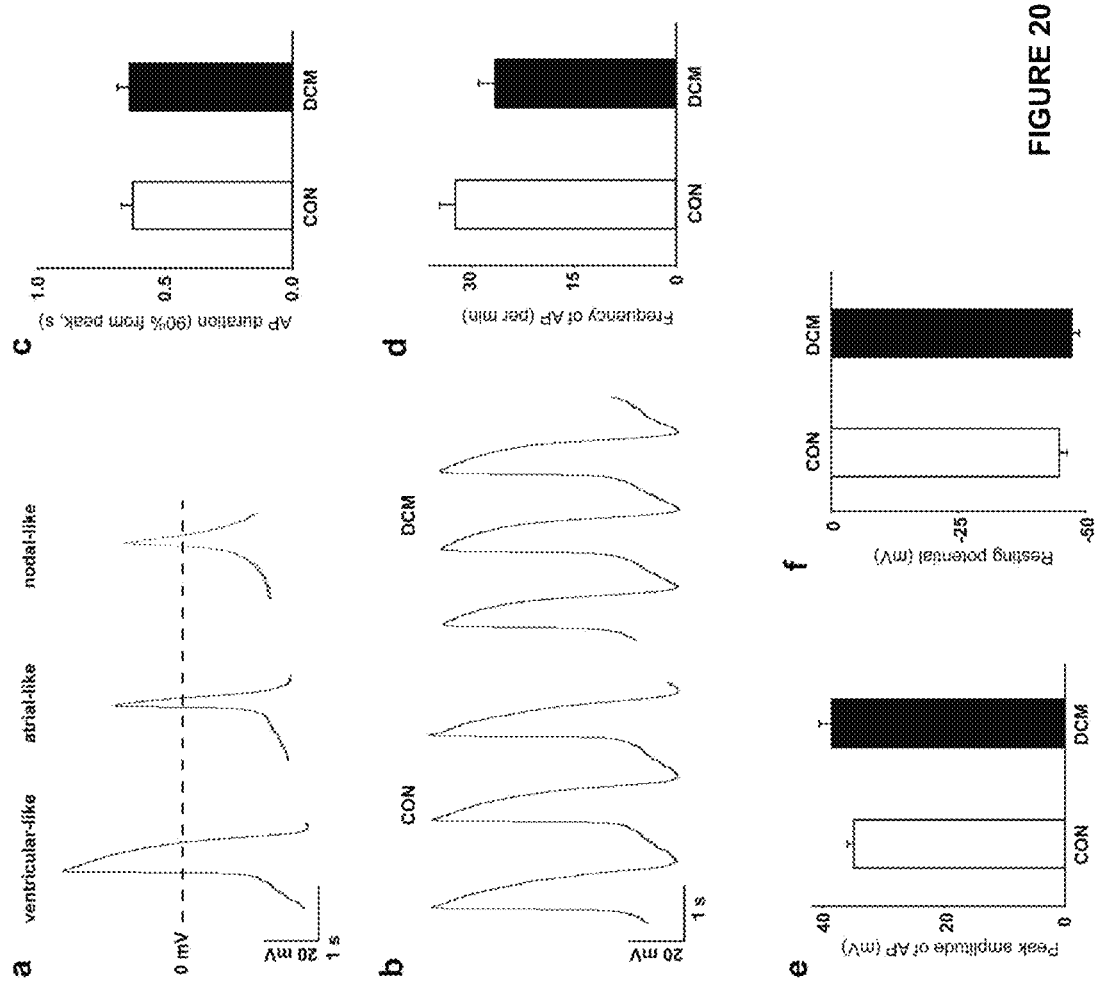
FIG. 20. Electrophysiological features of iPSC-CMs measured by patch clamping. (a) Three types of spontaneous AP were observed in both control and DCM iPSC-CMs (left, ventricular-like; center, atrial-like; right, nodal-like). An estimated 70-80% cells were ventricular-like CMs, whereas the others were atrial- and/or nodal-like cells. There is no significant difference in cardiac cell fate between control and DCM iPSCs (data not shown). (b) Spontaneous AP in control and DCM ventricular myocytes using current-clamp recording. DCM ventricular cells had slightly shorter APs compared to control cells (P=0.112) (c). There was no significant difference in the frequency (d), the peak amplitude of AP (e), or in the resting membrane potential (f) between control and DCM cells at the time of measurements (day 19-day 25 post differentiation) (control, n=18; DCM, n=17). Statistical difference was tested using the two tailed Student's T-test.

CM contraction starts from the electrical excitation of the myocytes, as reflected by the membrane action potentials (APs). To investigate the possible underlying mechanism of DCM, we assessed whether the DCM-linked R173W mutation in cTnT affects the electrical excitation of the CMs. We examined the electrical activities of the dissociated single beating iPSC-CMs by patch clamping. Three types of spontaneous APs (ventricular-like, atrial-like, and nodal-like) were observed in both control and DCM iPSC-CMs (FIG. 20a). DCM ventricular myocytes (n=17) exhibited normal APs that were comparable to control (n=18) (FIG. 20b). The average action potential duration at 90% repolarization (APD90) of the DCM iPSC-CMs was not significantly different from that seen in control iPSC-CMs (FIG. 20c). The average AP frequency, peak amplitude, and resting potential were also very similar between the 2 groups (FIGS. 20d, 20e, and 20f). These results indicated that the electrical excitation activities of control and DCM iPSC-CMs at baseline were normal.

To further investigate the underlying DCM disease mechanism, we measured the $Ca^{2+}$ handling properties at the excitation-contraction coupling level by fluorescent $Ca^{2+}$ imaging. DCM iPSC-CMs (n=40) exhibited rhythmic frequency, timing, and amplitude of global $[Ca^{2+}]_i$ transients comparable to those of the control iPSC-CMs (n=87) (FIGS. 3a, 3b, 3c, 3e, and 3f). However, DCM iPSC-CMs exhibited significantly smaller $[Ca^{2+}]_i$ transient amplitudes compared to those of the control iPSC-CMs (p=0.002) (FIG. 3d), indicating the $[Ca^{2+}]_i$ available for each, contraction of DCM iPSC-CMs was significantly lower. The smaller $[Ca^{2+}]_i$ transients of CMs were consistently observed in all examined DCM iPSC lines derived from the 4 DCM patients, suggesting weaker force production in DCM iPSC-CMs.

Figure 4:
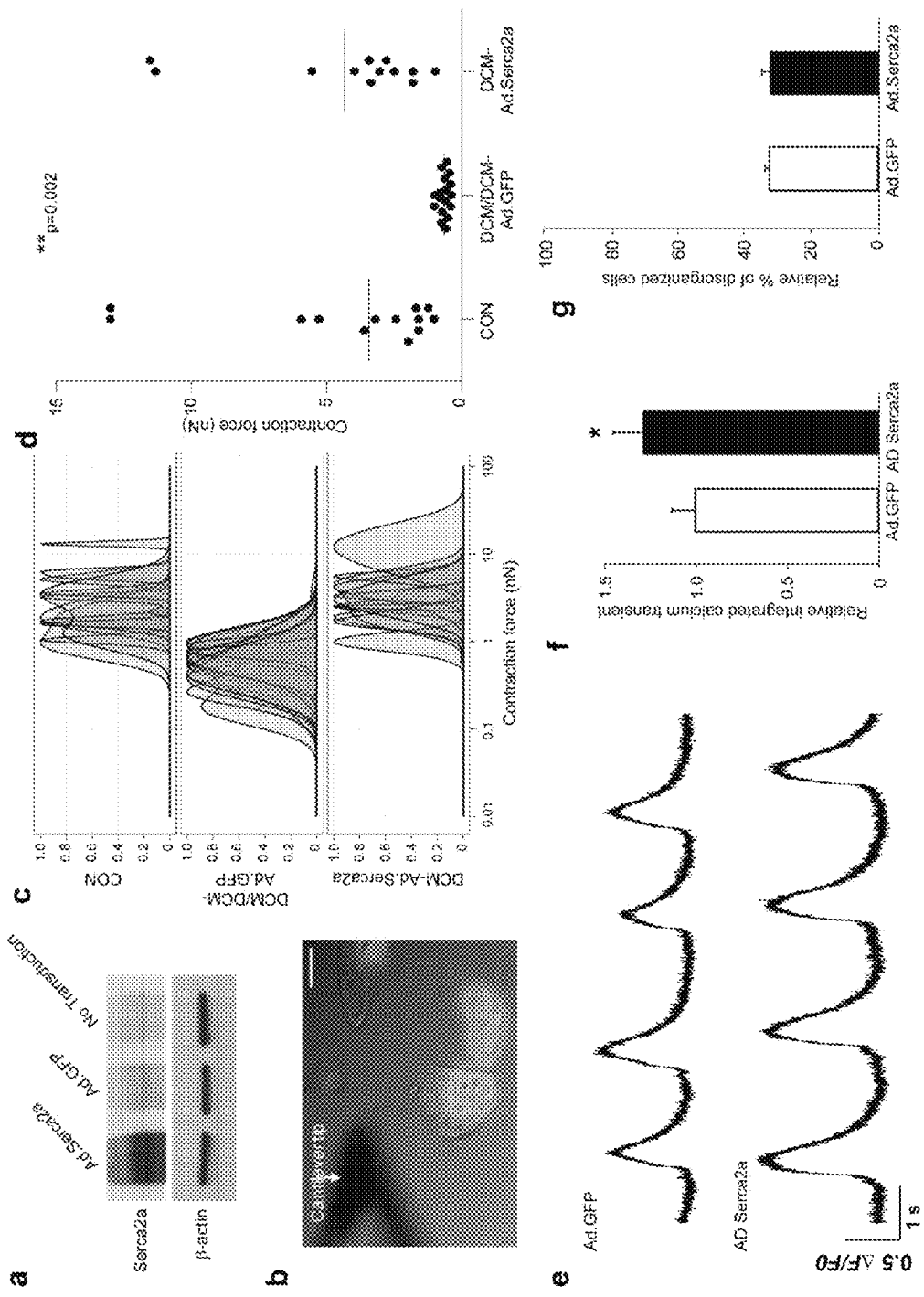
FIG. 4, Over-expression of Serca2a restored contractility of DCM iPSC-CMs. (a), Western blotting of Serca2a expression after adenoviral transduction of DCM iPSC-CMs. Serca2a protein level was upregulated in cells transduced with Ad.Serca2a but not in cells transduced with Ad.GFP. (b) A representative image showing the AFM cantilever approaching GFP positive single beating CMs. Bar, 50 μm. (c) Histograms of contraction forces of all the single iPSC-CMs measured by AFM over 100-400 beats. Over-expression of Serca2a significantly restored the contraction force of DCM iPSC-CMs to a level close to that of the controls. (d) Dot plots of mean contraction force of single CMs measured by AFM. One-way ANOVA analysis indicated that there was significant difference among the mean of all the groups (**p=0.002). Tukey's Multiple Comparison Test indicated that both control iPSC-CMs (n=13) (P=0.001) and Ad.Serca2a (n=12) (P=0.005) transduced DCM iPSC-CMs exhibited significantly stronger contraction force than that transduced by Ad.GFP (n=17). Ad.Serca2a transduced DCM iPSC-CMs showed comparable contraction force to that of the control iPSC-CMs (p=0.578). (e) Representative spontaneous calcium transients in single DCM iPSC-CMs transduced with Ad.GFP and Ad.Serca2a, respectively. (f) DCM iPSC-CMs transduced with Ad.Serca2a (n=22) exhibited increased global calcium transients compared to cells transduced with Ad.GFP (n=14). (*p=0.04) (two-tailed Student's t-test). (g) Percentage of CMs with disorganized sarcomeric staining pattern in DCM iPSC-CMs with Ad.Serca2a (n=40) or Ad.GFP (n=40) over-expression. No significant difference was observed between the two groups (two-tailed Student's t-test). Data are presented as mean±s.e.m.
Figure 21:
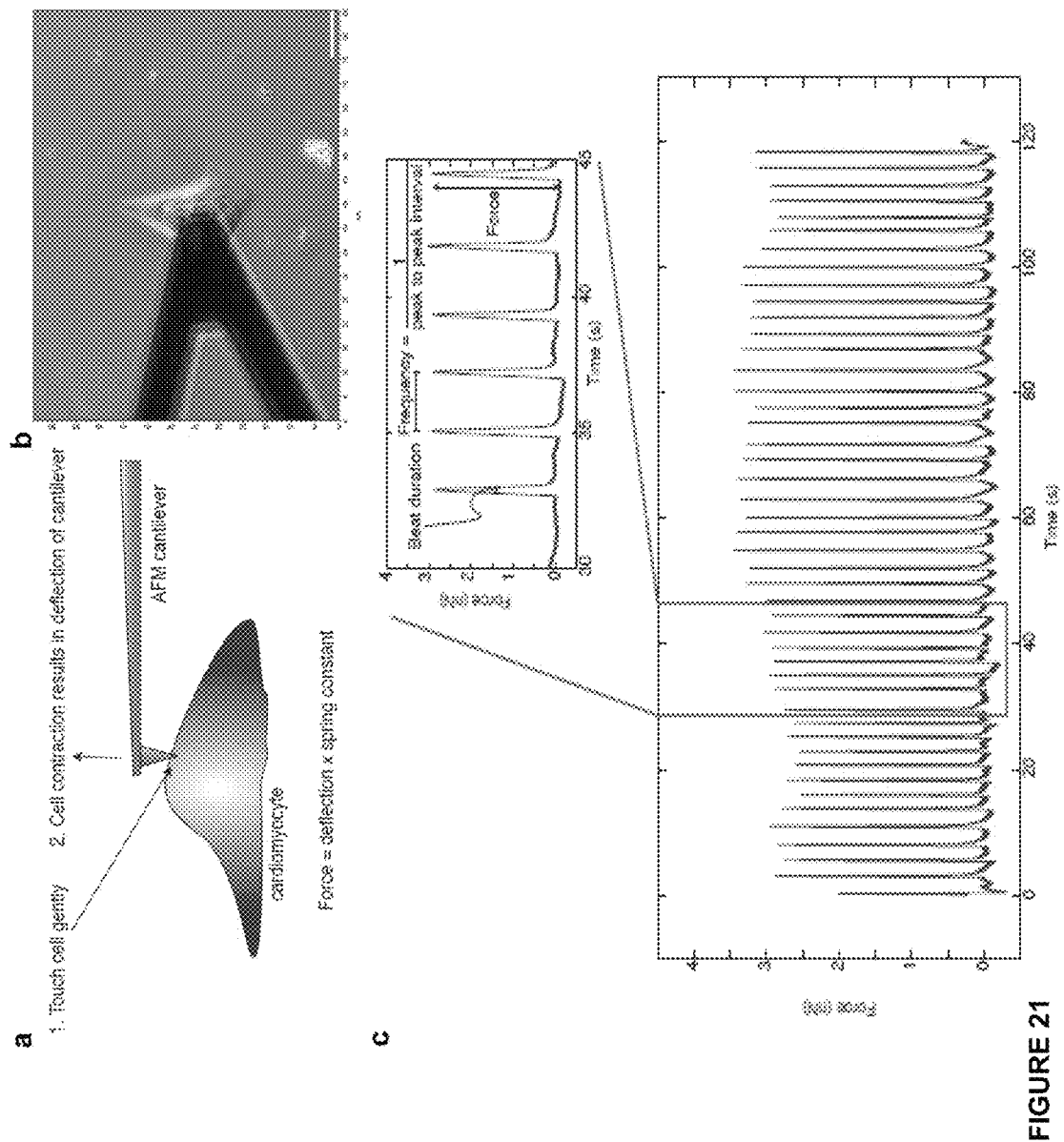
FIG. 21. Atomic force microscopy (AFM) measurement of contraction force of iPSC-CMs. (a) Schematic of the process of force measurement by AFM at a single cardiomyocyte level. (b) A representative image showing AFM cantilever probing a single cardiomyocyte. Bar, 20 μm. (c) A representative graph showing the signals acquired by AFM and the parameters examined (force, frequency, and beat duration).
Figure 22:
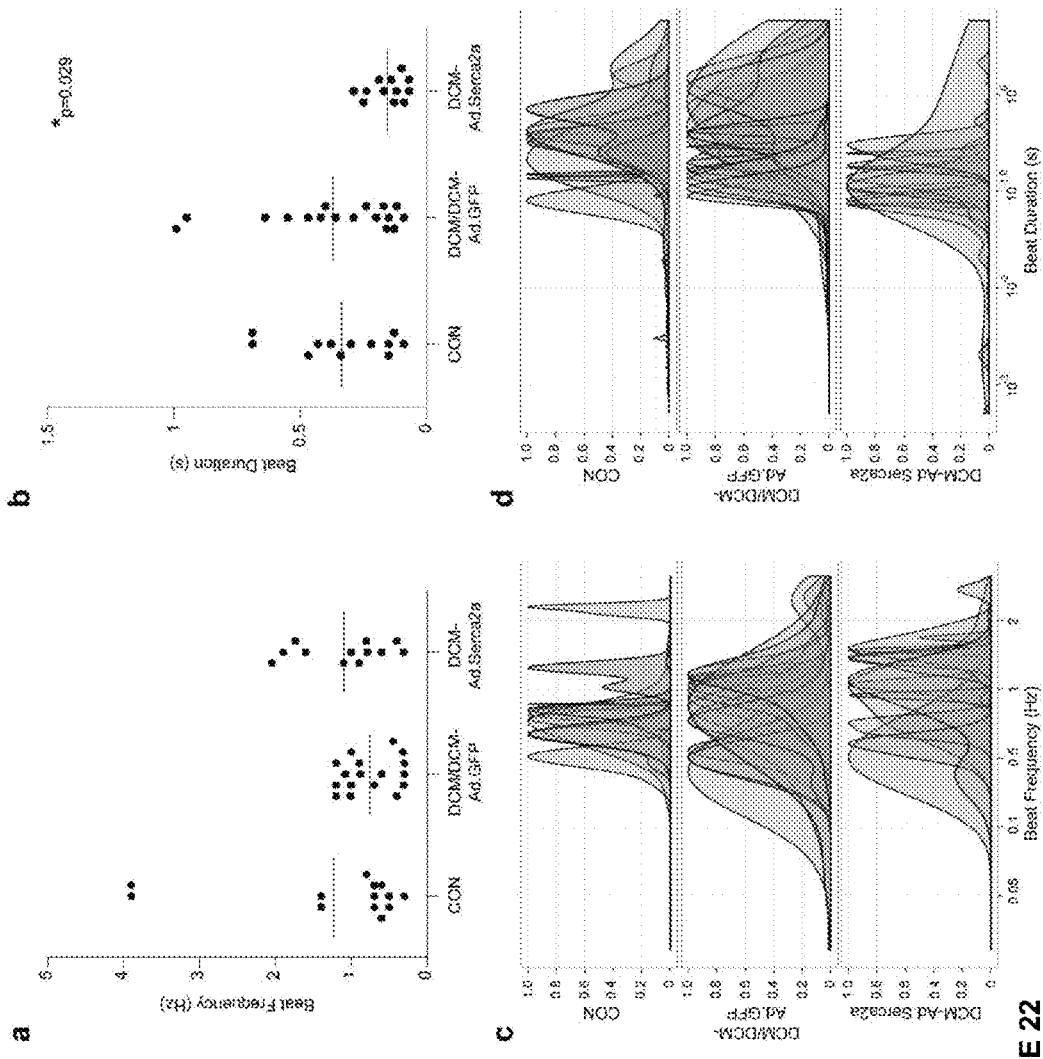
FIG. 22. Beat frequency and duration of single iPSC-CMs measured by AFM. (a) Dot plots of mean beat frequency measured by AFM. No significant difference in beat frequency and rhythm was observed between control iPSC-CMs (n=13), Ad.Serca2a (n=12) and Ad.GFP (n=17) transduced DCM iPSC-CMs. (b) Dot plots of mean beat duration measured by AFM. Over-expression of Serca2a significantly shortened the beat duration (*p=0.029). Statistical difference was tested using one-way ANOVA followed by Tukey's Multiple Comparison Test. (c) Histograms of beat frequency and (d) beat duration of all the single iPSC-CMs measured by AFM over 100-400 beats.
Figure 23:
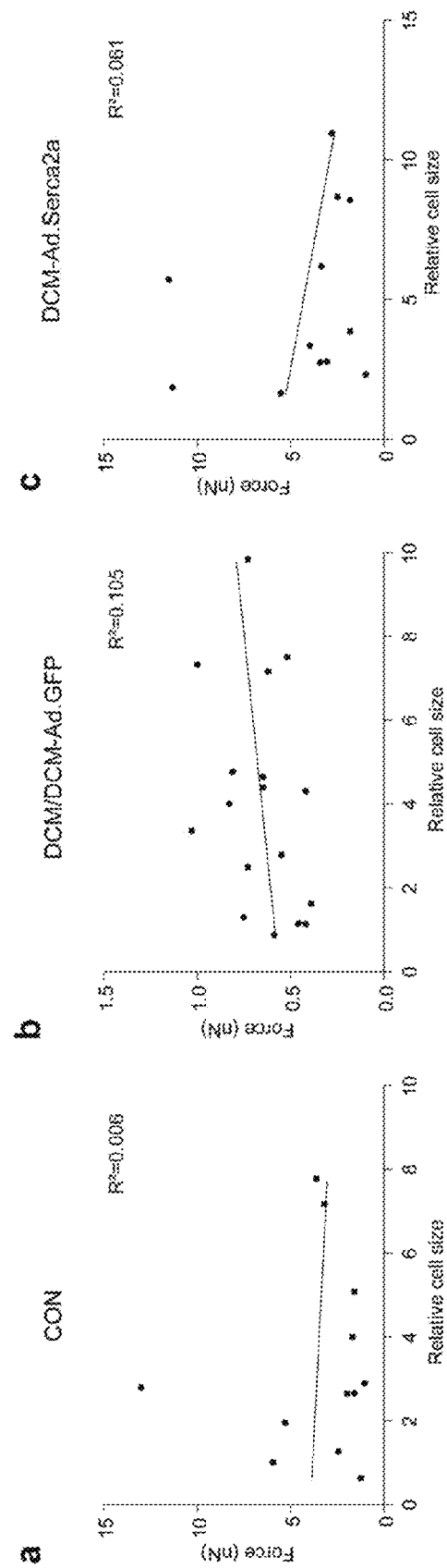
FIG. 23. Dot plots of relative cell size versus contraction force for each single cell measured by AFM. There is no significant linear relationship between cell size and contraction force in (a) control ($R^2$=0.006), (b) DCM/DCM-Ad.GFP ($R^2$=0.105), and (c) DCM-Ad.Serca2a ($R^2$=0.061) groups.

Deficiency in contractile force production is one of the most important mechanisms responsible for inducing DCM and heart failure. To further investigate this, we next measured the contraction force of iPSC-CMs using atomic force microscopy (AFM), which has been used to measure cultured chicken embryonic CMs. The AFM allowed us to probe the contractile properties at a single cell level (FIG. 21). Compared to single control iPSC-CMs (n=13), DCM iPSC-CMs (n=17) showed similar beat frequency and duration but significantly weaker contraction forces (FIG. 4c, 4d, FIG. 22, and Table 5). There was no correlation between the cell size and contraction force from each single cell measured by AFM (FIG. 23).

Figure 24:
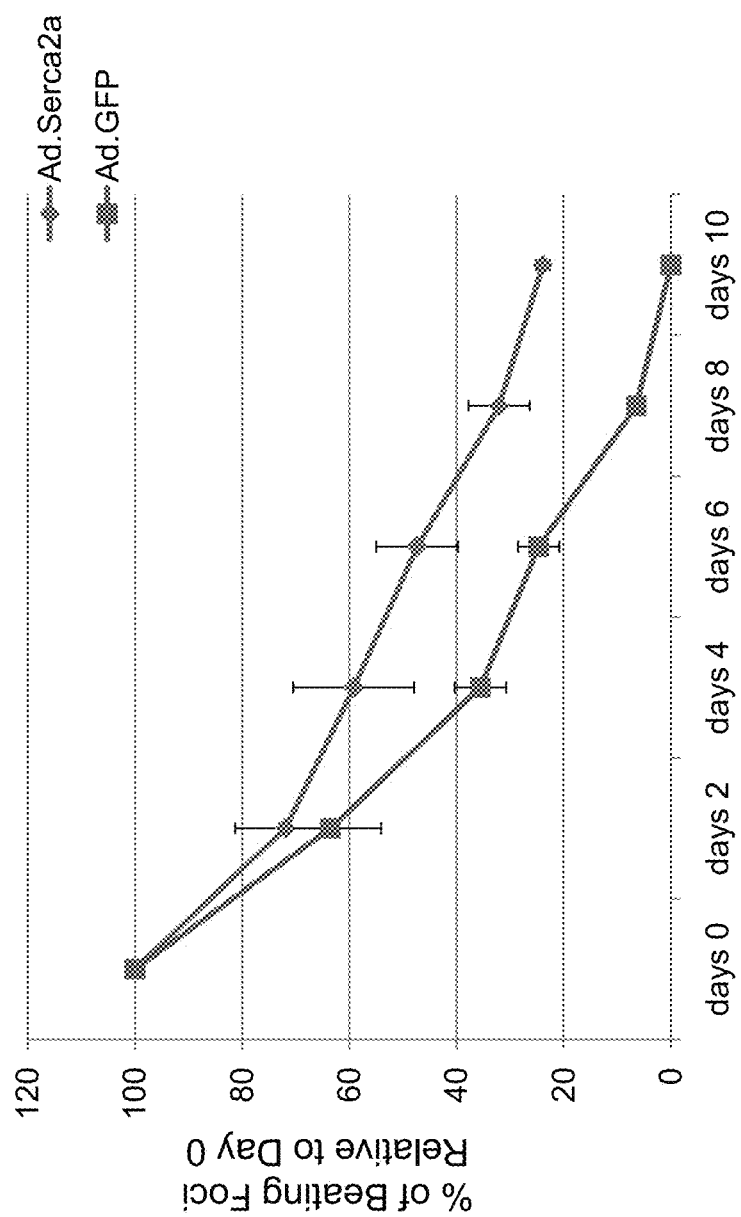
FIG. 24. Normalized percentage of beating foci in culture dish over time after Serca2a and GFP over-expression. Data represent averages of three independent replicates of experiments (mean±s.e.m.).
Figure 25:
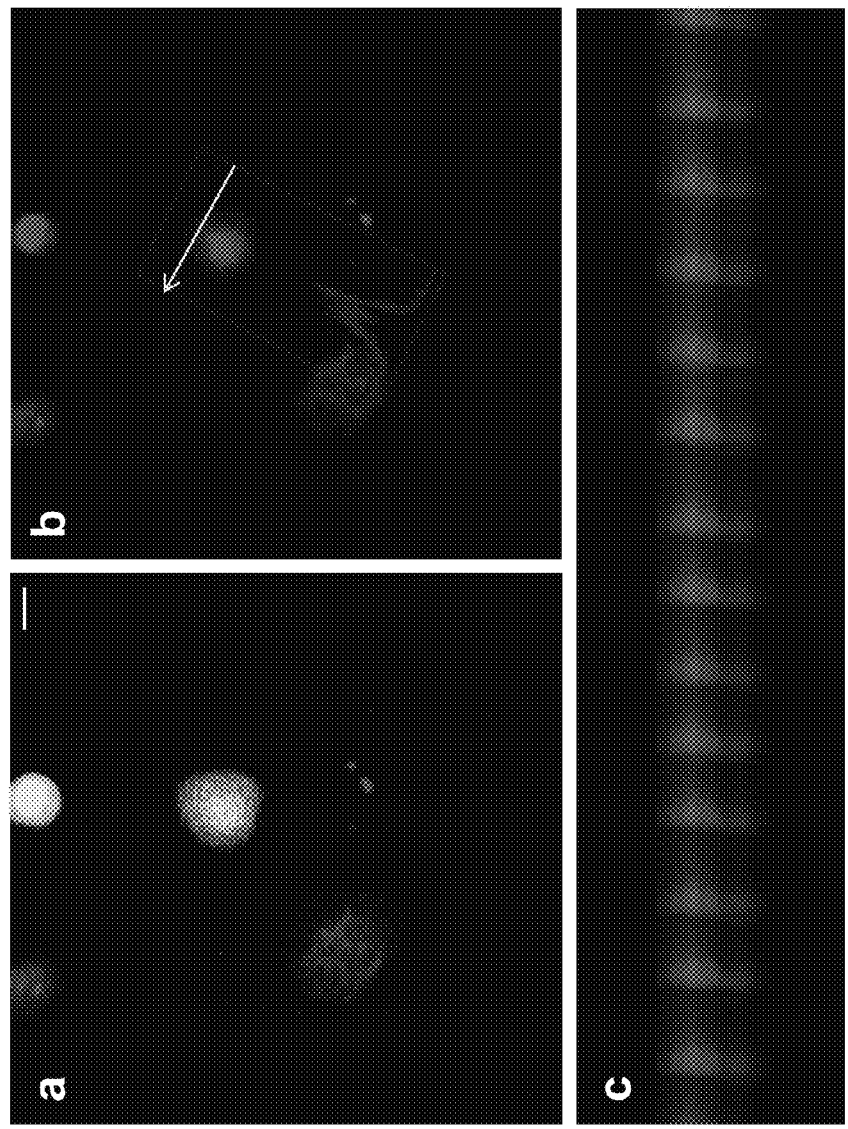
FIG. 25. $Ca^{2+}$ imaging of iPSC-CMs transduced with Ad.Serca2a or Ad.GFP adenoviruses with red fluorescent $Ca^{2+}$ indicator Rhod-2 AM. (a) Merged confocal images showing the GFP positive CMs uptook the Rhod-2 dye. (b) The same cell in (a) was scanned with the arrow line indicated in the picture. (c) The line scan images recorded for the particular CM shown in (a) and (b). Bar, 20 μm.
Figure 26:
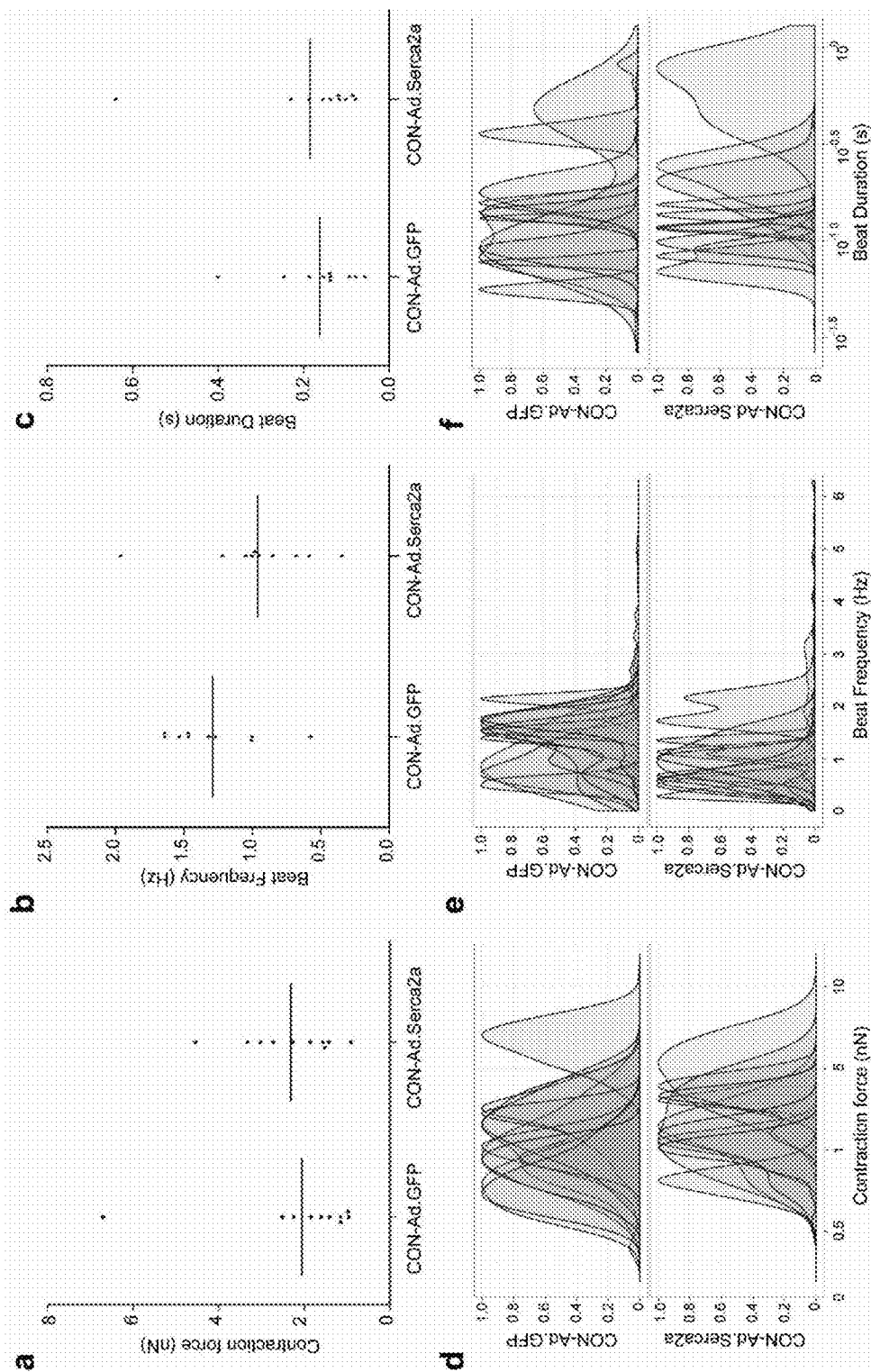
FIG. 26. Contractility of control iPSC-CMs transduced with Ad.Serca2a or Ad.GFP as measured by AFM. (a) Dot plots of contraction force, (b) beat frequency, and (c) beat duration of control iPSC-CMs transduced with Ad.Serca2a (n=10) or Ad.GFP (n=10). No significant statistical differences were observed between the mean of each group. Statistical difference was tested using two tailed Student's T-test. (d) Histograms of contraction force, (e) beat frequency, and (f) beat duration of all the single control iPSC-CMs measured by AFM over 100-400 beats.

Previous studies have shown that Serca2a over-expression, a treatment investigated in a pre-clinical trial, mobilized intracellular $Ca^{2+}$ and restored contractility of cardiomyocytes in failing human hearts and improved failing heart functions in animal models. Given our results showing smaller $Ca^{2+}$ transients and compromised contractility in DCM iPSC-CMs, we hypothesized that over-expression of Serca2a can rescue the phenotypes of DCM iPSC-CMs. Transduction of DCM iPSC-CMs with adenoviruses carrying Serca2a co-expressing GFP (Ad.Seca2a) (see Methods section) at a multiplicity of infection (MOI) of 100 led to over-expression of Serca2a in these cells (FIG. 4a). Compared to DCM iPSC-CMs transduced with adenoviruses carrying GFP only (Ad.GFP) (MOI 100), over-expression of Serca2a resulted in a higher number of spontaneous contraction foci in vitro over time (FIG. 24). Co-expression of GFP along with Serca2a allowed us to recognize the transduced cells and measure the contractile force by AFM (FIG. 4b). Over-expression of Serca2a (n=12) restored the contractile force of single DCM iPSC-CMs to a level similar to that seen in control iPSC-CMs (FIG. 4c, 4d, and Table 5), but without improvement in sarcomeric organization (FIG. 4g). Calcium imaging using the red fluorescent $Ca^{2+}$ indicator Rhod-2 AM (FIG. 25) indicated that DCM iPSC-CMs transduced with Ad.Serca2a co-expressing GFP (n=22) had significantly increased global $[Ca^{2+}]_i$ transients compared to cells transduced with Ad.GFP only (n=14) (FIGS. 4e and 4f) (p=0.04), which is consistent with the restored force production. By contrast, over-expression of Serca2a in control iPSC-CMs failed to produce a statistically significant increase in contractility (FIG. 26), suggesting natural differences in calcium handling between control and DCM iPSC-CMs. Altogether, these results indicated that over-expression of Serca2a increased the $[Ca^{2+}]_i$ transients and contraction force of DCM iPSC-CMs and improved their function.

Figure 27:
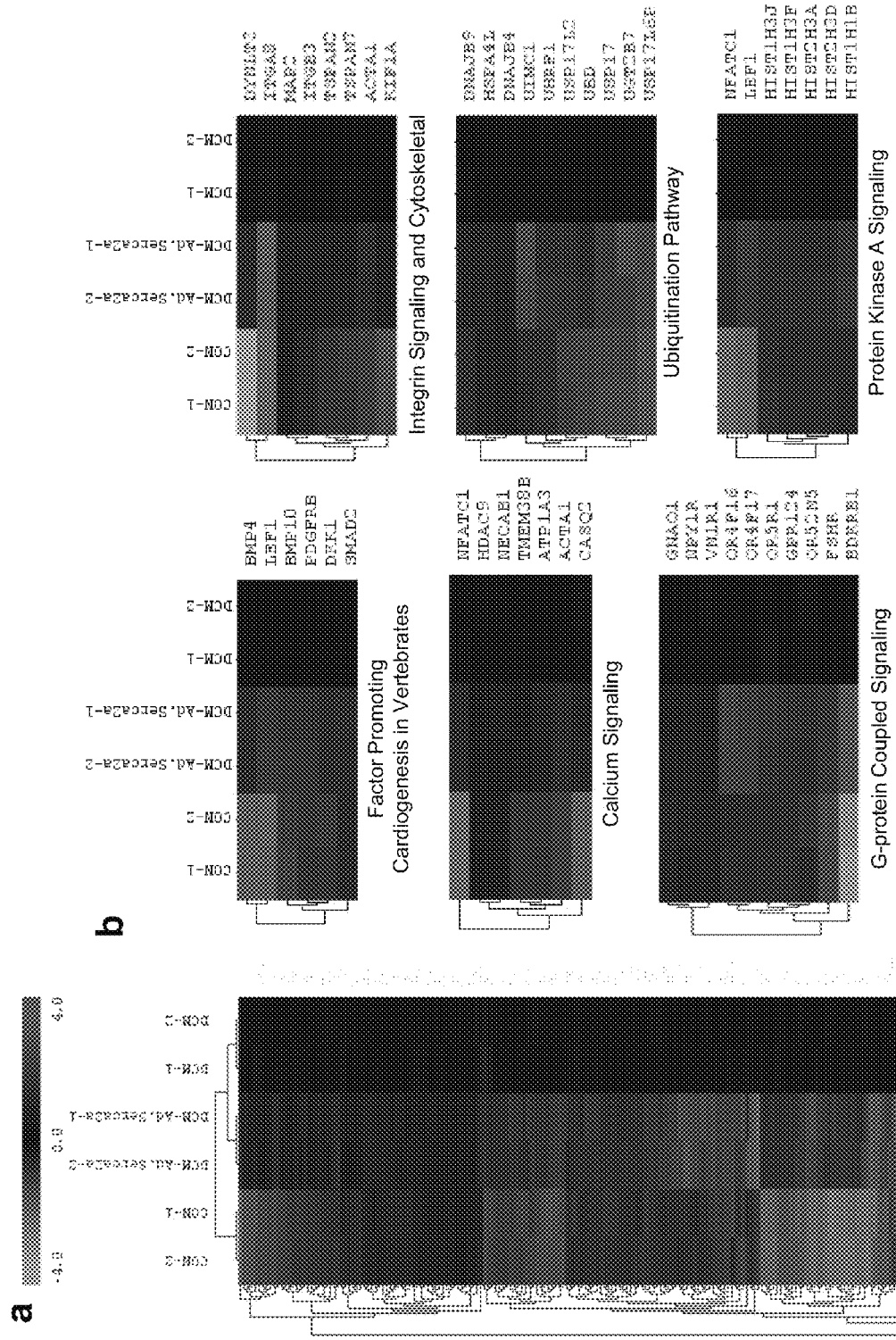
FIG. 27. Gene expression profiling of DCM iPSC-CMs with Serca2a over-expression identified enriched pathways that may function in rescuing the DCM phenotype. (a) Heatmap of the 191 genes with greater than 1.5-fold difference in expression in biological replicates of control iPSC-CMs and Serca2a-treated DCM iPSC-CMs compared with DCM iPSC-CMs without Serca2a treatment. (b) Heatmap of enriched pathways that may be involved in rescuing the DCM phenotype by Serca2a over-expression.

Although Serca2a gene therapy is now in clinical trial, the overall mechanism of individual CM cellular response after Serca2a gene therapy has not been extensively studied previously. Hence we set out to investigate the mechanisms in which Serca2a delivery restores defects in DCM iPSC-CMs. Gene expression profiling of DCM iPSC-CMs after Serca2a over-expression showed that 191 genes (65 upregulated and 126 downregulated) had greater than 1.5 fold expression changes and were rescued to an expression level similar to those in control iPSC-CMs (FIG. 27a). Enriched pathways analysis indicated that several previously known pathways, such as calcium signaling, protein kinase A signaling, and G-protein coupled receptor signaling, are significantly involved in rescuing the DCM phenotype by Serca2a over-expression. Interestingly, several pathways not previously linked to DCM, including factors promoting cardiogenesis, integrin and cytoskeletal signaling, and ubiquitination pathway, were also found to participate in rescuing the DCM CM function (FIG. 27b and Table 7).

Figure 28:
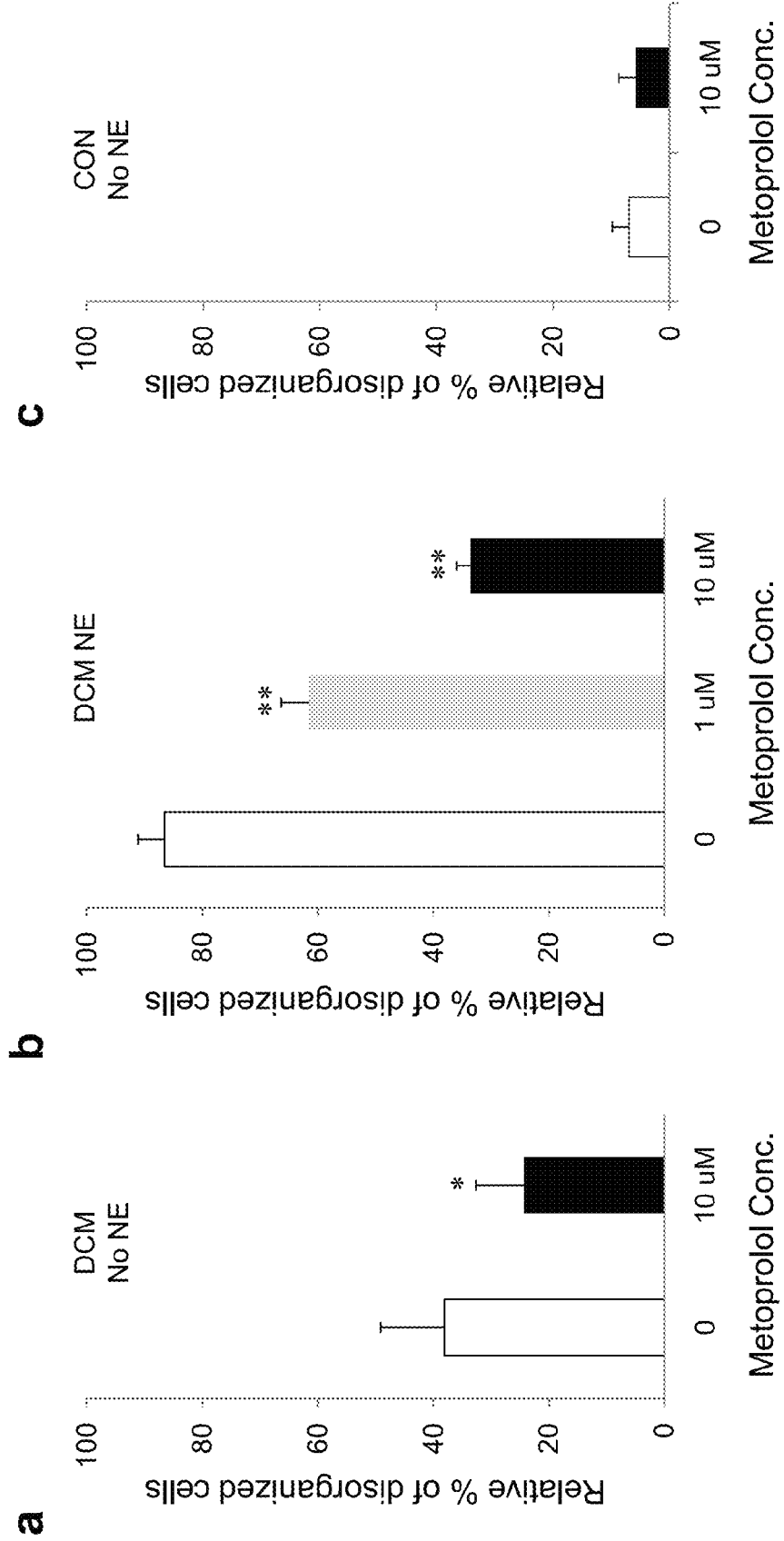
FIG. 28. Metoprolol treatment improved sarcomeric organization of DCM iPSC-CMs and alleviate the aggravation effect of NE treatment. (a) Ten μM metoprolol treatment increased the number of DCM iPSC-CMs with intact sarcomeric integrity (untreated, n=100; treated, n=86, *p=0.023). (b) Metoprolol treatment prevented the aggravation of DCM iPSC-CMs induced by NE treatment. Both 1 μM (n=107, p=0.008) and 10 μM (n=101, p=0.001) metoprolol significantly decreased the number of disorganized cells compared to those without metoprolol treatment (n=108). (c) Ten μM metoprolol treatment had no significant effect on the sarcomeric integrity of control iPSC-CMs (untreated, n=88; treated, n=75). Data are presented as mean±s.e.m. Statistical difference was tested using the two tailed Student's T-test.

Clinical studies have shown that metoprolol, a β1-selective β-adrenergic blocker, has a beneficial effect on the clinical symptoms and hemodynamic status of DCM patients. When treated with 10 μM metoprolol, DCM iPSC-CMs showed an improvement in the sarcomeric organization as indicated by sarcomeric α-actinin staining (FIG. 28a). Metoprolol treatment also prevented aggravation of the DCM iPSC-CMs that is induced by NE treatment (FIG. 28b). We observed no significant effect on sarcomeric α-actinin distribution in control iPSC-CMs treated with metoprolol (FIG. 28c). These results suggest that blockade of β-adrenergic pathway helped DCM iPSC-CMs resist mechanical deterioration.

Figure 29:
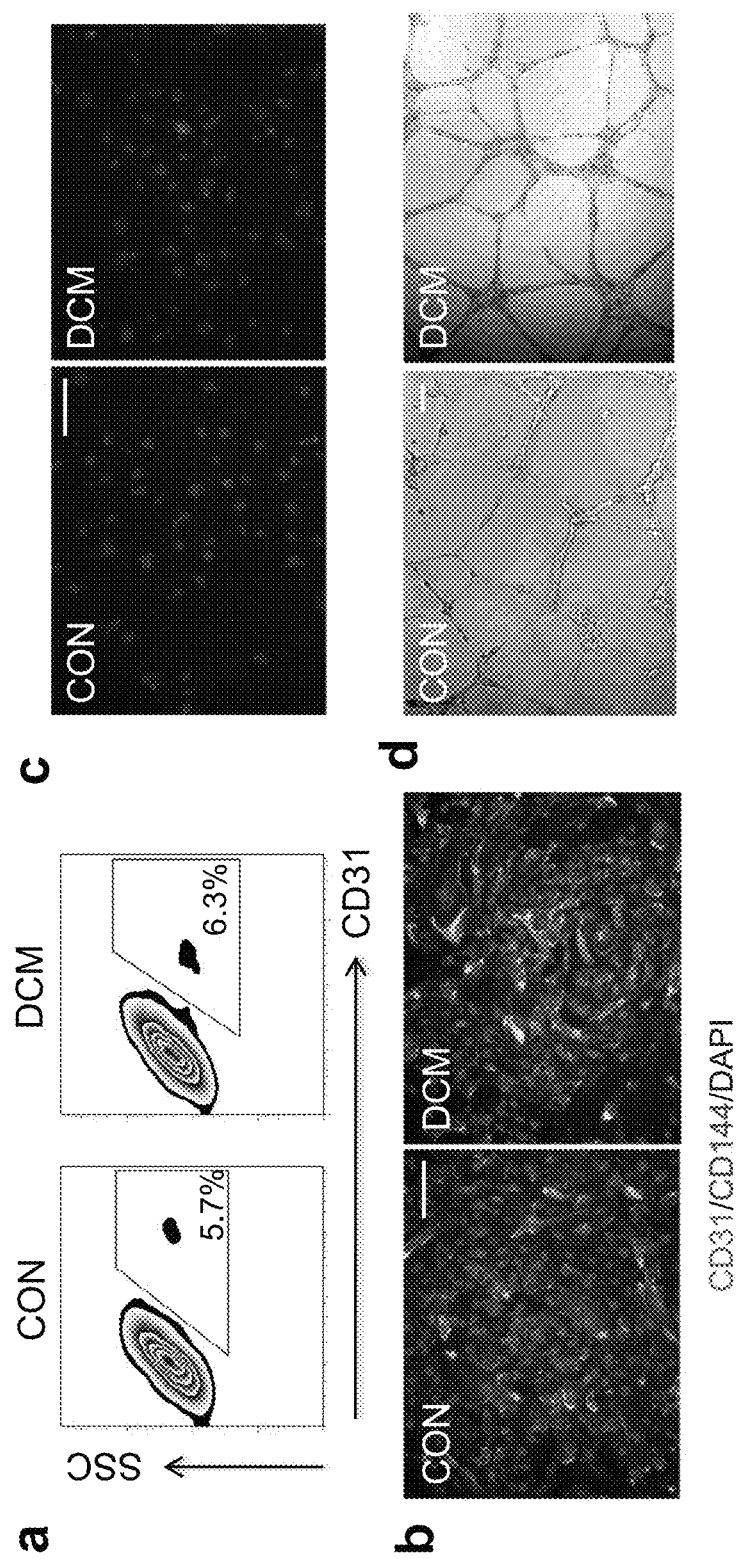
FIG. 29. Similar functional properties of DCM iPSC-ECs and control iPSC-ECs. (a) FACS analyses indicated the efficiency of differentiation of both DCM and control iPSCs to $CD31^+$ ECs were similar. (b) The FACS isolated $CD31^-$ cells from differentiated DCM and control iPSCs expressed both the endothelial cell markers CD31 and CD144. (c) Both DCM and control iPSC-derived ECs exhibited uptake capability of low density lipoprotein (LDL) (red fluorescence). (d) Both control and DCM iPSC-derived ECs were able to form web-like tubules on Matrigel surface. Bars, 100 μm.
Figure 30:
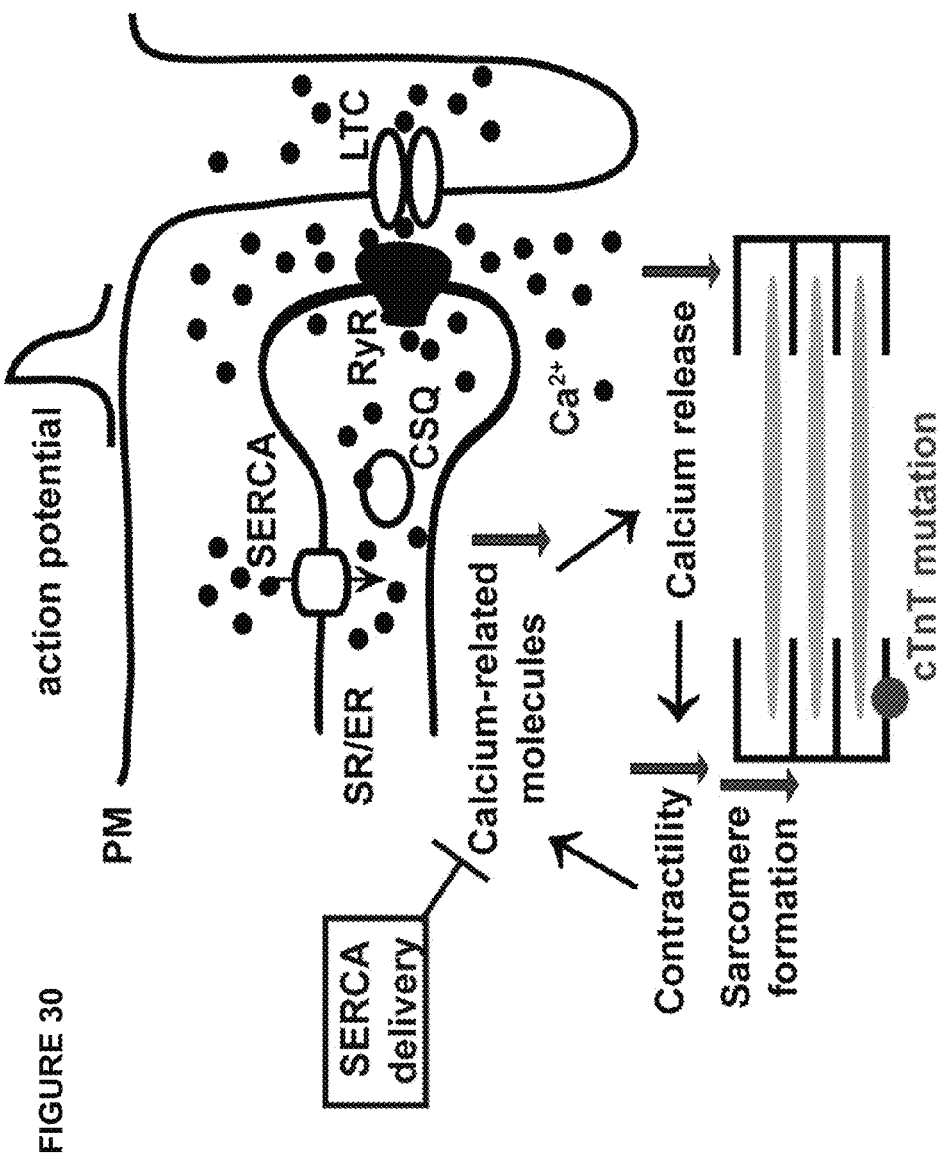
FIG. 30. Schematic of potential mechanisms by Serca2a gene therapy in DCM iPSC-CM. The mutation in cardiac troponin T negatively affects contractility, sarcomere formation, and calcium signaling, which causes changes in calcium-related genes such as calsequestrin, NFAT, and TRIC channels. However, electrical excitation was normal in the TNNT2 R173W DCM iPSC-CMs. Delivery of Serca2a, the SR/ER membrane calcium pump, restored the level of calcium handling molecules, reversed the compromised calcium transients and contractility, and thereby improved the overall DCM iPSC-CM function. cTnT, cardiac troponin T; LTC, L-type calcium channel; RyR, ryanodine receptor calcium release channel; CSQ, calsequestrin; PM, plasma membrane.

In summary, we have generated patient-specific iPSCs from a DCM family carrying a single point mutation in the sarcomeric protein cTnT and derived CMs from these iPSCs. This has allowed us to generate a large number of DCM-specific CMs and to analyze their functional properties, explore the underlying disease mechanisms, and test effective therapies (Table 8). Although the baseline electrophysiological activities of the DCM iPSC-CMs were not significantly different from those of the controls, DCM iPSC-CMs exhibited significantly smaller $[Ca^{2+}]_i$ transients and decreased contractile force. A weaker ability to resist mechanical stimulation was also associated with DCM iPSC-CMs. NE stimulation induced a cessation of their spontaneous contraction and markedly exacerbated sarcomeric organization as reflected by sarcomeric α-actinin staining. This TNNT2 R173W mutation seems to affect only the CM function and not other cells from cardiovascular lineage (FIG. 29). Taken together, our data indicated that the TNNT2 R173W mutation caused impairment in force production of CMs, which might be the primary reason for the eventual appearance of the DCM clinical phenotype in patients (FIG. 30). We showed both β-blocker metoprolol can rescue the DCM iPSC-CM phenotype. In addition, over-expression with Serca2a, a novel gene therapy treatment for heart failure currently in clinical trials, can significantly improve the function of DCM iPSC-CMs. Gene expression profiling further identified several novel pathways, including ubiquitination and integrin signaling pathways, that are involved in Serca2a rescue. Taken together, our findings demonstrate that the iPSC platform opens new, exciting areas of research on investigating disease mechanisms and therapeutic targets for DCM.

Methods

Patient-specific iPSC derivation, culture, and characterization. All the protocols for this study were approved by the Stanford University Human Subjects Research Institutional Review Board. Generation, maintenance, and characterization of patient-specific iPSC lines were performed as previously described.

Immunofluorescence and alkaline phosphatase staining. Alkaline phosphatase (AP) staining was performed using the Quantitative Alkaline Phosphatase ES Characterization Kit (Chemicon) following the manufacturer's instruction. Immunofluorescence was performed using appropriate primary antibodies and AlexaFluor conjugated secondary antibodies (Invitrogen) as previously described. The primary antibodies for Oct3/4 (Santa Cruz), Sox2 (Biolegend), SSEA-3 (Millipore), SSEA-4 (Millipore), Tra-1-60 (Millipore), Tra-1-81 (Millipore), Nanog (Santa Cruz), AFP (Santa Cruz), smooth muscle actin (SMA) (Sigma), Tuj-1 (Covance), cTnT (Thermo Scientific), sarcomeric α-actinin (Clone EA-53, Sigma), Connexin-43 (Millipore), and Myosin light chain (MLC-2a) (Synaptic Systems) were used in this study.

Bisulphite pyrosequencing. One μg of sample DNA was bisulfate treated using the Zymo DNA Methylation Kit (Zymo Research) following the manufacturer's instruction. The PCR product was then converted to single-stranded DNA templates and sequenced by Pyrosequencing PSQ96 HS System (Biotage). The methylation status of each locus was analyzed individually as a T/C SNP using QCpG software (Biotage).

Cardiac differentiation of human ESCs and iPSCs. Differentiation of H7 ESCs and derived iPSC lines into the cardiac lineage was performed using the well established protocol described by Yang et al. Beating EBs were dissociated with type I collagenase (Sigma) and seeded on gelatin coated culture dishes, glass chamber slides, or glass coverslips for functional analyses.

Calcium imaging. Dissociated iPSC-CMs were seeded in gelatin-coated 4-well LAB-TEK® II chambers (Nalge Nunc International, chamber #1.5 German coverglass system) for calcium imaging. Cells were loaded with 5 μM Fluo-4 AM or Rhod-2 AM (for cells expressing GFP) and 0.02% Pluronic F-127 (all from Molecular Probes) in the Tyrodes solution (140 mM NaCl, 5.4 mM KCl, 1 mM $MgCl_2$, 10 mM glucose, 1.8 mM $CaCl_2$, and 10 mM HEPES pH 7.4 with NaOH at 25° C.) for 15 min at 37° C. Cells were then washed three times with the Tyrodes solution. Calcium imaging was conducted with a confocal microscope (Carl Zeiss, LSM 510 Meta) with a 63× lens (NA=1.4) using Zen software. Spontaneous $Ca^{2+}$ transients were acquired at room temperature using line scan mode at a sampling rate of 1.92 ms/line. A total of 10,000 lines were acquired for 19.2 s recoding.

Analysis of calcium imaging traces. $Ca^{2+}$ responses were quantified using Fiji, a derivative of ImageJ (National Institutes of Health) to average the fluorescence intensity of each line. The time-dependent $Ca^{2+}$ response was then analyzed for irregularities in timing of successive $Ca^{2+}$ transients and for the total $Ca^{2+}$ influx per transient using MATLAB. Time between transients (timing) was defined as the time between the peaks of two successive spikes. The spikes were determined by calculating the zero crossing of the second derivative using MATLAB's Signal Processing Toolbox. The total $Ca^{2+}$ released during each transient was determined by integrating the area underneath each wave with respect to the baseline. The baseline was defined as the median of all minima. Irregularity for both spike timing and amplitude was defined as the ratio of the standard deviation (s.d.) to the mean of a set of measurements.

Atomic force microscopy (AFM). iPSC-CMs were seeded on glass bottom petri dishes before each experiment, switched from culture media to warm Tyrode's solution. Cells were maintained at 36° C. for the entire experiment. Beating cells were interrogated by AFM (MFP-3D Bio, Asylum Research) using a silicon nitride cantilever (spring constants ~0.04 N/m, BudgetSensors). To measure forces, cells were gently contacted by the cantilever tip with 100 pN of force, with a typical cellular indentation of around 100-200 nm, then the cantilever tip remained in the position without Z-piezo feedback for multiple sequential two minute intervals while deflection data were collected at a sample rate of 2 kHz. Typical noise during these measurements was around 20 pN. Deflection data were converted to force by multiplying by the spring constant. Typically, 100-400 beats were collected for each single cell, and statistics were calculated for the forces, intervals between beats, and duration of each contraction for each cell. Forces across cells were compared using two tailed Student's t-test.

Adenovirus transduction of iPSC-CMs. First-generation type 5 recombinant adenoviruses carrying cytomegalovirus (CMV) promoter driving Serca2a plus a separate CMV promoter driving GFP (Ad.Serca2a) and adenoviruses carrying CMV promoter driving GFP only (Ad.GFP) as control were used. iPSC-CMs dissociated from beating EBs were transduced at MOI 100 overnight and then refreshed with culture medium (DMEM supplemented with 10% FBS). Cells were used for subsequent experiments 48 hours after transduction.

Statistical analysis. Data were analyzed using either Excel or R. Statistical differences among two groups were tested using two tailed Student's t-tests. Statistical differences among more than two groups were analyzed using one-way ANOVA tests followed by Tukey's Multiple Comparison Test. Significant differences were determined when p value is less than 0.05.

Genetic testing. Peripheral blood was drawn in EDTA from the patients and sent to GeneDx Laboratories (Gaithersburg, Md.) for isolation of genomic DNA and commercial genetic testing. The DNA was amplified and sequenced using a "next generation" solid-state sequence-by synthesis method (Illumina). The DCM gene panel includes sequencing of the complete coding regions and splice junctions of the following genes: LMNA, MYH7, TNNT2, ACTC1, DES, MYBPC3, TPM1, TNNI3, LDB3, TAZ, PLN, TTR, LAMP2, SGCD, MTTL1, MTTQ, MTTH, MTTK, MTTS1, MTTS2, MTND1, MTND5, and MTND6. Results were compared with the human reference sequence (c DNA NM_00108005). Possible disease associated sequences were confirmed by dideoxy DNA sequencing. The presence of candidate disease associated variants was also determined in 335 presumed healthy controls of mixed ethnicity. A variant was identified (p.Arg173Trp) in the TNNT2 gene. This is a non-conservative amino acid substitution of a hydrophilic, positive arginine with a hydrophobic, neutral tyrosine. This arginine is highly conserved at position 173 across several species. In silico analysis (PolyPhen) predicts the amino acid substitution to be damaging to the cardiac troponin T2 protein structure and function. This variant was not found in 335 control individuals of mixed descent.

Exome sequencing and data analysis. Genomic DNA from individual IIIa was subjected to exome sequencing using the Nimblegen SeqCap EZ Exome Library v2.0 (Roche Molecular Biochemicals). Thirty two most updated autosomal genes underlying DCM[1] (Supplementary Table 3) were examined for mutations. All of these genes were targeted in the exome capture and in total covered 190 kb. Sequencing with one lane of HiSeq (Illumina) generated median coverage of 217× (interquartile range 152× to 243×). Single nucleotide variant (SNVs) were found by using an analysis pipeline comprised of Novoalign, Picard, SAMtools, GATK, and ANNOVAR. SNPs were confirmed by comparing the SNPs data base dbSNP132. Deleterious SNVs were identified by the SIFT algorithm.

Microarray hybridization and data analysis. Total RNA samples from biological duplicates of undifferentiated iPSCs or 4-week-old CMs derived from control and DCM iPSCs (treated with or without Serca2a over-expression) were hybridized to Affymetrix GeneChip Human Gene 1.0 ST Array, and then normalized and annotated by the Affymetrix Expression Console software. The Pearson Correlation Coefficient was calculated for each pair of samples using the expression level of transcripts which show standard deviation greater than 0.2 among all samples. For hierarchical clustering, we used Pearson correlation for average linkage clustering. Ingenuity Pathway Analysis (IPA) tool was used to identify the enriched pathways. Only those pathways with the number of genes >5 were selected.

Cardiac differentiation of human ESCs and iPSCs. Human ESCs and iPSCs were cultured on Matrigel (BD Biosciences)-coated surface with mTESR-1 human pluripotent stem cell culture medium (STEMCELL Technologies) to 80% confluence. On day 0, cells were dissociated with Accutase (Sigma) to small clumps containing 10-20 cells and resuspended in 2 ml basic media (StemPro34, Invitrogen, containing 2 mM glutamine, Invitrogen, 0.4 mM monothioglycerol, Sigma, 50 μg/ml ascorbic acid, Sigma, and 0.5 ng/ml BMP4, R&D Systems) to form embryoid bodies (EBs). On day 1-4, BMP4 (10 ng/ml), human bFGF (5 ng/ml), and activin A (3 ng/ml) were added to the basic media for cardiac specification. On day 4-8, EBs were refreshed with basic media containing human DKK1 (50 ng/ml) and human VEGF (10 ng/ml), followed by basic media containing human bFGF (5 ng/ml) and human VEGF (10 ng/ml) starting day 8. All factors were obtained from R&D Systems. Cultures were maintained in a 5% $CO_2$/air environment.

Microelectrode array (MEA) recordings. One to six beating iPSC-CM EBs were plated 1-3 days prior to experiments at day 19-47 post differentiation on gelatin coated MEA probes (Alpha Med Scientific). Signals were acquired at 20 kHz with a MED64 amplifier (Alpha Med Scientific) and digitized using National Instruments A/D cards and a PC with MED64 Mobius QT software. Field potential duration (FPD) was measured and determined as described, and corrected offline using IGOR Pro (Lake Oswego) and MS Excel. FPD was normalized to the beat frequency using the Bazzet correction formula: $cFPD=FPD/\sqrt{Interspike\ interval}$. Statistical analyses comparing the DCM and control iPSC-CM electrophysiological parameters were performed using two tailed Student's t-tests.

Patch clamping. Dissociated iPSC-CMs were seeded on gelatin-coated 15 mm round coverslips in 24-well plates for experiments. Whole-cell patch clamp recordings in CMs generated from control and DCM iPSCs on coverslips were conducted using EPC-10 patch-clamp amplifier (HEKA) and an inverted microscope (Nikon, TE2000-U). Glass pipettes were prepared using borosilicate glasses with a filament (Sutter Instrument, #BF150-110-10) using the following parameters (Heat, Velocity, Time): 1) 740, 20, 250; 2) 730, 20, 250; 3) 730, 20, 250; 4) 710, 47, 250, using a micropipette puller (Sutter Instrument, Model P-87). Recordings were conducted using the following pipette solution: 120 mM K D-gluconate, 25 mM KCl, 4 mM MgATP, 2 mM NaGTP, 4 mM Na2-phospho-creatin, 10 mM EGTA, 1 mM CaCl2 and 10 mM HEPES (pH 7.4 with KCl at 25° C.) in Tyrodes solution (140 mM NaCl, 5.4 mM KCl, 1 mM $MgCl_2$, mM glucose, 1.8 mM $CaCl_2$, and 10 mM HEPES pH 7.4 with NaOH at 25° C.). Statistical analyses were performed using two tailed Student's t-tests.

Single cell microfluidic PCR. Single beating CMs were picked manually under the microscope. Each cell was introduced into PCR tubes containing 10 μl of a mixture of reaction buffer (CellsDirect kit, Invitrogen), TE buffer (Ambion), primers of interest (Applied Biosystems) and SuperScript III Reverse Transcriptase/Platinum Taq Mix (Invitrogen). Reverse transcription and specific transcript amplification were performed on the thermocycler (ABI Veriti) as follows: 50° C. for 15 min, 70° C. for 2 min, 94° C. for 2 min, then 94° C. for 15 sec, 60° C. for 30 sec, and 68° C. for 45 sec for 18 cycles, then 68° C. for 7 minutes. The amplified cDNA was loaded into Biomark 48.48 Dynamic Array chips using the Nanoflex IFC controller (Fluidigm). Threshold cycle (CT) as a measurement of relative fluorescence intensity was extracted by the BioMark Real-Time PCR Analysis software (Fluidigm).

Endothelial cell differentiation. iPSCs were dispersed into cell aggregates containing approximately 500 to 1,000 cells using 1 mg/ml collagenase IV (Invitrogen). Cell aggregates were suspension cultured in ultra-low attachment cell culture dishes in Knockout DMEM containing 20% ES-Qualified FBS (Invitrogen) supplemented with inductive cytokines (R&D Systems) as follows: day 0-7: 20 ng/ml BMP4; day 1-4: 10 ng/ml Activin A; day 2-14: 8 ng/ml FGF-2; day 4-14: 25 ng/ml VEGF-A. Endothelial progenitor cells were magnetically separated using mouse anti-human CD31 antibody (BD Biosciences) and expanded in EGM-2 endothelial cell culture medium (Lonza).

TABLE 1

Genetic screening of the DCM gene panel by next generation sequencing (Illumina)

| Gene Symbol | Protein Coded | NCBI Ref Gene No. | Mutation(s) |
|---|---|---|---|
| LMNA | lamin A/C | NG_008692 | None |
| MYH7 | beta-myosin heavy chain | NG_007884 | None |
| TNNT2 | cardiac muscle troponin T | NG_007556 | p.Arg173Trp |
| ACTC1 | alpha-cardiac actin | NG_007553 | None |
| DES | desmin | NG_008043 | None |
| MYBPC3 | cardiac myosin-binding protein C | NG_007667 | None |
| TPM1 | alpha tropomyosin | NG_007557 | None |
| TNNI3 | cardiac muscle troponin I | NG_007866 | None |
| LDB3 | LIM domain binding 3 (ZASP) | NG_008876 | None |
| TAZ | tafazzin | NG_009634 | None |
| PLN | phospholamban | NG_009082 | None |
| TTR | transthyretin | NG_009490 | None |
| LAMP2 | lysosomal-associated membrane protein 2 | NG_007995 | None |
| SGCD | delta sarcoglycan | NG_008693 | None |
| MTTL1 | mitochondrially encoded tRNA leucine 1 | NC_012920_TRNL1 | None |
| MTTQ | mitochondrially encoded tRNA glutamine | NC_012920_TRNQ | None |
| MTTH | mitochondrially encoded tRNA histidine | NC_012920_TRNH | None |
| MTTK | mitochondrially encoded tRNA lysine | NC_012920_TRNK | None |
| MTTS1 | mitochondrially encoded tRNA serine 1 | NC_012920_TRNS1 | None |
| MTTS2 | mitochondrially encoded tRNA serine 1 | NC_012920_TRNS2 | None |
| MTND1 | mitochondrially encoded NADH dehydrogenase 1 | NC_012920_ND1 | None |
| MTND5 | mitochondrially encoded NADH dehydrogenase 5 | NC_012920_ND5 | None |
| MTND6 | mitochondrially encoded NADH dehydrogenase 6 | NC_012920_ND6 | None |

TABLE 2

Clinical characteristics of the R173W DCM family

| Pedigree ID | Age (yrs) | Clinical Diagnosis | Genotype TNNT2 (p.Arg173Trp) | LVEDD (cm) | Ejection Fraction (%) | RV Size in Diastole (cm) | LA Size in Systole (cm) |
|---|---|---|---|---|---|---|---|
| Ia | 75 | DCM | Arg173Trp | 6.0 | 25-30% | 2.7 | 4.2 |
| Ib | 77 | — | Reference | NA | NA | NA | NA |
| IIa | 46 | DCM | Arg173Trp | 5.6 | 35%(2006), 50%(2011) | WNL | WNL |
| IIb | 50 | DCM | Arg173Trp | WNL | 40-45% | 3.32 | WNL |
| IIc | 48 | — | Reference | 5.3 | 65-70% | WNL | 4.0 |
| IIIa | 16 | DCM | Arg173Trp | 6.7 | 19% | 1.8 | 4.7 |
| IIIb | 18 | — | Reference | WNL | 58% | 2.9 | 3.6 |

LVEDD, Left Ventricular End Diastolic Diameter
Normal LVEDD Range (Adult), <5.5 cm
Normal ejection fraction (EF), >55%
WNL = Within Normal Limits
Normal right ventricle (RV) diastole size = <3.8 cm
Normal left atrium (LA) size systole = <4.2 cm

TABLE 3

Exome sequencing and screening of 32 recently updated list of genes causing DCM for patient IIIa did not uncover additional single nucleotide variants which could potentially account for the disease phenotype

| | |
|---|---|
| Whole exome SNVs called* | 49,143 |
| Number of called SNVs in dbSNP132 | 45,501 |
| Among 32 DCM genes (MYH6, MYH7, MYPN, TNNT2, SCN5A, MYBPC3, RBM20, TMPO, LAMA4, VCL, LDB3, TCAP, PSEN1, PSEN2, ACTN2, CRYAB, TPM1, ABCC9, ACTC1, PDLIM3, ILK, TNNC1, TNNI3, PLN, DES, SGCD, CSRP3, TTN, EYA4, ANKRD1, DMD, TAZ) | |
| SNVs called | 83 |
| Number of called SNVs in dbSNP132 | 78 |
| Non-synonymous SNVs | 37 |
| Deleterious by SIFT | 24 |
| Deleterious and absent in dbSNP132 | chr1: 201332477 C->T, TNNT2 R173W |
| | chr2: 179634421 T->G, TTN T2917P |
| | chr2: 179422181 C->T, TTN V20205I |
| | chr2: 179398195 C->G, TTN E25318Q |
| chr1: 201332477 C->T, TNNT2 R173W | Segregate with DCM and verified by genomic PCR and DNA sequencing |
| chr2: 179634421 T->G, TTN T2917P | Exome sequencing error verified by genomic PCR and DNA sequencing |
| chr2: 179422181 C->T, TTN V20205I | Not segregate with DCM and verified by genomic PCR and DNA sequencing |
| chr2: 179398195 C->G, TTN E25318Q | Not segregate with DCM and verified by genomic PCR and DNA sequencing |

*Using default GATK filter parameters for PASS
SNVs, single nucleotide variants

TABLE 4

Baseline electrophysiological parameters of iPSC-derived beating EBs obtained via MEA Recordings

| iPSC-EBs | Beats Per Minute | Field Potential Duration (ms) | Corrected Field Potential Duration (ms) | Minimum Amplitude (uV) | Maximum Amplitude (uV) |
|---|---|---|---|---|---|
| Control (n = 45) | 70.29 ± 2.74 | 466.56 ± 18.15 | 494.00 ± 17.70 | −325.90 ± 82.01 | 189.82 ± 39.54 |
| DCM (n = 57) | 64.88 ± 3.25 | 471.89 ± 20.81 | 470.66 ± 19.70 | −199.67 ± 33.79 | 106.20 ± 14.64 |

Mean ± s.e.m.

TABLE 5

Parameters of single DCM iPSC-CMs measured by AFM

| Cell Type | Frequency (sec) | Force (nN) | Beat Duration (sec) |
|---|---|---|---|
| Control (n = 13) | 1.01 ± 0.28 | 3.56 ± 0.97 | 0.34 ± 0.06 |
| DCM/DCM-Ad.GFP (n = 17) | 0.76 ± 0.09 | 0.65 ± 0.05 | 0.37 ± 0.07 |
| DCM-Ad.Serca2a (n = 12) | 1.09 ± 0.17 | 4.35 ± 1.01 | 0.16 ± 0.02 |

Mean ± s.e.m.

TABLE 6

Primers used for real time quantitative-PCR and allelic-PCR

| Amplicon | Forward Primer | Reverse Primer |
|---|---|---|
| ACTB | TGAAGTGTGACGTGGACATC (SEQ ID NO: 1) | GGAGGAGCAATGATCTTGAT (SEQ ID NO: 2) |
| OCT4 Total | AGCGAACCAGTATCGAGAAC (SEQ ID NO: 3) | TTACAGAACCACACTCGGAC (SEQ ID NO: 4) |
| OCT4 Endogenous | CCTCACTTCACTGCACTGTA (SEQ ID NO: 5) | CAGGTTTTCTTTCCCTAGCT (SEQ ID NO: 6) |
| SOX2 Total | AGCTACAGCATGATGCAGGA (SEQ ID NO: 7) | GGTCATGGAGTTGTACTGCA (SEQ ID NO: 8) |
| Sox2 Endogenous | CCCAGCAGACTTCACATGT (SEQ ID NO: 9) | CCTCCCATTTCCCTCGTTTT (SEQ ID NO: 10) |
| Klf4 Total | TCTCAAGGCACACCTGCGAA (SEQ ID NO: 11) | TAGTGCCTGGTCAGTTCATC (SEQ ID NO: 12) |
| Klf4 Endogenous | GATGAACTGACCAGGCACTA (SEQ ID NO: 13) | GTGGGTCATATCCACTGTCT (SEQ ID NO: 14) |
| C-MYC Total | ACTCTGAGGAGGAACAAGAA (SEQ ID NO: 15) | TGGAGACGTGGCACCTCTT (SEQ ID NO: 16) |
| C-MYC Endogenous | TGCCTCAAATTGGACTTTGG (SEQ ID NO: 17) | GATTGAAATTCTGTGTAACTGC (SEQ ID NO: 18) |
| Nanog Total | TGAACCTCAGCTACAAACAG (SEQ ID NO: 19) | TGGTGGTAGGAAGAGTAAAG (SEQ ID NO: 20) |
| TNNT2 Wt | GGAGGAGGAGCTCGTTTCTCTCAAAG (SEQ ID NO: 21) | CATGTTGGACAAAGCCTTCTTCTTCCG (SEQ ID NO: 22) |
| TNNT2 mutant | GGAGGAGGAGCTCGTTTCTCTCAAAG (SEQ ID NO: 23) | CATGTTGGACAAAGCCTTCTTCTTCCA (SEQ ID NO: 24) |

TABLE 7

Selected enriched pathways for rescued genes after Serca2a over-expression in DCM iPSC-CMs

| Canonical Pathways | Genes |
|---|---|
| Factors Promoting Cardiogenesis in Vertebrates | SMAD2, BMP4, LEF1, DKK1, BMP10, PDGFRB |
| Calcium Signaling | HDAC9, NFATC1, CASQ2, ACTA1. TMEM38B, NECAB1, ATP1A3, ATP2A2 |
| Integrin Signaling/Cytoskeletal | TSPAN7, ITGA8, TSPAN2, ACTA1, ITGB3, ACTA1, ITGB3, KIF1A, MAP2, DYNLT3, ITGA8 |
| Human Embryonic Stem Cell Pluripotency | SMAD2, BMP4, LEF1, BMP10, PDGFRB |
| Protein Ubiquitination Pathway | UBD, DNAJB4, USP17, DNAJB9, HSPA4L, USP17L2, USP17L6P, UGT2B7, UHRF1, UIMC1 |
| Wnt/β-catenin Signaling | UBD, GNAO1, LEF1, DKK1, SOX5 |
| G-Protein Coupled Receptor Signaling | GPR124, NPY1R, FSHR, GNAO1, VN1R1, BDKRB1, OR4F16, OR4F17, OR52N5, OR5R1 |
| Protein Kinase A Signaling | LEF1, NFATC1, HIST1H1B, HIST2H3C, HIST1H3F, HIST1H3J, HIST2H3A, HIST2H3D |

TABLE 8

Spread of iPSC lines analyzed by each assay

| | Phenotype | | | | | | | | | | | | | |
|---|---|---|---|---|---|---|---|---|---|---|---|---|---|---|
| | DCM | | | | | | | | | CON | | | | |
| Individual Lines | Ia | | IIa | | IIb | | IIIa | | Ib | | IIc | | IIb | |
| Clones | 1 | 2 | 1 | 2 | 1 | 3 | 1 | 3 | 1 | 4 | 2 | 3 | 1 | 2 |
| Teratoma assay | x | x | x | x | x | x | x | x | x | x | x | x | x | x |
| Karyotyping | x | x | x | x | x | x | x | x | x | x | x | x | x | x |
| Bisulphite | x | x | x | x | x | x | x | x | x | x | x | x | x | x |
| Beating EBs MEA baseline | | | x | x | x | x | x | x | x | x | | x | x | x |
| Patch clamping single CMs | | | x | | x | x | x | x | x | x | | x | x | x |
| MEA NE treatment beating EBs | | | x | | | | x | x | x | | | | x | x |
| Calcium imaging single CMs | x | | x | | x | x | x | x | x | x | x | x | x | x |
| CMs sarcomeric integrity analysis | x | x | x | x | x | x | x | x | x | x | x | x | x | x |
| Sarcomeric integrity after NE treatment | | | x | | x | x | x | | x | | | | | x |
| AFM single CMs | | | x | | | x | x | | | | | x | | |
| Metoprolol treatment | | | x | | | x | x | | | | | x | | |
| Serca2a Treatment | | | x | | | x | x | | | | | x | | |
| Microarray Serca2a Treatment | | | x | | | x | x | | | | | x | | |

Example 2

Cardiomyocytes from Patients with Hypertrophic Cardiomyopathy

Hypertrophic cardiomyopathy (HCM) is an autosomal dominant disease of the cardiac sarcomere, and is estimated to be the most prevalent hereditary heart condition in the world. Patients with HCM exhibit abnormal thickening of the left ventricular (LV) myocardium in the absence of increased hemodynamic burden and are at heightened risk for clinical complications such as progressive heart failure, arrhythmia, and sudden cardiac death (SCD). Molecular genetic studies from the past two decades have demonstrated that HCM is caused by mutations in genes encoding for proteins in the cardiac sarcomere. While identification of specific mutations has defined the genetic causes of HCM, the pathways by which sarcomeric mutations lead to myocyte hypertrophy and ventricular arrhythmia are not well understood. Efforts to elucidate the mechanisms underlying development of HCM have yielded conflicting results, paradoxically supporting models of both loss in myosin function and gain in myosin function to explain development of the disease. Attempts to resolve these discrepancies have been hampered by difficulties in obtaining human cardiac tissue and the inability to propagate heart samples in culture.

To circumvent these hurdles, we generated induced pluripotent stem cell-derived cardiomyocytes (iPSC-CMs) from a family of 10 individuals, half of whom carry an autosomal dominant missense mutation on exon 18 of the β myosin heavy chain gene (MYH7) encoding for an Arginine to Histidine substitution at amino acid position 663 (Arg663His). The generation of patient-specific iPSC-CMs allows for recapitulation of HCM at the single cell level and that preclinical modeling of HCM iPSC-CMs can elucidate the mechanisms underlying development of the disease. These findings validate iPSC technology as a novel method to understand how sarcomeric mutations cause the development of HCM and to identify new therapeutic targets for the disease.

Figure 31:
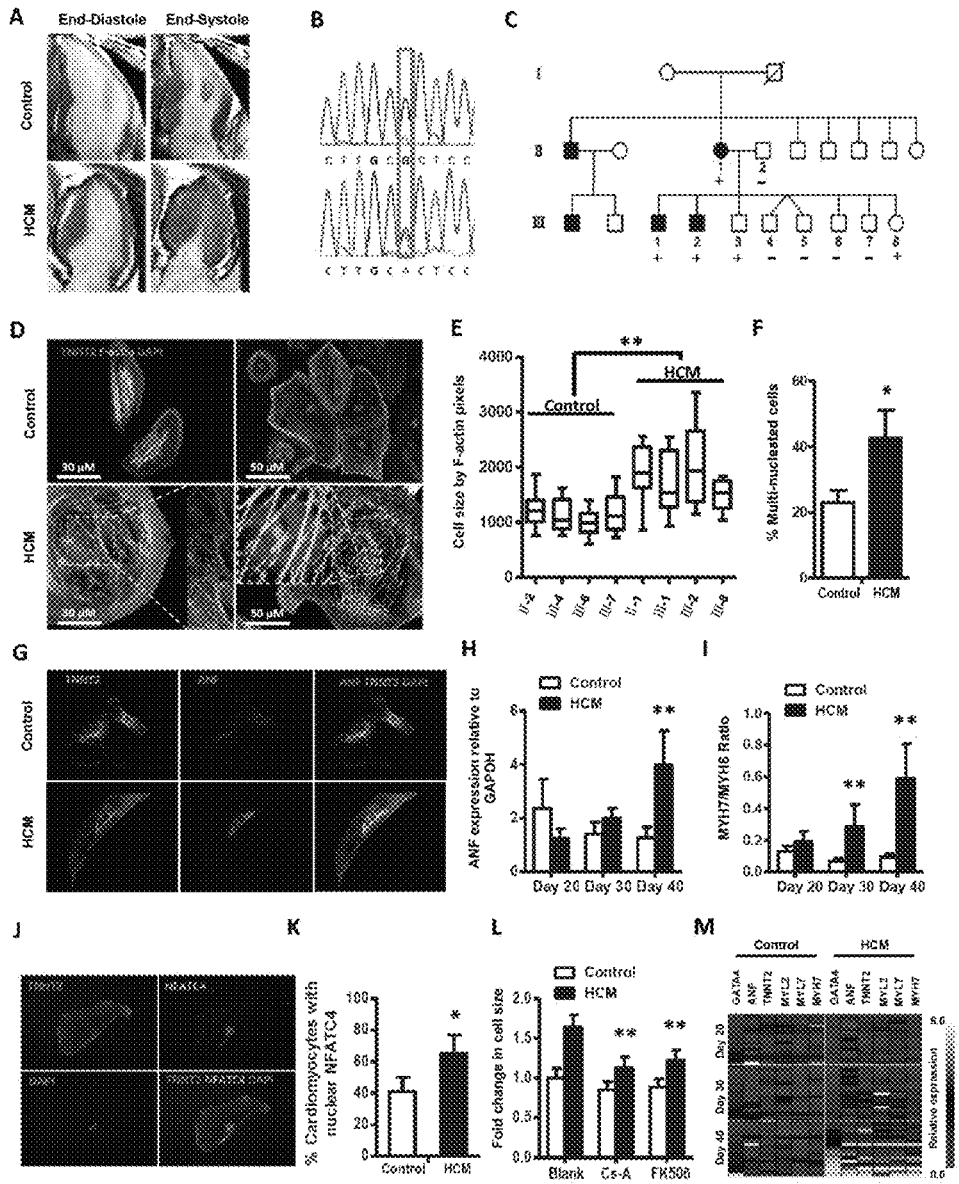
FIG. 31A-M. Generation and characterization of patient-specific HCM iPSC-CMs. (A) Representative long-axis MRI images of the proband and a control matched family member at end systole and end diastole demonstrating asymmetric hypertrophy of the inferior wall. (B) Confirmation of the Arg663His missense mutation on exon 18 of the MYH7 gene in HCM patients (II-1, III-1, III-2, III-3, and III-8) by PCR and sequence analysis. (C) Schematic pedigree of the proband carrying the Arg663His mutation in MYH7 recruited for this study (II-1) as well as her husband (II-2), and eight children (III-1 through III-8). Circles represent female family members and squares represent males. Solid symbols indicate clinical presentation of the HCM phenotype, whereas open symbols represent absence of presentation. "+" and "−" signs underneath family members indicate presence and absence of the Arg663His mutation respectively. Two individuals (III-3 and III-8) were found to carry the Arg663His mutation but had yet to present the HCM phenotype due to young age. (D) Representative immunostaining for cardiac troponin T and F-actin demonstrating increased cellular size and multinucleation in HCM iPSC-CMs as compared to control iPSC-CMs. (E) Quantification of cell size for 4 control iPSC-CM lines (II-2, III-4, III-6, III-7) (n=55 per patient line) and 4 HCM iPSC-CM lines (II-1, III-1, III-2, III-8) (n=59 per patient line) 40 days after induction of cardiac differentiation. (F) Quantification of multi-nucleation in control (n=55, 4 patient lines) and HCM iPSC-CMs (n=59, 4 patient lines). (G) Representative immunofluorescence staining reveals elevated ANF expression in HCM iPSC-CMs as compared to controls. (H) Changes in ANF gene expression as measured by single cell quantitative PCR in control and HCM iPSC-CMs at days 20, 30, and 40 following induction of cardiac differentiation (n=32 per time point, 5 patient lines). (I) Quantification of MYH7/MYH6 expression ratio in HCM iPSC-CMs and controls (n=32 per time point, 5 patient lines). (J) Representative immunofluorescence staining images revealing nuclear translocation of NFATC4 in HCM iPSC-CMs. (K) Percentage of cardiomyocytes exhibiting positive NFATC4 staining in control (n=187, 5 patient lines) and HCM iPSC-CMs (n=169, 5 patient lines). (L) Quantification of cell size in control and HCM iPSC-CMs following treatment with calcineurin inhibitors Cs-A and FK506 for 5 continuous days (n=50, 5 patient lines per group). (M) Heat map representations of gene expression in single control and HCM iPSC-CMs for genes associated with cardiac hypertrophy at days 20, 30, and 40 following induction of cardiac differentiation. * denotes $P<0.05$ HCM vs control, ** denotes $P<0.0001$ HCM vs control.

Recruitment of HCM family cohort and evaluation of disease genotype and phenotype. A 10 member family cohort that spanned two generations (II and III) was recruited for isolation of dermal fibroblasts. The proband was a 53-year old African American female patient (II-1) who presented at the hospital with palpitations, shortness of breath, and exertional chest pain. Results from comprehensive testing revealed concentric left ventricular hypertrophy (LVH) with prominent thickening of the inferior septum and inferior wall (FIG. 31A). To confirm presence of an HCM causing mutation, the proband's genomic DNA was screened for mutations with a panel of 18 genes associated with HCM. Nucleotide sequence analysis demonstrated a known familial HCM missense mutation on exon 18 of the β-myosin heavy chain gene, which causes an Arginine to Histidine substitution at amino acid position 663 (Arg663His; FIG. 31B). Subsequent genetic evaluation of the proband's family revealed that four of her eight children (III-1, III-2, III-3, III-8; ages 21, 18, 14, 10) carried the Arg663His mutation (FIG. 31C). The proband's family underwent the same comprehensive clinical evaluation, which revealed mild LVH in the two eldest carriers on echocardiography and MRI as well as occasional premature ventricular contractions on ambulatory monitoring. The two younger carriers (III-3 and III-8; ages 14 and 10) had not fully developed the phenotype, but did exhibit hyperdynamic function by echocardiography. The proband's husband (II-2; age 55) and other four children (III-4, III-5, III-6, III-7; ages 20, 16, 5 14, 13)

TABLE 9

Genes Screened

| Gene Symbol | Protein Code | NCBI Ref Gene No. | Mutation(s) |
|---|---|---|---|
| ACTC1 | alpha-cardiac actin | NG_007553 | None |
| CAV3 | caveolin 3 | NG_008797 | None |
| GLA | galactosidase alpha | NG_007119 | None |
| LAMP2 | lysosomal-associated membrane protein 2 | NG_007995 | None |
| MTTG | mitochondrial transfer RNA glycine | NC_012920_TRNG | None |
| MTTI | mitochondrial transfer RNA isoleucine | NC_012920_TRNI | None |
| MTTK | mitochondrial transfer RNA lysine | NC_012920_TRNK | None |
| MTTQ | mitochondrial transfer RNA glutamine | NC_012920_TRNQ | None |
| MYBPC3 | cardiac myosin-binding protein C | NG_007667 | None |
| MYH7 | beta-myosin heavy chain | NG_007884 | Arg663His |
| MYL2 | myosin regulatory light chain 2 | NG_007554 | None |
| MYL3 | myosin light chain 3 | NG_007555 | None |
| PRKAG2 | 5'-AMP-activated protein kinase subunit gamma-2 | NG_007486 | None |
| TNNC1 | troponin C | NG_008963 | None |
| TNNI3 | cardiac muscle troponin I | NG_007866 | None |
| TNNT2 | cardiac muscle troponin T | NG_007556 | None |
| TPM1 | alpha tropomyosin | NG_007553 | None |
| TTR | Transthyretin | NG_009490 | None |

Generation of patient-specific iPSCs and confirmation of pluripotency Patient-specific iPSCs were generated from primary fibroblasts of all 10 individuals through lentiviral infection with the reprogramming factors Oct-4, Sox-2, Klf-4 and c-Myc. A minimum of 3 distinct lines was generated per patient, and assayed for pluripotency through a battery of tests. Established iPSCs exhibited positive immunostaining for the ESC markers SSEA-4, TRA-1-60, TRA-1-81, Oct4, Sox2, Nanog, and alkaline phosphatase, as well as protein expression for the transcription factors Oct4, Sox2, and Nanog. Quantitative bisulfite pyrosequencing and quantitative RT-PCR demonstrated hypomethylation of Nanog and Oct-4 promoters, activation of endogenous pluripotency transcription factors, and silencing of lentiviral transgenes. Microarray analyses comparing whole genome expression profiles of dermal fibroblasts, iPSCs, and human ESCs (WA09 line) further confirmed successful reprogramming of all cell lines. Karyotyping demonstrated stable chromosomal integrity in all iPSC lines through passage 30. Spontaneous embryoid body (EB) and teratoma formation assays yielded cellular derivatives of all three germ layers in vitro and in vivo, confirming the pluripotent nature of generated iPSCs. Restriction enzyme digestion and sequencing verified the presence and absence of the Arg663His mutation in the MYH7 locus of HCM and control iPSCs respectively.

Differentiation of patient-specific iPSCs into cardiomyocytes. Established iPSC lines from all subjects were differentiated into cardiomyocyte lineages (iPSC-CMs) using standard 3D EB differentiation protocols. Ten to twenty days following the initiation of differentiation, spontaneously contracting EBs were observed to appear under light microscopy. Immunostaining for cardiac Troponin T indicated beating EBs from both control and HCM iPSC lines contained cardiomyocyte purities between 60-80%. Beating EBs were seeded on multi-electrode array (MEA) probes for evaluation of electrophysiological properties. Both control and HCM iPSC-derived EBs exhibited comparable beat frequencies, field potentials, and upstroke velocities at baseline. EBs were subsequently dissociated into single iPSC-CMs and plated on gelatin coated chamber slides for further analysis. Single dissociated iPSC-CMs from both HCM and control family members maintained spontaneous contraction and exhibited positive staining for sarcomeric proteins such as cardiac troponin T and myosin light chain (FIG. 31D).

iPSC-CMs carrying the Arg663His mutation recapitulate HCM phenotype in vitro Following cardiac differentiation and dissociation to single beating cells, diseased and control-matched iPSC-CMs were characterized in vitro for recapitulation of the HCM phenotype. Hypertrophic iPSC-CMs exhibited features of HCM such as cellular enlargement and multinucleation beginning in the sixth week following induction of cardiac differentiation (Arad et al., 2002). At day 40 post-induction, HCM iPSC-CMs were noticeably larger (1859+517 pixels; n=236, 4 patient lines) than control matched iPSC-CMs (1175+328 pixels; n=220, 4 patient lines) and exhibited significantly higher frequencies of multinucleation (HCM: 49.7+8.5%; n=236, 4 lines vs control: 23.0+3.7%; n=220, 4 lines) (FIG. 31D-F). Mutant iPSC-CMs also demonstrated other hallmarks of HCM including expression of atrial natriuretic factor (ANF), elevation of β-myosin/α-myosin ratio, calcineurin activation, and nuclear translocation of nuclear factor of activated T-cells (NFAT) as detected by immunostaining (FIG. 31G-K). As calcineurin-NFAT signaling is a key transcriptional activator for induction of hypertrophy in adult cardiomyocytes, we sought to test the importance of this pathway to hypertrophic development in HCM iPSC-CMs. Blockade of calcineurin-NFAT interaction in HCM iPSC-CMs by cyclosporin A (CsA) and FK506 reduced hypertrophy by over 40% (FIG. 31L). In the absence of inhibition, NFAT-activated mediators of hypertrophy such as GATA4 and MEF2C were found to be significantly upregulated in HCM iPSC-CMs beginning day 40 post-induction of cardiac differentiation, but not prior to this point. Taken together, these results indicate that calcineurin-NFAT signaling plays a central role in the development of the HCM phenotype as caused by the Arg663His mutation.

Single cell gene expression profiling demonstrates activation of HCM associated genes Clinical presentation of HCM typically occurs over the course of several decades in affected individuals. To investigate the temporal effects of the Arg663His mutation upon HCM development at the cellular level, we assessed the expression of hypertrophic-related genes in single purified iPSC-CMs from both HCM and control patients. Single contracting cardiomyocytes were manually lifted from culture dishes at days 20, 30, and 40 from initiation of differentiation and subjected to single cell quantitative PCR analysis using a panel of 32 cardiomyocyte-related transcripts. Beginning at day 40, hypertrophic related genes such as GATA4, TNNT2, MYL2, and MYH7 were found to be upregulated in HCM iPSC-CMs (FIG. 31M). No significant increases in expression of HCM related genes were found prior to this time point.

iPSC-CMs carrying the Arg663His mutation exhibit electrophysiological and contractile arrhythmia at the single cell level Arrhythmia is a clinical hallmark of HCM, and is responsible for a significant portion of morbidity and mortality associated with the disease including sudden cardiac death. We therefore next examined the electrophysiological properties of iPSCCMs carrying the Arg663His mutation by whole cell patch clamping. Both HCM and control iPSC-CMs contained myocyte populations characterized by nodal-like, ventricular-like, and atrial-like electrical waveforms. In the first four weeks following induction of differentiation, cells from both groups displayed similar action potential frequencies, peak amplitudes, and resting potentials. However, starting at day 30, a large subfraction (40.4+12.9%; n=131, 5 patient lines) of HCM myocytes as compared to controls (5.1+7.1%; n=144, 5 patient lines) were observed to exhibit arrhythmic waveforms including frequent small depolarizations that resembled delayed after depolarizations (DADs) that failed to trigger action potentials and clustered beats (FIG. 32A1, 32A2, 32B-C). Time-lapse videos of single beating iPSC-CMs under light microscopy confirmed that electrophysiological deficiencies resulted in contractile arrhythmia. Compared to control iPSCCMs (1.4+1.9%; n=68, 5 patient lines), which had regular beat intervals, HCM iPSC-CMs contained numerous cells (12.4+5.0%; n=64, 5 patient lines) that beat at irregular frequencies. Analysis of single cell video recordings by pixel quantification software confirmed the arrhythmic nature of HCM iPSC-CM contraction. Taken together, these findings demonstrate sarcomeric mutations are capable of inducing electrophysiological and contractile arrhythmia at the single cell level.

Figure 32:
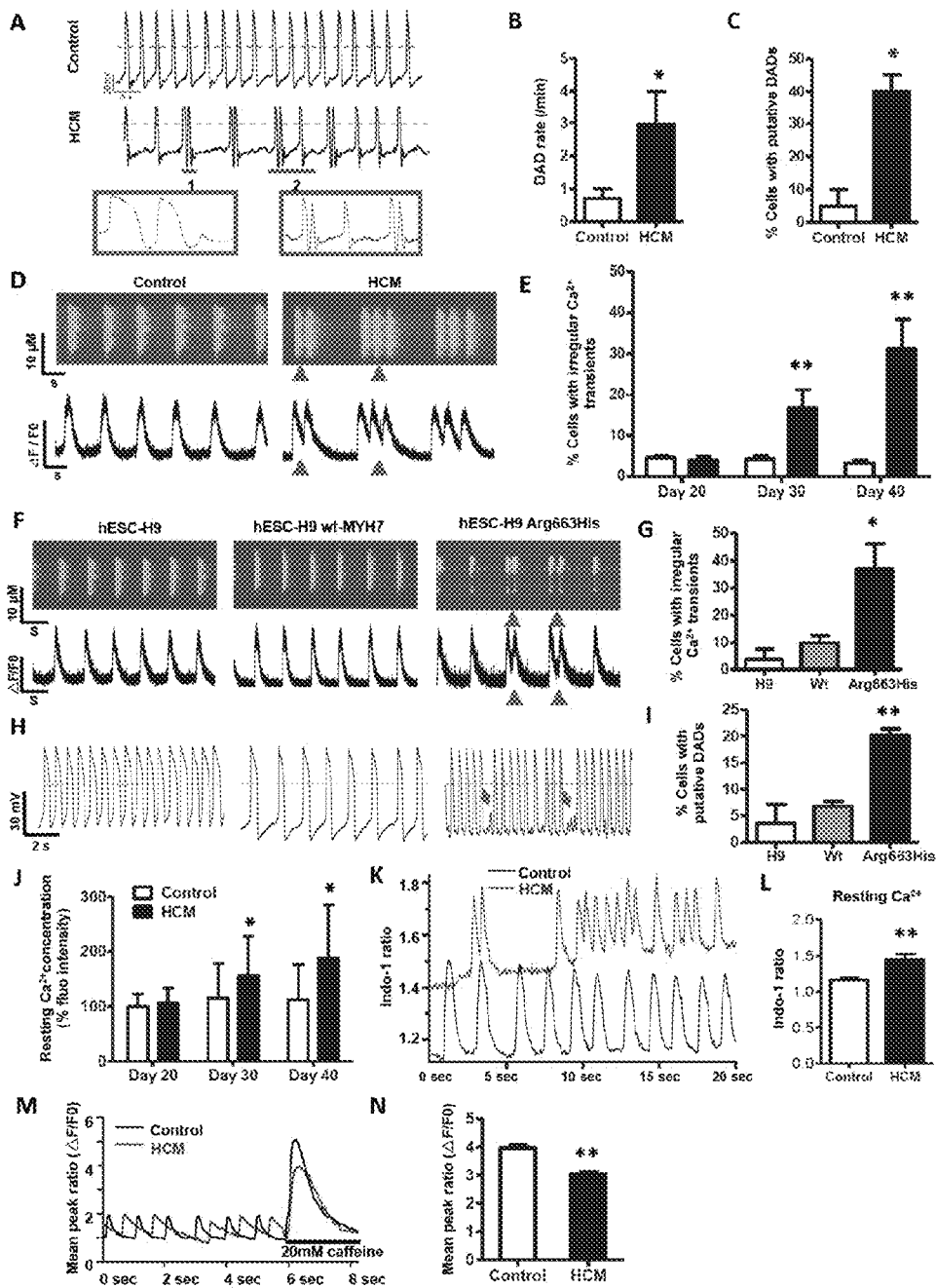
FIG. 32A-N. Assessment of arrhythmia and irregular $Ca^{2+}$ regulation in HCM iPSC-CMs. (A) Electrophysiological measurements of spontaneous action potentials in control and HCM iPSCCMs measured by patch clamp in current-clamp mode. Boxes indicate underlined portions of HCM iPSC-CM waveforms at expanded timescales demonstrating DAD-like arrhythmias. (B) Quantification of DAD occurrence in control (n=144, 5 patient lines) and HCM iPSC-CMs (n=131, 5 patient lines). DAD rate is defined as total DADs/total beats. (C) Quantification of percentage of control (n=144, 5 patient lines) and HCM iPSC-CMs (n=131, 5 patient lines) exhibiting putative DADs. (D) Representative line-scan images and spontaneous $Ca^{2+}$ transients in control and HCM iPSC-CMs. Red arrows indicate tachyarrhythmia-like waveforms observed in HCM cells but not control. (E) Quantification of percentages for control and HCM iPSC-CMs exhibiting irregular $Ca^{2+}$ transients at days 20, 30, and 40 following induction of cardiac differentiation (n=50, 5 patient lines per timepoint). (F) Representative line-scan images and spontaneous $Ca^{2+}$ transients for H9 hESC-CMs and hESC-CMs stably transduced with lentivirus driving expression of wild type MYH7 or mutant MYH7 carrying the Arg663His mutation. Red arrowheads indicate irregular $Ca^{2+}$ waveforms. (G) Quantification of cells exhibiting irregular $Ca^{2+}$ transients in WA09 hESC-CMs, hESC-CMs overexpressing wild-type MYH7, and hESCCMs overexpressing MYH7 carrying the Arg663His mutation (n=40, 5 patient lines per group). (H) Spontaneous action potentials recorded in current-clamp mode for hESC-CMs, hESC-CMs overexpressing wild type MYH7, and hESC-CMs overexpressing MYH7 carrying the Arg663His mutation. Red arrowheads indicate DAD-like waveforms. (I) Quantification of cells exhibiting DAD-like waveforms in hESC-CMs, hESC-CMs stably transduced with lentivirus driving expression of wild type MYH7 or mutant MYH7 carrying the Arg663His mutation (n=20, 5 patient lines per group). (J) Quantification of baseline Fluo-4 $Ca^{2+}$ dye intensities for control (n=122, 4 patient lines) and HCM iPSC-CMs (n=105, 4 patient lines). (K) Representative $Ca^{2+}$ transients of control and HCM iPSC-CMs using the Indo-1 ratiometric $Ca^{2+}$ dye. (L) Quantification of resting $Ca^{2+}$ levels by measurement of Indo-1 ratio in control (n=17, 4 patient lines) and HCM iPSC-CMs (n=26, 4 patient lines). (M) Representative $Ca^{2+}$ transient traces from control and HCM iPSC-CMs followed by caffeine exposure. (N) Mean peak amplitudes of ΔF/F0 ratios after caffeine administration representing release of SR $Ca^{2+}$ load for control (n=23, 3 lines) and HCM iPSC-CMs (n=35, 3 lines). * denotes $P<0.05$ HCM vs control, ** denotes $P<0.01$ HCM vs control.

Overexpression of the Arg663His mutation in normal hESC-CMs recapitulates calcium handling abnormalities of HCM iPSC-CMs Calcium ($Ca^{2+}$) plays a fundamental role in regulation of excitation-contraction coupling and electrophysiological signaling in the heart. To investigate the possible mechanisms underlying arrhythmia in myocytes carrying the Arg663His mutation, we next analyzed $Ca^{2+}$ handling properties of iPSC-CMs from control and HCM patients using the fluorescent $Ca^{2+}$ dye Fluo-4 acetoxymethyl ester (AM). Compared to iPSC-CMs derived from healthy individuals, HCM iPSC-CMs demonstrated significant $Ca^{2+}$ transient irregularities such as multiple events possibly related to triggered arrhythmia-like voltage waveforms, which were virtually absent in control cells (FIG. 32D-E). Interestingly, irregular $Ca_{2+}$ transients were observed to occur in HCM iPSC-CMs prior to the onset of cellular hypertrophy, suggesting that abnormal $Ca^{2+}$ handling may be a causal factor for the induction of the hypertrophic phenotype. Because variations inherent to spontaneous contractions can potentially confound $Ca^{2+}$ transients, we subjected HCM and control iPSC-CMs to 1 Hz pacing during line scanning. Consistent with data from spontaneous contraction, abnormal $Ca^{2+}$ transients were found to be common in HCM iPSC-CMs (12.5+4.9%; n=19, 5 patient lines) and absent in control iPSC-CMs (n=20, 5 patient lines). To further ensure that observed deficiencies in electrophysiology and $Ca^{2+}$ regulation were due to the Arg663His mutation, we next over-expressed the mutant form of myosin in human embryonic stem cell-derived cardiomyocytes (hESC-CMs; WA09 line). hESC-CMs overexpressing the Arg663His mutant MYH7 transcript were found to exhibit similar arrhythmias and abnormal $Ca^{2+}$ transients (FIG. 32F-I).

Previous reports have linked intracellular $Ca^{2+}$ ($[Ca^{2+}]_i$) elevation as a trigger for arrhythmia and cellular hypertrophy. We therefore further compared $[Ca^{2+}]_i$ in control and diseased iPSC-CMs. Preliminary quantification of $[Ca^{2+}]_i$ by Fluo-4 baseline intensity suggested that $[Ca^{2+}]_i$ was approximately 30% higher in HCM iPSCCMs (n=105, 4 patient lines) than control counterparts (n=122, 4 patient lines) at day 30 postinduction (FIG. 32J). To confirm diastolic $[Ca^{2+}]_i$ differences, we also used the ratiometric $Ca^{2+}$ dye Indo-1 in control and HCM iPSC-CMs. Indo-1 imaging demonstrated that diastolic $[Ca^{2+}]_i$ was higher (25.1% increase in Indo-1 ratio) in iPSC-CMs carrying the Arg663His mutation (n=26, 4 patient lines) as compared to control cells (n=17, 4 patient lines), and that arrhythmic activity was apparent in only the Arg663His myocytes. These findings emphasize a role for irregular $Ca^{2+}$ cycling in the pathogenesis of HCM (FIG. 32K-L).

Measurement of sarcoplasmic reticulum (SR) $Ca^{2+}$ stores further supported findings of elevated $[Ca^{2+}]_i$ in diseased iPSC-CMs as cytoplasmic retention of $Ca^{2+}$ has been shown to decrease SR $Ca^{2+}$ load by impeding SR $Ca^{2+}$ uptake. HCM and control iPSC-CMs were loaded with Fluo-4 and exposed to caffeine, which induces release of SR $Ca^{2+}$ stores into the cytoplasm. Myocytes carrying the Arg663His mutation were characterized by significantly smaller SR $Ca^{2+}$ release (mean peak ΔF/F0 ratio=3.05+0.20, n=35, 3 patient lines) as compared to control iPSC-CMs (mean peak ΔF/F0 ratio=3.96+0.18, n=23, 3 patient lines) (FIG. 32M-N). These findings demonstrate a central role for $Ca^{2+}$ cycling dysfunction and elevated $[Ca^{2+}]_i$ in the pathogenesis of HCM as caused by the Arg663His mutation.

Figure 33:
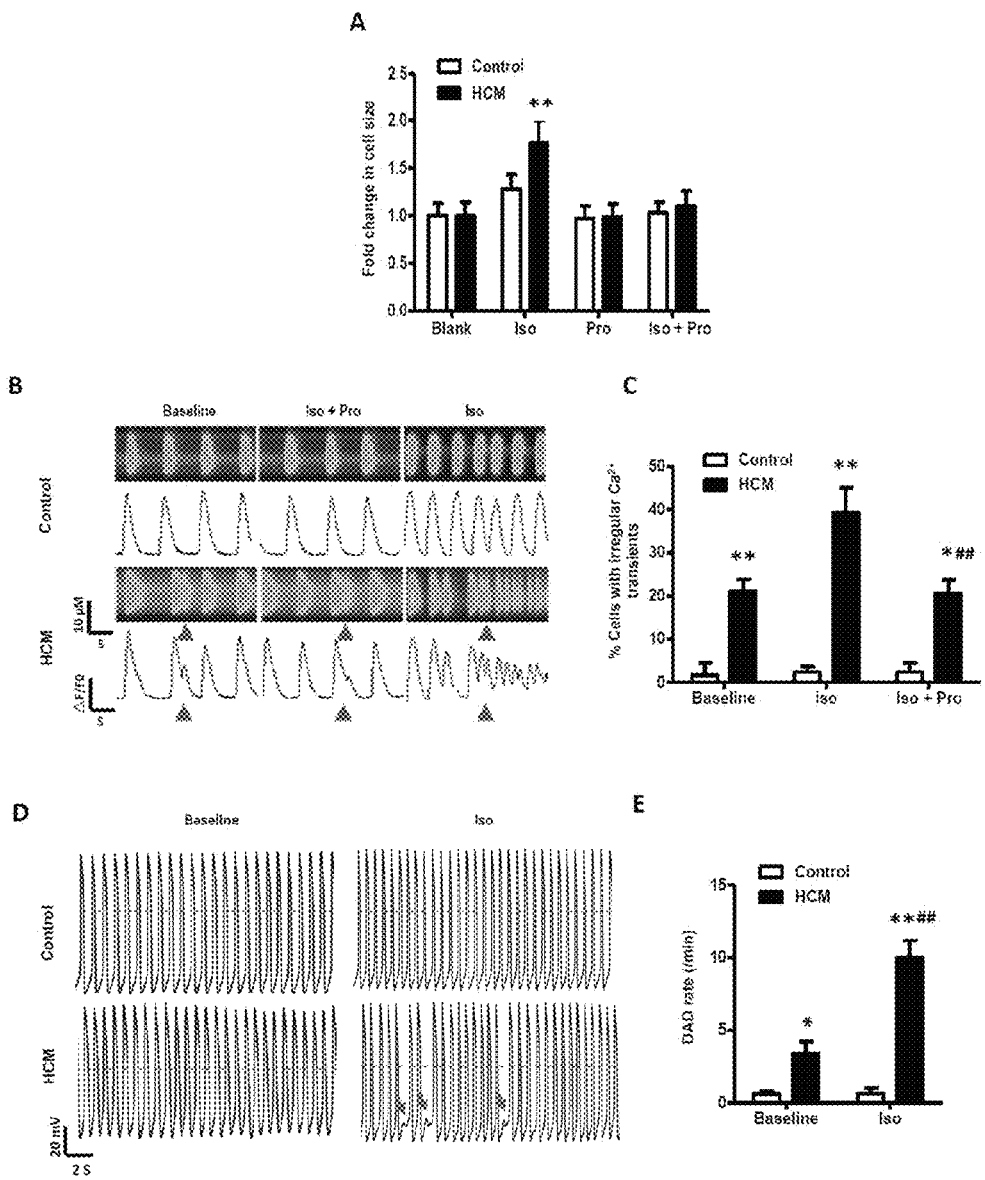
FIG. 33A-E. Exacerbation of the HCM phenotype by positive inotropic stress. (A) Inotropic stimulation of control (n=50, 5 patient lines) and HCM iPSC-CMs (n=50, 5 patient lines) by the β-agonist isoproterenol accelerated presentation of cellular hypertrophy in HCM iPSC-CMs as compared to control counterparts. Co-administration of the β-blocker propranolol prevented 20 catecholamine-induced hypertrophy in HCM iPSC-CMs (B) Representative $Ca^{2+}$ line scans and waveforms in control and HCM iPSC-CMs following positive inotropic stimulation by isoproterenol. Black arrowheads indicate abnormal $Ca^{2+}$ waveforms. (C) Quantification of control (n=50, 5 patient lines) and HCM iPSC-CMs (n=50, 5 patient lines) exhibiting irregular $Ca^{2+}$ transients in response to treatment by isoproterenol and co-administration of propranolol. (D) Electrophysiological measurement of spontaneous action potentials and arrhythmia in control and HCM iPSC-CMs at baseline, followed by positive inotropic stimulation by isoproterenol. Red arrows indicate DAD-like waveforms. (E) Quantification of DAD rate in control and HCM iPSC-CMs following isoproterenol administration (total DADs/total beats). * denotes $P<0.05$ HCM vs control, ** denotes $P<0.001$ HCM vs control, ## denotes $P<0.01$ iso+pro vs iso.

Inotropic stimulation exacerbates HCM phenotype in diseased iPSC-CMs Because iPSC-CMs carrying the Arg663His mutation recapitulated numerous aspects of the HCM phenotype in vitro, we hypothesized that our platform could also be used as a screening tool to assess the effect of pharmaceutical drugs upon HCM at the single cell level. To test the capacity of HCM iPSC-CMs to accurately model pharmaceutical drug response, we first subjected single control and diseased iPSC-CMs to positive inotropic stimulation, a known trigger for myocyte hypertrophy and ventricular tachycardia. Patient-specific cardiomyocytes were incubated β-adrenergic agonist (200 µM isoproterenol) on a daily basis for 5 days beginning 30 days after induction of differentiation. Previously HCM iPSC-CMs typically did not exhibit cellular hypertrophy until day 40 post-induction (FIG. 31E), but were found to increase in cell size by 1.7-fold between day 30 and 35 as compared to control counterparts when treated with isoproterenol (FIG. 33A). β-adrenergic stimulation was also found to severely exacerbate presentation of irregular $Ca^{2+}$ transients and arrhythmia in HCM iPSC-CMs (FIG. 33B-C). Importantly, co-administration of β-adrenergic blocker (400 µM propranolol) with isoproterenol significantly ameliorated catecholamine-induced exacerbation of hypertrophy, $Ca^{2+}$ handling deficiencies, and arrhythmia.

Figure 34:
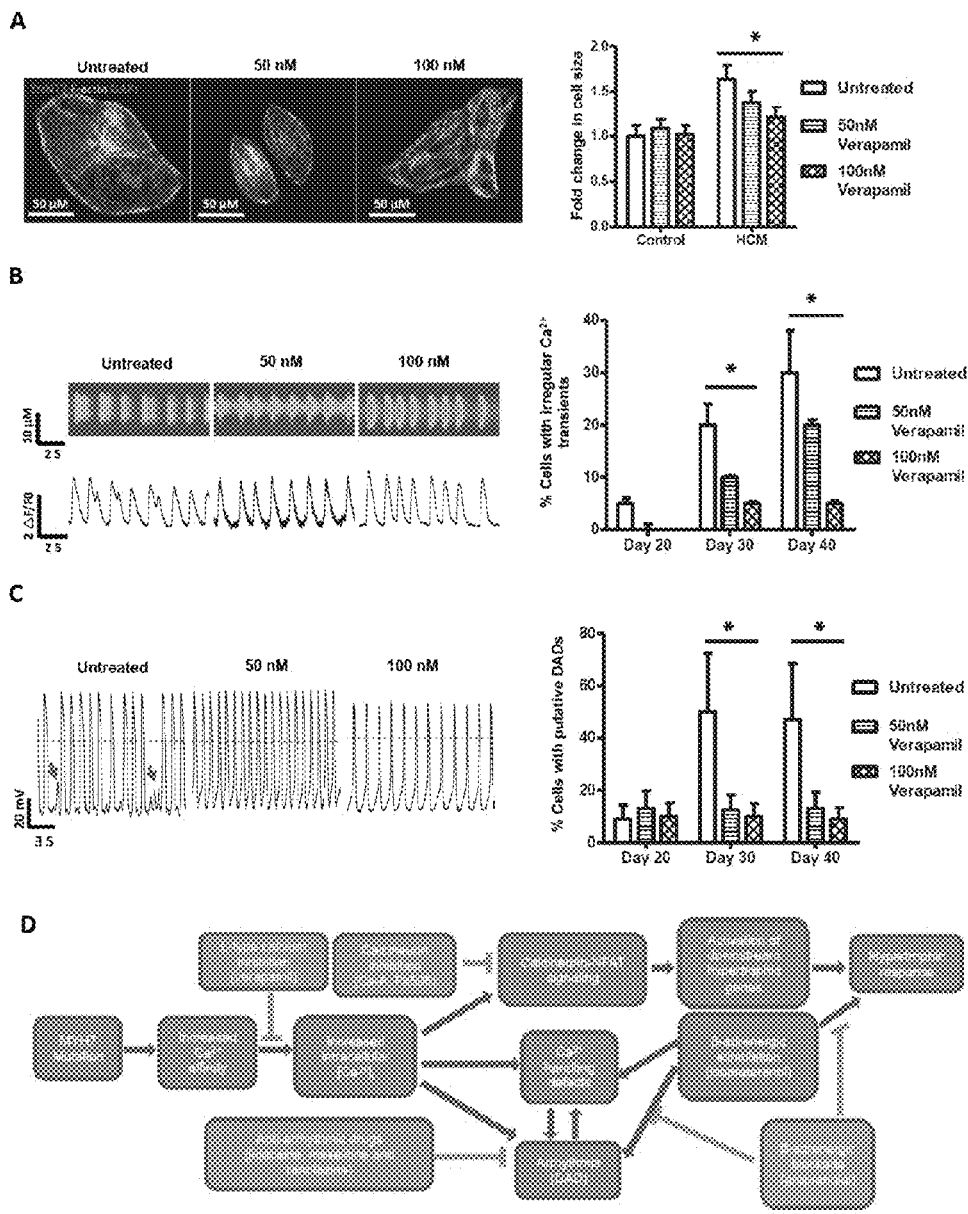
FIG. 34. Treatment of HCM iPSC-CMs by verapamil significantly mitigates development of the HCM phenotype. (A) Representative immunostaining images of HCM iPSC-CMs treated with 0 nM, 50 nM, and 100 nM of the L-type $Ca^{2+}$ channel blocker verapamil for 5 continuous days beginning 25 days after induction of cardiac differentiation. Quantification of relative cell sizes for HCM iPSC-CMs treated with verapamil (n=50, 5 patient lines per treatment group). (B) Representative $Ca^{2+}$ line scan images and waveforms of HCM iPSC-CMs treated with 0 nM, 50 nM, and 100 nM of verapamil for 5 continuous days. Quantification of percentages of HCM iPSC-CMs found to exhibit irregular $Ca^{2+}$ transients following treatment with verapamil (n=40, 5 patient lines per treatment group). (C) Representative electrophysiological recordings of spontaneous action potentials in HCM iPSC-CMs treated with 0 nM, 50 nM, and 100 nM of verapamil for 5 continuous days. Quantification of DAD frequencies in HCM iPSC-CMs 21 following treatment with verapamil (n=25, 5 patient lines per treatment group). (D) Schematic for development of the HCM phenotype as caused by HCM mutations in MYH7. Red boxes indicate potential methods to mitigate development of the disease. * denotes P<0.01 untreated vs 50 nM verapamil vs 100 nM verapamil.

Treatment of $Ca^{2+}$ dysregulation prevents development of the HCM phenotype We therefore assessed whether pharmaceutical inhibition of $Ca^{2+}$ entry could help prevent HCM phenotype development by treating control and mutant iPSC-CMs with the L-type $Ca^{2+}$ channel blocker verapamil. Compared to control cells, the spontaneous beating rate in HCM iPSC-CMs was relatively resistant to verapamil as detected by MEA dose-response experiments (HCM $IC_{50}$=930.61+80.0 nM, control $IC_{50}$=103.0+6.0 nM), consistent with the elevated $[Ca^{2+}]_i$ in iPSC-CMs carrying the Arg663His mutation. Remarkably, continuous addition of verapamil at therapeutic dosages (50-100 μM) to single diseased iPSC-CMs for 10-20 sequential days significantly ameliorated all aspects of the HCM phenotype including myocyte hypertrophy, $Ca^{2+}$ handling abnormalities, and arrhythmia (FIG. 34A-C).

Arrhythmic iPSC-CMs can be screened for potential pharmaceutical treatments at the single cell level As current pharmaceutical therapy for HCM includes the use of β-blockers and antiarrhythmics in addition to $Ca^{2+}$ channel blockers we further screened a panel of 12 other drugs used clinically to treat HCM for their potential to ameliorate the HCM phenotype at the single cell level. While verapamil was the only agent found to be capable of preventing cellular hypertrophy, anti-arrhythmic drugs which inhibit $Na_+$ influx such as lidocaine, mexiletine, and ranolazine also demonstrated potential to restore normal beat frequency in HCM iPSC-CMs, possibly through limiting $Ca^{2+}$ entry into the cell by the $Na_+/Ca_{2+}$ exchanger. Other anti-arrhythmic agents targeting $K_+$ channels and β-blockers administered in the absence of inotropic stimulation did not have any therapeutic effects in single cells. Altogether, these results implicate imbalances in $Ca^{2+}$ regulation as a central mechanism underlying development of HCM at the cellular level and demonstrate the potential of patient-specific iPSC-CMs as a powerful tool for the identification of novel pharmaceutical agents to treat HCM.

a number of characteristics of HCM including cellular hypertrophy, calcineurin-NFAT activation, upregulation of hypertrophic transcription factors, and contractile arrhythmia. Irregular $Ca^{2+}$ transients and elevation of diastolic $[Ca^{2+}]_i$ were observed to precede the presentation of other phenotypic abnormalities, strongly implicating dysregulation of $Ca^{2+}$ cycling as a central mechanism for pathogenesis of the disease. Imbalances in $Ca^{2+}$ homeostasis have been described as a key characteristic of HCM in numerous reports. However, little evidence exists to delineate whether these abnormalities are a symptom of HCM or a causal factor.

In this study, we present several lines of evidence for a crucial role of $Ca^{2+}$ in development of HCM as caused by the Arg663His mutation. Specifically, our findings show that an elevation in $[Ca^{2+}]_i$ mediated by the Arg663His mutation can induce both cellular hypertrophy and contractile arrhythmia. The sustained elevation of $[Ca^{2+}]_i$ is a known trigger for activation of calcineurin, a $Ca^{2+}$ dependent phosphatase that is a critical effector of hypertrophy in myocytes under conditions of stress. Activated calcineurin dephosphorylates NFAT3 transcription factors, allowing their translocation to the nucleus for direct interaction with classical mediators of hypertrophy such as GATA4 and MEF2. Time-based gene expression profiling of single iPSC-CMs following induction of cardiac differentiation confirmed this model as expression of downstream effectors of hypertrophy was observed to be

TABLE 10

Drugs that were Screened

| Drug | Class | Target | Video Analysis | Therapeutic Effect | Concentrations Tested |
| --- | --- | --- | --- | --- | --- |
| Quinidine | 1a | Na$^+$ channel blocker (intermediate association/dissociation) | x | no | 0.1-20 uM |
| Procainamide | 1a | Na$^+$ channel blocker (intermediate association/dissociation) | x | no | 1-200 uM |
| Lidocaine | 1b | Na$^+$ channel blocker (fast association/dissociation) | x | yes | 1-100 nM |
| Mexiletine | 1b | Na$^+$ channel blocker (fast association/dissociation) | x | yes | 1-50 uM |
| Ranolazine | NA | Late Na$^+$ channel blocker | x | yes | 0.1-10 uM |
| Flecainide | 1c | Na$^+$ channel blocker (slow association/dissociation) | x | no | 0.1-5 uM |
| Propafenone | 1c | Na$^+$ channel blocker (slow association/dissociation) | x | no | 1-100 uM |
| Propranolol | II | Beta-blocker | x | no | 1-400 uM |
| Metoprolol | II | Beta-blocker | x | no | 0.1-20 uM |
| Amiodarone | II | K$^+$ channel blocker | x | no | 0.1-10 uM |
| Sotalol | III | K$^+$ channel blocker | x | no | 1-400 uM |
| Dofetilide | III | K$^+$ channel blocker | x | no | 0.1-20 uM |
| Verapamil | IV | Ca$^{2+}$ channel blocker | x | yes* | 1-100 uM |

*Verapamil was only observed to have a therapeutic effect upon HCM iPSC-CMs following continuous addition to the culture media for 5 or more days in a row. Treatment for a period of time less than 5 days was not observed to have any therapeutic effects upon $Ca^{2+}$ handling or arrhythmogenicity. All other drug screening assays were conducted by incubating cells with respective pharmaceutical compounds at the listed concentrations for 10 minutes followed by washout.

The genetic causes of HCM were initially identified several decades ago. However, the mechanisms by which mutations in genes encoding for the cardiac sarcomere can cause development of HCM remain unclear. Generation of patient-specific iPSC-CMs has allowed for in depth modeling of hereditary cardiovascular disorders including dilated cardiomyopathy, LEOPARD and long QT syndrome. To elucidate the signaling pathways underlying HCM development, we utilized iPSC technology to generate functional cardiomyocytes from dermal fibroblasts of a 10-member family cohort, half of whom possess the HCM Arg663His mutation in the MYH7 gene. Patient-specific iPSC-CMs recapitulated dependent on $[Ca^{2+}]_i$ elevation and nuclear translocation of NFAT. Inhibition of calcineurin activity by CsA and FK506 as well as reduction of $Ca^{2+}$ influx by verapamil mitigated cellular hypertrophy, confirming the role of $Ca^{2+}$ dysfunction and calcineurin-NFAT signaling in HCM pathogenesis (FIG. 34D). Alterations in $Ca^{2+}$ cycling are a common trigger for cardiac arrhythmias, which are a serious clinical complication of HCM due to their potential to induce stroke or sudden cardiac death.

The mechanisms underlying arrhythmia in patients with HCM are not well understood, although reports have implicated interstitial fibrosis, abnormal cardiac anatomy, myocyte disarray, increased cell size, and dysfunction in $Ca^{2+}$ homeostasis as possible mediators. Our findings demonstrate for the first time that the Arg663His mutation in the MYH7 gene can directly result in electrophysiological and contractile arrhythmia at the single cell level even in the absence of cellular hypertrophy. The most likely mechanism for development of arrhythmia in individual HCM iPSC-CMs is buildup of $[Ca^{2+}]_i$, which induces delayed after depolarizations (DADs) whereby sarcoplasmic reticulum $Ca^{2+}$ release triggers transient inward current following action potential repolarization. Continued presentation of DADs can in turn lead to ventricular tachycardia and sudden cardiac death, as in patients suffering from recurrent arrhythmia.

Whole cell current clamp experiments of HCM iPSC-CMs supported this hypothesis through demonstration of frequent spontaneous DAD-like waveforms in diseased myocytes. We believe these results are the first report to demonstrate that specific HCM mutations such as Arg663His can act as direct triggers for arrhythmia at the single cell level.

The mechanistic role of elevated myocyte $Ca^{2+}$ loading seems to be central to both hypertrophy and arrhythmogenesis. Pharmaceutical drug screening of mutant iPSC-CMs further supported elevated $[Ca^{2+}]_i$ as a central mechanism for arrhythmia development. Of the 13 agents we used, only pharmaceutical blockade of $Ca^{2+}$ and $Na^+$ entry mitigated contractile arrhythmia in HCM iPSC-CMs. Reduction of $Na^+$ influx limits $[Ca^{2+}]_i$ by allowing $Na^+/Ca^{2+}$ exchange to remove $Ca^{2+}$ more readily. Our results demonstrate the utility of iPSC-based technology to model development of HCM and associated triggered arrhythmias, as well as to identify potential therapeutic agents for the disease. These results are the first to provide direct evidence of imbalances in $Ca^{2+}$ homeostasis as an initiating factor in the development of HCM at the single cell level.

EXPERIMENTAL PROCEDURES

Patient recruitment. Clinical evaluation of the proband and family included physical examination, ECG, cardiac magnetic resonance imaging (MRI), and 24-hour Holter monitoring. Results revealed hyperdynamic ventricular systolic function with near complete obliteration of the apical walls at end systole in the proband (II-1) and the eldest two carriers (III-1 and III-2). No delayed enhancement was found on contrast enhanced MRI in the proband or carriers. Ambulatory monitoring revealed occasional premature ventricular contractions. The youngest two carriers (III-3 and III-8; ages 14 and 10) exhibited hyperdynamic cardiac function but no other clinical features of HCM most likely due to their young age.

Isolation and maintenance of fibroblast cells. Freshly isolated skin biopsies were rinsed with PBS and transferred into a 1.5 ml tube. Tissue was minced in collagenase 1 (1 mg/ml in Dulbecco's modified Eagle medium (DMEM), Invitrogen, Carlsbad, Calif.) and allowed to digest for 6 hours at 37° C. Dissociated dermal fibroblasts were plated and maintained with DMEM containing 10% FBS (Invitrogen), Glutamax (Invitrogen), 4.5 g/L glucose (Invitrogen), 110 mg/L sodium pyruvate (Invitrogen), 50 U/mL penicillin (Invitrogen), and 50 g/mL streptomycin (Invitrogen) at 37° C., 95% air, and 5% CO2 in a humidified incubator. All cells were used for reprogramming within five passages.

Lentivirus production and transduction. 293FT cells (Invitrogen) were plated at 80% confluency on 100-mm dishes and transfected with 12 μg of the lentiviral vectors (Oct4, Sox2, Klf4, and c-MYC) plus 8 μg of packaging pPAX2 and 4 μg of VSVG plasmids using Lipofectamine 2000 (Invitrogen) following the manufacturer's instructions. Supernatant was collected 48 h after transfection, filtered through a 0.45-μm pore-size cellulose acetate filter (Millipore, Billerica, Mass.), and mixed with PEG-it Virus Concentration Solution (System Biosciences, Mountain View, Calif.) overnight at 4° C. Viruses were precipitated at 1,500 g the next day and resuspended with Opti-MEM medium (Invitrogen).

Derivation of patient-specific iPSCs. Generation, maintenance, and characterization of patient-specific iPSC lines were performed as previously described using lentivirus as produced above on Matrigel-coated tissue culture dishes (BD Biosciences, San Jose, Calif.) with mTESR-1 hESC Growth Medium (StemCell Technology, Vancouver, Canada)

Alkaline phosphatase staining. Alkaline phosphatase (AP) staining was conducted as in previous studies using the Quantitative Alkaline Phosphatase ES Characterization KitS (Millipore) using the manufacturer's instructions.

Immunofluorescence staining. Immunofluorescent stains were performed using the following primary antibodies: SSEA-3, SSEA-4, Tra-1-60, Tra-1-81, ANF, Tuj-1 (Millipore), Oct3/4, Nanog, AFP (Santa Cruz, Calif.), Sox2 (Biolegend, San Diego, Calif.), smooth muscle actin (Biolegend), sarcomeric α-actinin (Sigma, St. Louis, Mo.), (cTnT (Thermo Scientific Barrington, Ill.), Alexa Fluor 488 Phalloidin (invitrogen), Myosin light chain 2a (MLC2a), Myosin light chain 2v (MLC2v) (Synaptic Systems, Goettingen, Germany), and AlexaFluor conjugated secondary antibodies (Invitrogen) as previously described.

Bisulphite pyrosequencing. The Zymo DNA Methylation Kit (Zymo Research, Irvine, Calif.) was used to treat 1 μg of sample DNA with bisulfite as per the manufacturer's instructions. Following PCR, cDNA was converted to single-stranded DNA templates and sequenced by a Pyrosequencing PSQ96 HS System (Biotage, Charlotte, N.C.). QCpG software (Biotage) was used to analyze each individual locus as a T/C SNP.

Microarray hybridization and data analysis. RNA was isolated from iPSCs and hybridized to a Affymetrix GeneChip Human Gene 1.0 ST Array (Affymetrix, Santa Clara, Calif.). Expression was normalized and annotated by the Affymetrix Expression Console software (Affymetrix). The Pearson Correlation Coefficient was calculated for each pair of samples using the expression level of transcripts which shows standard deviation greater than 0.2 among all samples.

Spontaneous in vitro differentiation. For embroid body (EB) formation, iPSC colonies were dissociated on Matrigel coated plates with collagenase IV (Invitrogen), and seeded into low attachment 6-well plates in Knockout DMEM (Invitrogen) containing 15% KSR (Invitrogen), Glutamax (Invitrogen), 4.5 g/L glucose (Invitrogen), 110 mg/L sodium pyruvate (Invitrogen), 50 U/mL penicillin (Invitrogen), and 50 g/mL streptomycin (Invitrogen) to form embroid bodies (EBs). After 5 days, EBs were transferred to adherent, gelatin-coated chamber slides and cultured in the same medium for another 8 days.

Teratoma formation. $1 \times 10^6$ undifferentiated iPSCs were suspended in 10 μL Matrigel (BD Biosciences) and delivered by a 28.5 gauge syringe to the subrenal capsule of 8 week old SCID Beige mice. Eight weeks after cell delivery, tumors were explanted for hematoxylin and eosin staining.

Western blot. Whole cell extracts were isolated using RIPA buffer and 10 μg protein was analyzed by Western blot using specific antibodies against Oct4, c-Myc, Klf4, Actin (Santa Cruz), Sox2 (Biolegend).

Cardiac differentiation of human ESCs and iPSCs. Human H9 ESCs and iPSCs were differentiated into cardiomyocytes as previously described. Briefly, pluripotent stem cells were dissociated with accutase (Sigma) at 80% confluence into small clumps of 10-20 cells. Cells were resuspended in 2 ml basic media containing StemPro34 (Invitrogen), 2 mM glutamine (Invitrogen), 0.4 mM monothioglycerol (Sigma), 50 μg/ml ascorbic acid (Sigma), and 0.5 ng/ml BMP4 (R&D Systems, Minneapolis, Minn.) to form EBs. For days 1-4 of cardiac differentiation, cells were treated with 10 ng/ml BMP4, 5 ng/ml human bFGF (R&D Systems), and 3 ng/ml activin A (R&D Systems) added to the basic media. From days 4-8, EBs were refreshed with basic media containing human 50 ng/ml DKK1 (R&D Systems) and 10 ng/ml human VEGF (R&D Systems). From day 8 onwards, cells were treated with basic media containing 5 ng/ml human bFGF and 10 ng/ml human VEGF. Cultures were maintained in a 5% $CO_2$/air environment.

Measurement of cardiomyocyte size. For single cell cardiomyocyte analysis, beating EBs were plated on gelatin-coated dishes. Three days after plating, EBs were trypsinized, filtered through a 40-mm size pore-size filter, and single cells re-plated at low density on gelatin-coated chamber slides (Nalgene Nunc International, Rochester, N.Y.). Three days after re-plating, cells were fixed with 4% paraformaldehyde (Sigma), permeabilized in 0.3% Triton (Sigma), blocked using 5% BSA, and stained for cardiac troponin T (1:200, Thermo Fisher) overnight at 4° C. Stained cells were washed three times with PBS, and then incubated with the Alexa Fluor 488 phalloidin (Invitrogen), Alexa Fluor 594 donkey-anti-mouse antibody (Invitrogen) and DAPI (Invitrogen) for 1 h. Cellular areas of normal and HCM iPSC-CMs were analyzed using the ImageJ software package (National Institutes of Health, Bethesda, Md.).

Single cell microfluidic PCR. Single beating iPSC-CMs were picked manually under light microscopy and placed into separate PCR tubes for reverse transcription and cDNA amplification with specified primers as previously described. Amplified cDNA was loaded into Biomark 48.48 Dynamic Array chips (Fluidigm, South San Francisco, Calif.) for analysis by the BioMark Real-Time PCR Analysis software (Fluidigm).

Calcium ($Ca^{2+}$) imaging. iPSC-CMs were dissociated and seeded in gelatin-coated 8-well LAB-TEK® II chambers (Nalgene Nunc International) for calcium imaging. Cells were loaded with 5 μM Fluo-4 AM (Invitrogen) and 0.02% Pluronic F-127 (Invitrogen) in Tyrodes solution (140 mM NaCl, 5.4 mM KCl, 1 mM $MgCl_2$, 10 mM glucose, 1.8 mM $CaCl_2$, and 10 mM HEPES pH 7.4 with NaOH at 25° C.) for 15 min at 37° C. Following Fluo-4 loading, cells were washed three times with Tyrodes solution. Imaging was conducted with a confocal microscope (Carl Zeiss, LSM 510 Meta, Göttingen, Germany) with a 63× lens using Zen software (Carl Zeiss). For paced calcium dye imaging, fluorescence was measured at 495+20 nm excitation and 515±20 nm emission. Videos were taken at 20 fps for 10 s recording durations. Cells were stimulated at 1 and 2 Hz. Measurements were taken on an AxioObserver Z1 (Carl Zeiss) inverted microscope equipped with a Lambda DG-4 300 W Xenon light source (Sutter Instruments, Novato, Calif.), an ORCA-ER CCD camera (Hamamatsu, Bridgewater, N.J.), and AxioVison 4.7 software (Carl Zeiss). In each video frame, regions of interest (ROIs) were analyzed for changes in dye intensity f/f0, with the resting fluorescence value f0 determined at the first frame of each video. Background intensity was subtracted from all values, and plots were normalized to zero.

Measurement of basal $[Ca^{2+}]_i$ using Indo-1-AM. Cardiomyocytes were loaded in a culture medium containing 5 μM Indo-1 AM (Invitrogen) and 0.02% Pluronic F-127 (Invitrogen) for 20 minutes at 37° C. After Indo-1 loading, cells were washed three times with 2 mM $Ca^{2+}$ Ringer (155 mM NaCl, 4.5 mM KCl, 2 mM $CaCl_2$, 1 mM $MgCl_2$, 10 mM D-glucose, and 5 mM Na-HEPES, pH 7.4) and incubated for 20 minutes at room temperature to allow for Indo-1 de-esterification. Cardiomyocytes were imaged in $Ca^{2+}$ Ringer at 32° C. using a Zeiss Axiovert 200M epifluorescence microscope. Indo-1 was excited at 350±10 nm using a 0.6 UVND filter (to attenuate excitation intensity) and a 400 DCLP. The emitted light was separated using a Cairn Optosplit II (425 dichroic, 488/22 bandpass filter, Kent, UK). Spontaneous $Ca^{2+}$ transients were collected with 4×4 pixel binning in stream acquisition mode using Metamorph software (Molecular Devices, Sunnyvale, Calif.) at 100 ms exposures. For image analysis, short and long wavelength emission channels were aligned using the Cairn Image Splitter ImageJ plugin.

Caffeine treatment of iPSC-CMs. Cells were perfused with PBS containing 1.8 mM $Ca^{2+}$ and 1 mM Magnesium and paced at 1 Hz to view regular transients. A two second puff of 20 mM stock caffeine solution was delivered through a perfusion apparatus. Pacing was turned off prior to caffeine reaching the cells in order to accurately measure $Ca^{2+}$ release.

Analysis of calcium imaging linescans. Average fluorescence intensity for $Ca^{2+}$ linescans was quantified using Fiji (National Institutes of Health). Timing between transients was defined as the time between the peaks of two successive spikes. The $Ca^{2+}$ baseline was defined as the median of all minima of transients. Irregularity for spike timing was defined as the ratio of the standard deviation (s.d.) to the mean.

Microelectrode array (MEA) recordings. Control and HCM iPSCs were differentiated into beating EBs ranging from 60-80% purity of CMs and seeded onto multi-electrode 40 arrays for recording of field potential duration (FPD) and beating frequency (beats per minute, BPM) and interspike intervals (ISI). Beating iPSC-CM EBs were plated on gelatin-coated MEA probes (Alpha Med Scientific, Osaka, Japan) prior to experiments 20-40 days post-differentiation. Signals were acquired at 20 kHz with a MED64 amplifier (Alpha Med Scientific) and digitized using a PC with PCI-6071 A/D cards (National Instruments, Austin, Tex.) running MED64 Mobius QT software (Witwerx, Inc., Tustin, Calif.). All experiments were performed at 35.8 to 37.5° C. in DMEM without serum or antibiotics. Stock verapamil solutions were made in double distilled water at a 50 mM concentration. Dose-response experiments were performed by adding 0.4 to 2 μL of 1000× verapamil concentrations in DMEM to the 1-2 ml volume in the MEA probe for 10 minutes at each dose. Beating frequencies and field potential waveform data were extracted offline using Mobius QT and saved as CSV files. Waveform data was imported into IGOR Pro (Wavemetrics, Portland, Oreg.) for FPD and Vmax measurements. Beat frequencies were normalized to baseline for verapamil dose-response experiments and FPDs were adjusted to the beat frequency using the Bazett correction formula: cFPD=FPD/√Interspike interval.

Patch clamping. Whole-cell patch-clamp recordings were conducted using an EPC-10 patch-clamp amplifier (HEKA, Lambrecht, Germany). Contracting EBs were mechanically isolated, enzymatically dispersed into single cells and attached to gelatincoated glass coverslips (CS-22/40, Warner, Hamden, Conn.). While recordings, the coverslips containing plated cardiomyocytes or the hERG-HEK293 cells were transferred to a RC-26C recording chamber (Warner) mounted on to the stage of an inverted microscope (Nikon, Tokyo, Japan). The glass pipettes were prepared using thin-wall borosilicate glass (Warner) using a micropipette puller (Sutter Instrument, Novato, Calif.), polished using a microforge (Narishige, Tokyo, Japan) and had resistances between 2-4 MΩ. Extracellular solution perfusion was continuous using a rapid solution exchanger (Bio-logic, Grenoble, France) with solution exchange requiring 1 min. Data were acquired using PatchMaster software (HEKA, Germany) and digitized at 1.0 kHz. Data were analyzed using PulseFit (HEKA), Igor Pro (Wavemetrics, Portland, Oreg.), Origin 6.1 (Microcal, Northampton, Mass.), and Prism (Graphpad, La Jolla, Calif.). For the whole-cell patch clamp recordings of human cardiomyocytes generated from iPSCs, temperature was maintained constant by a TC-324B heating system (Warner) at 36-37° C. Current clamp recordings were conducted in normal Tyrode solution containing 140 mM NaCl, 5.4 mM KCl, 1 mM $MgCl_2$, 10 mM glucose, 1.8 mM $CaCl_2$ and 10 mM HEPES (pH 7.4 with NaOH at 25° C.). The pipette solution contained 120 mM KCl, 1 mM $MgCl_2$, 10 mM HEPES, 3 mM Mg-ATP, 10 mM EGTA (pH 7.2 with KOH at 25° C.). Verapamil (Sigma) was dissolved in H2O and prepared as a 10 mM stock in a glass vial. The stock solution was mixed vigorously for 10 min at room temperature. For testing, the compound was diluted in a glass vial using external solution; the dilution was prepared no longer than 30 min before using. Equal amounts of DMSO (0.1%) were present at final dilution.

Quantitative RT-PCR. Total mRNA was isolated using TRIZOL and 1 µg was used to synthesize cDNA using the Superscript II cDNA synthesis kit (Invitrogen). 0.25 µL of the reaction mixture was used to quantify gene expression by qPCR using SYBR® Green Master Mix (Invitrogen). Expression values were normalized to the average expression of GAPDH.

Drug treatment. Single contracting iPSC-CMs were treated with pharmaceutical agents for 10 minutes for immediate analysis followed by wash out. For inotropic stimulation experiments, 200 µM isoproterenol and 400 µM propranolol were added to the cell medium for 5 continuous days. Verapamil treatment was conducted by adding 50 µM and 100 µM to the culture medium of iPSC-CMs for 10-20 continuous days on a daily basis.

Example 3

Cardiomyocytes from Patients with Anthracycline Toxicity

Anthracycline-induced cardiotoxicity (and resistance to anthracycline-induced toxicity). Anthracyclines such as doxorubicin are frontline chemotherapeutic agents that are used to treat leukemias, Hodgkin's lymphoma, and solid tumors of the breast, bladder, stomach, lung, ovaries, thyroid, and muscle, among other organs. The primary side effect of anthracyclines is cardiotoxicity, which results in severe heart failure for many of the recipients receiving regimens utilizing this chemotherapeutic agent. Patient specific iPSC-cardiomyocytes (iPSC-CMs) were derived from individuals who are susceptible to anthracycline-induced cardiotoxicity as well as from individuals who are not susceptible to anthracycline-induced cardiotoxicity.

These cells are useful to defect and titrate cardiotoxic chemotherapeutic drugs, as well as identify genes responsible for susceptibility/resistance to anthracycline-induced cardiotoxicity. Age matched patients receiving anthracycline based chemo regimens were recruited, and assessed whether the patients developed anthracycline-induced heart failure. Skin samples were collected from the patients and generated iPSC-CMs from the fibroblasts.

Methods for the isolation and maintenance of fibroblast cells; derivation of patient-specific iPSC cell lines; and cardiac differentiation of cells was performed as described in Example 1 or Example 2.

Example 4

Cardiomyocytes from Patients with ARVD

Arrhythmogenic right ventricular dysplasia (ARVD). ARVD is an autosomal dominant disease of cardiac desmosomes that results in arrhythmia of the right ventricle and sudden cardiac death. It is second only to hypertrophic cardiomyopathy as a leading cause for sudden cardiac death in the young. Patient specific iPSC-cardiomyocytes (iPSC-CMs) were derived from a cohort of patients carrying a hereditary mutation for ARVD as well as from family matched controls. These cell lines may be used for drug screening and to identify molecular targets responsible for the disease phenotype.

Methods for the isolation and maintenance of fibroblast cells; derivation of patient-specific iPSC cell lines; and cardiac differentiation of cells was performed as described in Example 1 or Example 2.

The iPSC-CMs were made from the blood of 6 patients. 2 patients had a P672fsX740 2013delC mutation in the PKP2 gene, 2 patients had a Q617x1849C>T mutation in the PKP2 gene, and 2 patients were family matched control subjects.

Example 5

Cardiomyocytes from Patients with LVNC

Left Ventricular Non-Compaction (LVNC, aka non-compaction cardiomyopathy). LVNC is a hereditary cardiac disease which results from impaired development of the myocardium (heart muscle) during embryogenesis. Patients with mutations causing LVNC develop heart failure and abnormal cardiac electrophysiology early in life.

Patient specific iPSC-cardiomyocytes (iPSC-CMs) were derived from a cohort of LVNC patients as well as family matched control subjects. These cell lines may be used for drug screening and to identify molecular targets responsible for the disease phenotype.

Methods for the isolation and maintenance of fibroblast cells; derivation of patient-specific iPSC cell lines; and cardiac differentiation of cells was performed as described in Example 1 or Example 2.

Example 6

Cardiomyocytes from Patients with DILV

Double Inlet Left Ventricle (DILV). DILV is a congenital heart defect in which both the left and right atria feed into the left ventricle. As a result, children born with this defect only have one functional ventricular chamber, and trouble pumping oxygenated blood, into the general circulation.

Patient specific iPSC-cardiomyocytes (iPSC-CMs) were derived from one individual with this disease. These cell lines may be used for drug screening and to identify molecular targets responsible for the disease phenotype.

Methods for the isolation and maintenance of fibroblast cells; derivation of patient-specific iPSC cell lines; and cardiac differentiation of cells was performed as described in Example 1 or Example 2.

Example 7

Cardiomyocytes from Patients with Long QT

Long QT (Type-1) Syndrome (LQT-1, KCNQ1 mutation). Long QT syndrome (LOT) is a hereditary arrhythmic disease in which the QT phase of the electrocardiogram is prolonged, resulting in increased susceptibility for arrhythmia and sudden cardiac death. There are 13 known genes associated with LQT.

Patient specific iPSC-cardiomyocytes (iPSC-CMs) were derived from a cohort of LOT patients carrying a mutation in the KCNQ1 gene, which is the most commonly mutated LOT gene and responsible for 30-35% of all cases of the disease. The gene had a G269S missense mutation. These cell lines may be used for drug screening and to identify molecular targets responsible for the disease phenotype.

Methods for the isolation and maintenance of fibroblast cells; derivation of patient-specific iPSC cell lines; and cardiac differentiation of cells was performed as described in Example 1 or Example 2.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for cardiac disease-relevant screening of a candidate agent, the method comprising:
   (a) contacting the candidate agent with an isolated population of one or more cardiomyocytes or a panel of cardiomyocytes differentiated from one or more induced human pluripotent stem cells (iPS cells) comprising at least one allele encoding a mutation associated with a cardiac disease; and
   (b) determining the effect of the candidate agent on one or more phenotypes exhibited by one or more cardiomyocytes within the isolated population of cardiomyocytes or within the panel of cardiomyocytes wherein the one or more phenotypes are associated with dilated cardiomyopathy and are selected from the group consisting of: (a) relative to a cardiomyocyte produced from an induced pluripotent stem cell derived from a normal subject ("normal iPSC-CM"), an initial positive chronotropic effect in response to positive inotropic stress that later becomes negative with characteristics of failure; (b) a decreased inotropic activity compared to a normal iPSC-CM; (c) a decreased chronotropic activity compared to a normal iPSC-CM; (d) a decreased contractile force compared to a normal iPSC-CM; (e) a gene expression profile that differs from a gene expression profile of a normal iPSC-CM; (f) calcium transients that are smaller than calcium transients displayed by a normal iPSC-CM; (q) a weaker ability to resist mechanical stimulation as compared to a normal iPSC-CM; (h) cessation of spontaneous contraction in response to norepinephrine stimulation; (i) a higher frequency of punctate distribution of sarcomeric alpha-actin in comparison to a normal iPSC-CM; and (j) increased sarcomeric disorganization in response to contractile stimulation when compared to a normal iPSC-CM.

2. The method of claim 1, wherein the mutation is in a gene selected from cardiac troponin T (TNNT2); myosin heavy chain (MYH7); tropomyosin 1 (TPM1); myosin binding protein C (MYBPC3); 5'-AMP-activated protein kinase subunit gamma-2 (PRKAG2); troponin I type 3 (TNNI3); titin (TTN); myosin, light chain 2 (MYL2); actin, alpha cardiac muscle 1 (ACTC1); potassium voltage-gated channel, KQT-like subfamily, member 1 (KCNQ1); plakophilin 2 (PKP2); and cardiac LIM protein (CSRP3).

3. The method of claim 1, wherein the mutation is TNNT2 R173W.

4. The method of claim 1, wherein at least one cardiomyocyte within the isolated population of one or more cardiomyocytes or within the panel of cardiomyocytes exhibits, relative to a normal cardiomyocyte, an initially positive chronotropic effect in response to positive inotropic stress, that later become negative with characteristics of failure.

5. The method of claim 1, wherein the contacting the candidate agent comprises contacting the candidate agent with a panel of cardiomyocytes comprising at least two cardiomyocytes having differing genotypes.

6. The method of claim 1, wherein the contacting the candidate agent comprises contacting the candidate agent with a panel of cardiomyocytes comprising cardiomyocytes under differing environmental conditions.

7. The method of claim 6, wherein one or more of the environmental conditions comprises stimulation with a beta-adrenergic agonist.

8. The method of claim 1, wherein the determining the effect of the candidate agent comprises conducting a single cell analysis.

9. The method of claim 8, wherein the single cell analysis includes one or more of atomic force microscopy, microelectrode array recordings, patch clamping, single cell PCR, and calcium imaging.

10. The method of claim 1, wherein the candidate agent is a drug candidate.

11. The method of claim 1, wherein the candidate agent is a genetic agent.

12. An isolated population of one or more cardiomyocytes or a panel of cardiomyocytes differentiated from one or more human induced pluripotent stem cells (iPSC) comprising at least one allele encoding a mutation associated with a cardiac disease, wherein one or more cells within the isolated population of one or more cardiomyocytes or within the panel of cardiomyocytes display a phenotype associated with the cardiac disease, wherein the cardiac disease is dilated cardiomyopathy and wherein the phenotype of the one or more cells within the isolated population of one or more cardiomyocytes or within the panel of cardiomyocytes is one or more phenotypes selected from the group consisting of: (a) relative to a cardiomyocyte produced from an induced pluripotent stem cell derived from a normal subject ("normal iPSC-CM"), an initial positive chronotropic effect in response to positive inotropic stress that later becomes negative with characteristics of failure; (b) a decreased inotropic activity compared to a normal iPSC-CM; (c) a decreased chronotropic activity compared to a normal iPSC-CM; (d) a decreased contractile force compared to a normal iPSC-CM; (e) a gene expression profile that differs from a gene expression profile of a normal iPSC-CM; (f) calcium transients that are smaller than calcium transients displayed by a normal iPSC-CM; (g) a weaker ability to resist mechanical stimulation as compared to a normal iPSC-CM; (h) cessation of spontaneous contraction in response to norepinephrine stimulation; (i) a higher frequency of punctate distribution of sarcomeric alpha-actin in comparison to a normal iPSC-CM; and (j) increased sarcomeric disorganization in response to contractile stimulation when compared to a normal iPSC-CM.

13. The isolated population of one or more cardiomyocytes or the panel of cardiomyocytes of claim 12, wherein the mutation is in a gene selected from the group consisting of cardiac troponin T (TNNT2); myosin heavy chain (MYH7); tropomyosin 1 (TPM1); myosin binding protein C (MYBPC3); 5'-AMP-activated protein kinase subunit gamma-2 (PRKAG2); troponin I type 3 (TNNI3); titin (TTN); myosin, light chain 2 (MYL2); actin, alpha cardiac muscle 1 (ACTC1); potassium voltage-gated channel, KQT-like subfamily, member 1 (KCNQ1); plakophilin 2 (PKP2); and cardiac LIM protein (CSRP3).

14. The isolated population of one or more cardiomyocytes or the panel of cardiomyocytes of claim 12, wherein the mutation is TNNT2 R173W.

15. The isolated population of one or more cardiomyocytes or the panel of cardiomyocytes of claim 12, wherein relative to a normal iPSC-CM, cells within the isolated population of one or more cardiomyocytes or within the panel of cardiomyocytes have an initially positive chronotropic effect in response to positive inotropic stress that later becomes negative with characteristics of failure.

16. The isolated population of one or more cardiomyocytes or the panel of cardiomyocytes of claim 12, wherein the cardiomyocytes comprise cardiomyocytes having differing genotypes.

17. The isolated population of one or more cardiomyocytes or the panel of cardiomyocytes of claim 12, wherein the isolated population of one or more cardiomyocytes or the panel of cardiomyocytes comprises cardiomyocytes under differing environmental conditions.

18. The isolated population of one or more cardiomyocytes or the panel of cardiomyocytes of claim 17, wherein one or more of the environmental conditions comprises stimulation with a β-adrenergic agonist.

19. The isolated population of one or more cardiomyocytes or the panel of cardiomyocytes of claim 12, wherein the isolated population of one or more cardiomyocytes is a purified population of cardiomyocytes or wherein the panel of cardiomyocytes is a panel of purified cardiomyocytes.

20. The isolated population of one or more cardiomyocytes or the panel of cardiomyocytes of claim 12, wherein the isolated population of one or more cardiomyocytes or the panel of cardiomyocytes is situated in a multi-well container.

21. The isolated population of one or more cardiomyocytes or the panel of cardiomyocytes of claim 12, wherein the isolated population of one or more cardiomyocytes or the panel of cardiomyocytes is situated in a low-attachment container.

22. The isolated population of one or more cardiomyocytes or the panel of cardiomyocytes of claim 12, wherein the isolated population of one or more cardiomyocytes or the panel of cardiomyocytes is situated in a round plate container.

23. The isolated population of one or more cardiomyocytes or the panel of cardiomyocytes of claim 12, further comprising induced pluripotent stem cells.

24. The isolated population of one or more cardiomyocytes or the panel of cardiomyocytes of claim 12, wherein one or more cells within the isolated population of one or more cardiomyocytes or the panel of cardiomyocytes exhibit a decreased inotropic activity compared to a normal iPSC-CM.

25. The isolated population of one or more cardiomyocytes or the panel of cardiomyocytes of claim 12, wherein one or more cells within the isolated population of cardiomyocytes or within the panel of cardiomyocytes exhibit a decreased chronotropic activity compared to a normal iPSC-CM.

26. The isolated population of one or more cardiomyocytes or the panel of cardiomyocytes of claim 12, wherein the positive inotropic stress comprises treatment with a positive inotropic reagent.

27. The isolated population of one or more cardiomyocytes or the panel of cardiomyocytes of claim 26, wherein the positive inotropic reagent is a beta-adrenergic agonist.

28. The isolated population of one or more cardiomyocytes or the panel of cardiomyocytes of claim 12, wherein one or more cells within the isolated population of one or more cardiomyocytes or within the panel of cardiomyocytes exhibit a decreased contractile force compared to a normal iPSC-CM.

29. The isolated population of one or more cardiomyocytes or the panel of cardiomyocytes of claim 12, wherein one or more cells within the isolated population of cardiomyocytes or within the panel of cardiomyocytes exhibit calcium transients that are smaller than calcium transients displayed by a normal iPSC-CM.

30. The isolated population of one or more cardiomyocytes or the panel of cardiomyocytes of claim 12, wherein one or more cells within the isolated population of one or more cardiomyocytes or within the panel of cardiomyocytes exhibit a weaker ability to resist mechanical stimulation as compared to a normal iPSC-CM.

31. The isolated population of one or more cardiomyocytes or the panel of cardiomyocytes of claim 12, wherein one or more cells within the isolated population of one or more cardiomyocytes or within the panel of cardiomyocytes exhibit cessation of spontaneous contraction in response to norepinephrine stimulation.

32. The isolated population of one or more cardiomyocytes or the panel of cardiomyocytes of claim 12, wherein one or more cells within the isolated population of cardiomyocytes or within the panel of cardiomyocytes exhibit a higher frequency of punctate distribution of sarcomeric alpha-actin in comparison to a normal iPSC-CM.

33. The isolated population of one or more cardiomyocytes or the panel of cardiomyocytes of claim 12, wherein one or more cells within the isolated population of one or more cardiomyocytes or within the panel of cardiomyocytes exhibit an increased sarcomeric disorganization in response to contractile stimulation when compared to a normal iPSC-CM.

34. The isolated population of one or more cardiomyocytes or the panel of cardiomyocytes of claim 33, wherein the contractile stimulation comprises stimulation with norepinephrine.

35. A container comprising the isolated population of one or more cardiomyocytes or the panel of cardiomyocytes of claim 12, wherein the container further comprises a candidate agent.

36. The container of claim 35, wherein the candidate agent is a drug candidate.

37. The container of claim 35, wherein the candidate agent is a genetic candidate.

38. A container comprising the isolated population of one or more cardiomyocytes or the panel of cardiomyocytes of claim 12, wherein the container further comprises a chemotherapy drug.

39. The container of claim 38, wherein the chemotherapy drug has cardiotoxic effects.

40. The container of claim 38, wherein the chemotherapy drug is an anthracycline.

41. The container of claim 38, wherein the chemotherapy drug is doxorubicin.

42. The isolated population of one or more cardiomyocytes of claim 12.

43. The panel of cardiomyocytes of claim 12.

44. The method of claim 1, wherein at least one cardiomyocyte within the isolated population of one or more cardiomyocytes or within the panel of cardiomyocytes exhibits a decreased inotropic activity compared to a normal iPSC-CM.

45. The method of claim 1, wherein at least one cardiomyocyte within the isolated population of one or more cardiomyocytes or within the panel of cardiomyocytes exhibits a decreased chronotropic activity compared to a normal iPSC-CM.

46. The method of claim 1, wherein the positive inotropic stress comprises treatment with a positive inotropic reagent.

47. The method of claim 1, wherein the positive inotropic reagent is a beta-adrenergic agonist.

48. The method of claim 1, wherein at least one cardiomyocyte within the isolated population of one or more cardiomyocytes or within the panel of cardiomyocytes exhibits a decreased contractile force compared to a normal iPSC-CM.

49. The method of claim 1, wherein at least one cardiomyocyte within the isolated population of one or more cardiomyocytes or within the panel of cardiomyocytes exhibits calcium transients that are smaller than calcium transients displayed by a normal iPSC-CM.

50. The method of claim 1, wherein at least one cardiomyocyte within the isolated population of one or more cardiomyocytes or within the panel of cardiomyocytes exhibits a weaker ability to resist mechanical stimulation as compared to a normal iPSC-CM.

51. The method of claim 1, wherein at least one cardiomyocyte within the isolated population of one or more cardiomyocytes or within the panel of cardiomyocytes exhibits cessation of spontaneous contraction in response to norepinephrine stimulation.

52. The method of claim 1, wherein at least one cardiomyocyte within the isolated population of one or more cardiomyocytes or within the panel of cardiomyocytes exhibits a higher frequency of punctate distribution of sarcomeric alpha-actin in comparison to a normal iPSC-CM.

53. The method of claim 1, wherein at least one cardiomyocyte within the isolated population of one or more cardiomyocytes or within the panel of cardiomyocytes exhibits an increased sarcomeric disorganization in response to contractile stimulation when compared to a normal iPSC-CM.

54. The method of claim 1 or 53, wherein the contractile stimulation comprises stimulation with norepinephrine.

* * * * *

```
SEQUENCE LISTING

<160> NUMBER OF SEQ ID NOS: 34

<210> SEQ ID NO 1
<211> LENGTH: 20
<212> TYPE: DNA
<213> ORGANISM: Homo sapiens

<400> SEQUENCE: 1
tgaagtgtga cgtggacatc                                              20

<210> SEQ ID NO 2
<211> LENGTH: 20
<212> TYPE: DNA
<213> ORGANISM: Homo sapiens

<400> SEQUENCE: 2
ggaggagcaa tgatcttgat                                              20

<210> SEQ ID NO 3
<211> LENGTH: 20
<212> TYPE: DNA
<213> ORGANISM: Homo sapiens

<400> SEQUENCE: 3
agcgaaccag tatcgagaac                                              20

<210> SEQ ID NO 4
<211> LENGTH: 20
<212> TYPE: DNA
<213> ORGANISM: Homo sapiens

<400> SEQUENCE: 4
ttacagaacc acactcggac                                              20

<210> SEQ ID NO 5
<211> LENGTH: 20
<212> TYPE: DNA
<213> ORGANISM: Homo sapiens

<400> SEQUENCE: 5
cctcacttca ctgcactgta                                              20
```

```
<210> SEQ ID NO 6
<211> LENGTH: 20
<212> TYPE: DNA
<213> ORGANISM: Homo sapiens

<400> SEQUENCE: 6
caggtttcct ttccctagct                                               20

<210> SEQ ID NO 7
<211> LENGTH: 20
<212> TYPE: DNA
<213> ORGANISM: Homo sapiens

<400> SEQUENCE: 7
agctacagca tgatgcagga                                               20

<210> SEQ ID NO 8
<211> LENGTH: 20
<212> TYPE: DNA
<213> ORGANISM: Homo sapiens

<400> SEQUENCE: 8
ggtcatggag ttgtactgca                                               20

<210> SEQ ID NO 9
<211> LENGTH: 19
<212> TYPE: DNA
<213> ORGANISM: Homo sapiens

<400> SEQUENCE: 9
cccagcagac ttcacatgt                                                19

<210> SEQ ID NO 10
<211> LENGTH: 20
<212> TYPE: DNA
<213> ORGANISM: Homo sapiens

<400> SEQUENCE: 10
cctcccattt ccctcgtttt                                               20

<210> SEQ ID NO 11
<211> LENGTH: 20
<212> TYPE: DNA
<213> ORGANISM: Homo sapiens

<400> SEQUENCE: 11
tctcaaggca cacctgcgaa                                               20

<210> SEQ ID NO 12
<211> LENGTH: 20
<212> TYPE: DNA
<213> ORGANISM: Homo sapiens

<400> SEQUENCE: 12
tagtgcctgg tcagttcatc                                               20

<210> SEQ ID NO 13
<211> LENGTH: 20
<212> TYPE: DNA
<213> ORGANISM: Homo sapiens

<400> SEQUENCE: 13
```
gatgaactga ccaggcacta                                              20

<210> SEQ ID NO 14
<211> LENGTH: 20
<212> TYPE: DNA
<213> ORGANISM: Homo sapiens

<400> SEQUENCE: 14
gtgggtcata tccactgtct                                              20

<210> SEQ ID NO 15
<211> LENGTH: 20
<212> TYPE: DNA
<213> ORGANISM: Homo sapiens

<400> SEQUENCE: 15
actctgagga ggaacaagaa                                              20

<210> SEQ ID NO 16
<211> LENGTH: 19
<212> TYPE: DNA
<213> ORGANISM: Homo sapiens

<400> SEQUENCE: 16
tggagacgtg gcacctctt                                               19

<210> SEQ ID NO 17
<211> LENGTH: 20
<212> TYPE: DNA
<213> ORGANISM: Homo sapiens

<400> SEQUENCE: 17
tgcctcaaat tggactttgg                                              20

<210> SEQ ID NO 18
<211> LENGTH: 22
<212> TYPE: DNA
<213> ORGANISM: Homo sapiens

<400> SEQUENCE: 18
gattgaaatt ctgtgtaact gc                                           22

<210> SEQ ID NO 19
<211> LENGTH: 20
<212> TYPE: DNA
<213> ORGANISM: Homo sapiens

<400> SEQUENCE: 19
tgaacctcag ctacaaacag                                              20

<210> SEQ ID NO 20
<211> LENGTH: 20
<212> TYPE: DNA
<213> ORGANISM: Homo sapiens

<400> SEQUENCE: 20
tggtggtagg aagagtaaag                                              20

<210> SEQ ID NO 21
<211> LENGTH: 26
<212> TYPE: DNA
<213> ORGANISM: Homo sapiens

<400> SEQUENCE: 21

-continued ggaggaggag ctcgtttctc tcaaag                                    26

<210> SEQ ID NO 22
<211> LENGTH: 27
<212> TYPE: DNA
<213> ORGANISM: Homo sapiens

<400> SEQUENCE: 22
catgttggac aaagccttct tcttccg                                   27

<210> SEQ ID NO 23
<211> LENGTH: 26
<212> TYPE: DNA
<213> ORGANISM: Homo sapiens

<400> SEQUENCE: 23
ggaggaggag ctcgtttctc tcaaag                                    26

<210> SEQ ID NO 24
<211> LENGTH: 27
<212> TYPE: DNA
<213> ORGANISM: Homo sapiens

<400> SEQUENCE: 24
catgttggac aaagccttct tcttcca                                   27

<210> SEQ ID NO 25
<211> LENGTH: 13
<212> TYPE: DNA
<213> ORGANISM: Homo sapiens

<400> SEQUENCE: 25
gaggcccgga aga                                                  13

<210> SEQ ID NO 26
<211> LENGTH: 13
<212> TYPE: DNA
<213> ORGANISM: Homo sapiens

<400> SEQUENCE: 26
gaggcctgga aga                                                  13

<210> SEQ ID NO 27
<211> LENGTH: 33
<212> TYPE: DNA
<213> ORGANISM: Homo sapiens

<400> SEQUENCE: 27
ggctgaggat gaggcctgga agaagaaggc ttt                            33

<210> SEQ ID NO 28
<211> LENGTH: 33
<212> TYPE: DNA
<213> ORGANISM: Homo sapiens

<400> SEQUENCE: 28
ggctgaggat gaggcctgga agaagaaggc ttt                            33

<210> SEQ ID NO 29
<211> LENGTH: 33
<212> TYPE: DNA
<213> ORGANISM: Homo sapiens

```
<400> SEQUENCE: 29
ggctgaggat gaggcctgga agaagaaggc ttt                             33

<210> SEQ ID NO 30
<211> LENGTH: 33
<212> TYPE: DNA
<213> ORGANISM: Homo sapiens

<400> SEQUENCE: 30
ggctgaggat gaggcctgga agaagaaggc ttt                             33

<210> SEQ ID NO 31
<211> LENGTH: 33
<212> TYPE: DNA
<213> ORGANISM: Homo sapiens

<400> SEQUENCE: 31
ggctgacgat gaggcctgga agaagaaggc ttt                             33

<210> SEQ ID NO 32
<211> LENGTH: 33
<212> TYPE: DNA
<213> ORGANISM: Homo sapiens

<400> SEQUENCE: 32
ggctgaggat gaggcctgga agaagaaggc ttt                             33

<210> SEQ ID NO 33
<211> LENGTH: 33
<212> TYPE: DNA
<213> ORGANISM: Homo sapiens

<400> SEQUENCE: 33
ggctgaggat gaggcctgga agaagaaggc ttt                             33

<210> SEQ ID NO 34
<211> LENGTH: 33
<212> TYPE: DNA
<213> ORGANISM: Homo sapiens

<400> SEQUENCE: 34
ggctgaggat gaggcctgga agaagaaggc ttt                             33
```